US012644819B2

(12) United States Patent (10) Patent No.: US 12,644,819 B2
Nolan et al. (45) Date of Patent: Jun. 2, 2026

(54) EXCITATION-EMISSION MATRIX FLOW CYTOMETRY SYSTEMS AND USES THEREOF

(71) Applicant: SCINTILLON INSTITUTE FOR BIOMEDICAL AND BIOENERGY RESEARCH, San Diego, CA (US)

(72) Inventors: John P. Nolan, La Jolla, CA (US); Danilo Condello, New York, NY (US)

(73) Assignee: SCINTILLON INSTITUTE FOR BIOMEDICAL AND BIOENERGY RESEARCH, San Diego, CA (US)

( * ) Notice: Subject to any disclaimer, the term of this patent is extended or adjusted under 35 U.S.C. 154(b) by 85 days.

(21) Appl. No.: 18/276,617

(22) PCT Filed: Feb. 11, 2022

(86) PCT No.: PCT/US2022/016148
§ 371 (c)(1),
(2) Date: Aug. 9, 2023

(87) PCT Pub. No.: WO2022/174056
PCT Pub. Date: Aug. 18, 2022

(65) Prior Publication Data
US 2024/0167934 A1 May 23, 2024

Related U.S. Application Data

(60) Provisional application No. 63/148,820, filed on Feb. 12, 2021.

(51) Int. Cl.
*G01N 15/1434* (2024.01)
*G01N 15/0205* (2024.01)
(Continued)

(52) U.S. Cl.
CPC ..... *G01N 15/1434* (2013.01); *G01N 15/0211* (2013.01); *G01N 15/14* (2013.01);
(Continued)

(58) Field of Classification Search
CPC .......... G01N 15/1434; G01N 15/0211; G01N 15/14; G01N 15/0205; G01N 15/1429;
(Continued)

(56) References Cited

U.S. PATENT DOCUMENTS 4,078,052 A 3/1978 Papahadjopoulos
4,224,179 A 9/1980 Schneider
(Continued)

FOREIGN PATENT DOCUMENTS

WO 2013181453 A2 12/2013
WO 2016094654 A1 6/2016
(Continued)

OTHER PUBLICATIONS

Belas, et al., Bacterial Bioluminescence: Isolation and Expression of the Luciferase Genes from Vibrio harveyi, Science, vol. 218, 1982, pp. 791-793.
(Continued)

*Primary Examiner* — Tarifur R Chowdhury
*Assistant Examiner* — Carlos Perez-Guzman
(74) *Attorney, Agent, or Firm* — LOZA & LOZA, LLP

(57) ABSTRACT

The technology relates in part to flow cytometry systems and methods of use for the analysis of cells and biological particles.

15 Claims, 23 Drawing Sheets

(51) Int. Cl.

| | |
|---|---|
| *G01N 15/10* | (2024.01) |
| *G01N 15/14* | (2024.01) |
| *G01N 21/64* | (2006.01) |
| *G01N 33/58* | (2006.01) |

(52) U.S. Cl.
CPC ..... *G01N 2015/1006* (2013.01); *G01N 21/64* (2013.01); *G01N 33/58* (2013.01)

(58) Field of Classification Search
CPC .... G01N 15/1459; G01N 21/64; G01N 33/58; G01N 33/585; G01N 2015/1006; G01N 2015/0294; G01N 2015/1497; G01N 2015/1493

See application file for complete search history.

(56) References Cited

U.S. PATENT DOCUMENTS

| | | | |
|---|---|---|---|
| 4,235,871 A | 11/1980 | Papahadjopoulos et al. | |
| 4,308,166 A | 12/1981 | Marchetti et al. | |
| 4,310,506 A | 1/1982 | Baldeschwieler et al. | |
| 4,394,372 A | 7/1983 | Taylor | |
| 4,485,054 A | 11/1984 | Mezei et al. | |
| 4,508,703 A | 4/1985 | Redziniak et al. | |
| 4,522,803 A | 6/1985 | Lenk et al. | |
| 4,573,796 A | 3/1986 | Martin et al. | |
| 5,631,018 A | 5/1997 | Zalipsky et al. | |
| 7,280,204 B2 | 10/2007 | Robinson et al. | |
| 2006/0214112 A1 | 9/2006 | Resch-Genger et al. | |
| 2008/0094627 A1 | 4/2008 | Oldham et al. | |
| 2012/0044480 A1 | 2/2012 | Javadi et al. | |
| 2014/0158913 A1* | 6/2014 | Tanase | G01N 21/6428 356/300 |
| 2016/0003730 A1* | 1/2016 | Schreuder | G01N 15/1484 250/459.1 |
| 2016/0209318 A1* | 7/2016 | Javadi | G01N 15/1434 |
| 2017/0045451 A1* | 2/2017 | Nolan | G01N 15/1429 |
| 2020/0232910 A1* | 7/2020 | Meng | B01L 3/502715 |
| 2020/0292454 A1* | 9/2020 | Li | G01N 21/645 |
| 2022/0244164 A1* | 8/2022 | Nishihara | G01N 15/1427 |

FOREIGN PATENT DOCUMENTS

| | | | |
|---|---|---|---|
| WO | 2020241226 A1 | 12/2020 | |
| WO | 2022174056 A1 | 8/2022 | |

OTHER PUBLICATIONS

De Wet, et al., Firefly Luciferase Gene: Structure and Expression in Mammalian Cells, Molecular and Cellular Biology, vol. 7, No. 2, 1987, pp. 725-737.

Escher, et al., Bacterial luciferase $\alpha\beta$ Fusion Protein is Fully Active as a Monomer and Highly Sensitive in vivo to Elevated Temperature, Proc. Nati. Acad. Sci. USA, vol. 86, 1989, pp. 6528-6532.

Foran, et al., Nucleotide sequence of the LuxA and LuxB genes of the bioluminescent marine bacterium Vibrio fischeni, Nucleic Acids Research, vol. 16, No. 2, 1988, p. 777.

Futamura, et al., Novel Full-Spectral Flow Cytometry with Multiple Spectrally-adjacent Fluorescent Proteins and Fluorochromes and Visualization of in vivo Cellular Movement, Cytometry Part A, vol. 87A, 2015, pp. 830-842.

Grégori, et al., Hyperspectral Cytometry at the Single-Cell Level Using a 32-Channel Photodetector, Cytometry Part A, vol. 81A, 2012, pp. 35-44.

Grégori, et al., Hyperspectral Cytometry, Microbiology and Immunology, vol. 377, 2014, pp. 191-210.

Hoffman, et al., Characterization of Flow Cytometer Instrument Sensitivity, Current Protocols in Cytometry, Supplement 40, Unit 1.20, 2007, 18 pages.

Hoffman, et al., NIST/ISAC Standardization Study: Variability in Assignment of Intensity Values to Fluorescence Standard Beads and in Cross Calibration of Standard Beads to Hard Dyed Beads, Cytometry Part A, vol. 81A, 2012, pp. 785-796.

Holdenrieder, et al., Circulating Nucleosomes in Serum, Annals of the New York Academy of Sciences, vol. 945, 2001, pp. 93-102.

Holdenrieder, et al., Nucleosomes in Serum as a Marker for Cell Death, Clin Chem Lab Med, vol. 39, No. 7, 2001, pp. 595-605.

Holdenrieder, et al., Nucleosomes in Serum of Patients with Benign and Malignant Diseases, Int. J. Cancer (Pred. Oncol.), vol. 95, 2001, pp. 114-120.

Invitation to Pay Additional Fees received for PCT Application No. PCT/US2022/016148, mailed on Apr. 11, 2022, 2 pages.

International Preliminary Report on Patentability received for PCT Application No. PCT/US2022/016148, mailed on Aug. 24, 2023, 11 pages.

International Search Report and Written Opinion received for PCT Application No. PCT/US2022/016148, mailed on Jun. 21, 2022, 14 pages.

Lichtenstein, et al., Circulating Nucleic Acids and Apoptosis, Annals of the New York Academy of Sciences, vol. 945, 2001, pp. 239-249.

Lorenz, et al., Isolation and expression of a cDNA encoding Renilla reniformis luciferase, Proc. Nati. Acad. Sci. USA, vol. 88, No. 10, 1991, pp. 4438-4442.

Nolan, et al., Multiplexed and Microparticle-based Analyses: Quantitative Tools for the Large-Scale Analysis of Biological Systems, International Society for Analytical Cytology, Cytometry Part A, vol. 69A, 2006, pp. 318-325.

Nolan, et al., Spectral Flow Cytometry, Current Protocols in Cytometry, Supplement 63, Unit 1.27, 2013, 13 pages.

Nolan, et al., Visible and Near Infrared Fluorescence Spectral Flow Cytometry, Cytometry Part A, vol. 83A, 2012, pp. 253-264.

Prasher, et al., Primary Structure of the Aequorea victoria Green-fluorescent Protein, Gene, vol. 111, 1992, pp. 229-233.

Prasher, et al., Sequence Comparisons of Complementary DNAs Encoding Aequorin isotypes, Biochemistry, vol. 26, 1987, pp. 1326-1332.

Sanders, et al., Advantages of Full Spectrum Flow Cytometry, Journal of Biomedical Optics, vol. 18, No. 3, Mar. 2013, 9 pages.

Shaner, et al., A Bright Monomeric Green Fluorescent Protein Derived from Branchiostoma lanceolatum, Nature Methods, DOI:10.1038/NMETH.2413, 2013, pp. 1-8.

Stoner, et al., High Sensitivity Flow Cytometry of Membrane Vesicles, Cytometry Part A, vol. 89A, 2015, pp. 196-206.

Wang, et al., Development of Multicolor Flow Cytometry Calibration Standards: Assignment of Equivalent Reference Fluorophores (ERF) Unit, Journal of Research of the National Institute of Standards and Technology, vol. 116, No. 3, 2011, pp. 671-683.

Wang, et al., Quantitating Fluorescence Intensity from Fluorophores: Practical Use of MESF Values, Journal of Research—national Institute of Standards and Technology, vol. 107, No. 4, 2002, pp. 339-353.

Wang, et al., Toward Quantitative Fluorescence Measurements with Multicolor Flow Cytometry, Cytometry Part A, vol. 73A, 2008, pp. 279-288.

* cited by examiner

EXCITATION-EMISSION MATRIX FLOW CYTOMETRY SYSTEMS AND USES THEREOF

RELATED PATENT APPLICATIONS

This patent application is a 35 U.S.C. 371 National Phase Application of International Patent Cooperation Treaty (PCT) Application No. PCT/US2022/016148, filed on Feb. 11, 2022, entitled EXCITATION-EMISSION MATRIX FLOW CYTOMETRY SYSTEMS AND USES THEREOF, naming John P. NOLAN and Danilo CONDELLO as inventors. International PCT Application No. PCT/US2022/016148 claims the benefit of U.S. Provisional Patent Application No. 63/148,820, filed on Feb. 12, 2021, naming John P. NOLAN and Danilo CONDELLO as inventors, entitled EXCITATION-EMISSION MATRIX FLOW CYTOMETRY SYSTEMS AND USES THEREOF. The entire content of each of the foregoing applications is incorporated herein by reference for all purposes, including all text, tables and drawings.

FIELD

The technology relates in part to flow cytometry systems and methods of use for the analysis of cells and biological particles.

BACKGROUND

Measurements of the optical properties of particles (e.g., cells, products of cells, microparticles and nanoparticles) can be useful in many areas including biomedicine, biotechnology, and bioengineering. Flow cytometers using multiple lasers, optical elements such as filters and mirrors, and photodetectors, such as photomultiplier tubes (PMTs) and photodiodes (PDs), often are used for such measurements; they include conventional flow cytometers and spectral flow cytometers.

SUMMARY

Currently available flow cytometry instruments and systems often have deficiencies including low spectral resolution, the inability to analyze single particle data as a hyperspectral/multispectral data set, and low sensitivity. Overcoming these deficiencies often involves complex and expensive instrument design and/or more complicated data analysis. Provided herein is a spectral flow cytometer that provides improved resolution of particle optical properties and the ability to perform hyperspectral/multispectral analyses without a high degree of complexity and/or cost, and associated methodology.

Provided herein in certain aspects are methods for analyzing a particle in a flow cytometer, which includes a) introducing a sample comprising at least one particle to a flow channel containing a plurality of measurement subzones; b) sequentially illuminating the measurement subzones in the flow channel as each particle flows through the flow channel, where each of the measurement subzones is illuminated with a wavelength of light different than for the other measurement subzones, each of the measurement subzones is illuminated when the particle is located therein and each of the measurement subzones is not illuminated when the particle is not located therein, and the particle emits light in response to being illuminated in at least one of the measurement subzones; c) collecting and delivering light emitted by the particle in one or more of the measurement subzones to a detector; and d) detecting light emitted by the particle, thereby analyzing the particle.

Also provided herein in certain aspects are flow cytometry systems, which include a flow channel containing an inlet and an outlet and a plurality of measurement subzones; a fluidics module containing a fluid delivery line to the flow channel inlet and fluid emission line from the flow channel outlet; an illumination module containing a plurality of light sources and a light source synchronizer, where each of the light sources emits light of a different wavelength, and each of the light sources is in communication with a measurement subzone located at a different location in the flow channel; a light collector module in communication with the measurement subzones of the flow channel; a detector module; and a light transmission module connected to the light collector module and the detector module.

Also provided herein in certain aspects are illumination systems containing a plurality of light sources and a light source synchronizer, where each of the light sources emits light of a different wavelength; and each of the light sources is configured for transmission to a measurement subzone located at a different location in a measurement zone.

Also provided herein are kits for use in the methods, flow cytometry systems and/or illumination systems provided herein. As used herein, "a kit" is a packaged set of components and, optionally, includes instructions for use of the components in a method or system.

In certain aspects, analysis of samples (particles) can be facilitated by assays using kits, provided herein, that contain standard particles and reference samples that allow the instrument to be calibrated and measurements to be standardized. As an example, a kit can include standard particles such as antibody capture particles, e.g., beads, that can separately be stained with antibodies labeled with each of the fluorophores to be measured, and these stained particles/beads used to determine the reference spectra of those fluorophores to be used in spectral unmixing, as illustrated in FIG. 11. Further, if the antibody capture particles/beads are also calibrated in terms of antibody binding capacity, then these reference spectra are also calibrated, and the resulting unmixed abundances are reported in calibrated units. Staining ligands other than antibodies can similarly be captured on other, appropriately functionalized, beads.

A kit also can include reference samples that can serve as positive or negative controls in an assay. For example, an assay kit to measure extracellular vesicles can include a reference sample of vesicles that bears certain of the molecular targets to be measured to serve as a positive control, and well as vesicles that lack those targets to serve as a negative control.

A kit also can include protocols for preparing a sample, measuring it on the instrument, and analyzing the acquired data. The protocols can describe the preparation of standard particles, the preparation and staining of reference samples and unknown samples, and the data analysis required for spectral unmixing, calibration, and data analysis and reporting.

Also provided herein are combinations that include: (1) any of the flow cytometry systems or illumination systems provided herein; and (2) any of the kits provided herein. As used herein, "a combination" refers to an association between or among two or more items or elements such as, for example, a flow cytometry system and a kit.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 9 shows the resolution of multi-intensity beads measured from illumination volumes of different wavelengths, without illumination control.

FIG. 10 shows the resolution of multi-intensity beads measured from illumination volumes of different wavelengths, with illumination control.

Figure 1:
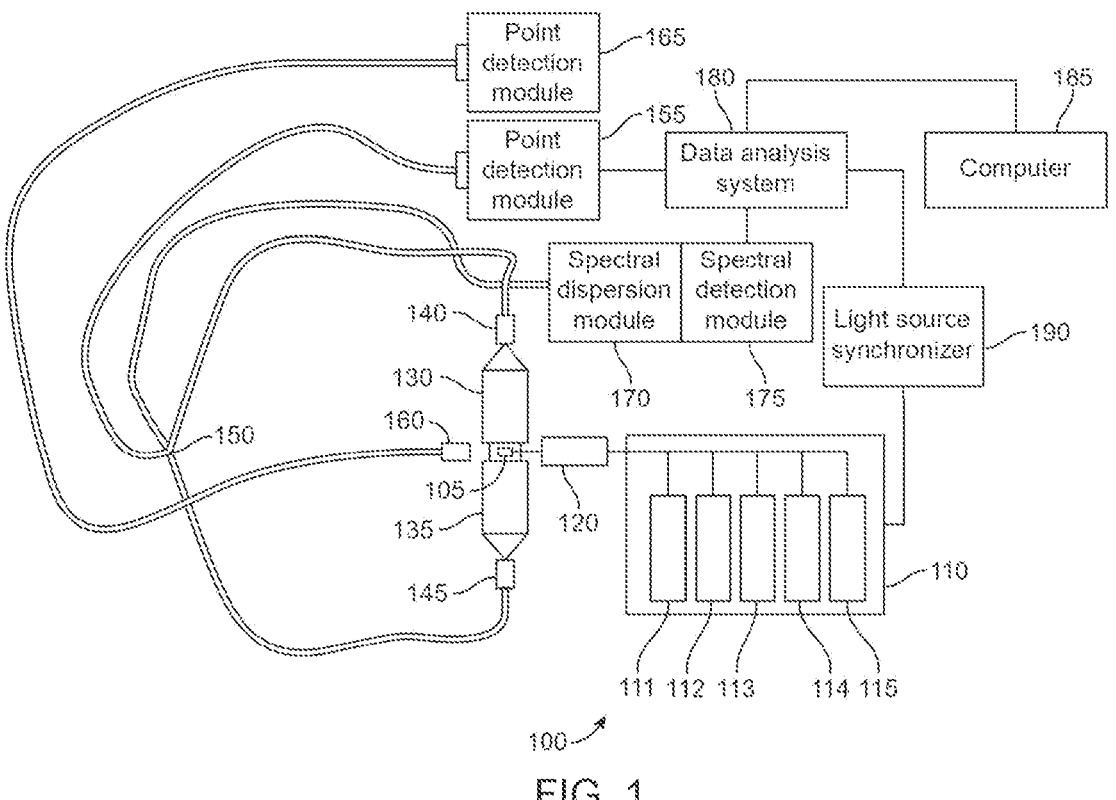
FIG. 1 shows an excitation-emission matrix flow cytometry (EEM FC) system schematic.

Certain features of drawings are described in the following Table:

| Callout | Feature |
|---|---|
| 100 | Excitation-emission matrix flow cytometry (EEM FC) system |
| 105 | Flow channel |
| 106 | Flow channel holder |
| 107 | Flow channel inlet tube |
| 108 | Flow channel outlet tube |
| 110 | Light sources |
| 111 | Source 1 |
| 112 | Source 2 |
| 113 | Source 3 |
| 114 | Source 4 |
| 115 | Source 5 |
| 120 | Beam shaping/focusing optic |
| 130 | First collector |
| 135 | Second collector |
| 140 | First optical fiber array |
| 145 | Second optical fiber array |
| 150 | Merge point |
| 155 | Point detection module |
| 160 | Collection optic |
| 165 | Point detection module |
| 170 | Spectral dispersion module |
| 175 | Spectral detection module |
| 180 | Data analysis system |
| 185 | Computer |
| 190 | Light source synchronizer |
| 200 | Light transmission module (fiber array) configuration A |

-continued

| Callout | Feature |
|---------|---------|
| 210 | Optical fiber array connected to a collection optic (input; cross section view) |
| 211 | Optical fiber i (input) |
| 212 | Optical fiber ii (input) |
| 213 | Optical fiber iii (input) |
| 214 | Optical fiber iv (input) |
| 215 | Optical fiber v (input) |
| 216 | Fiber optic cable housing |
| 220 | Optical fiber array connected to a spectral detector (output; cross section view) |
| 221 | Optical fiber i (output) |
| 222 | Optical fiber ii (output) |
| 223 | Optical fiber iii (output) |
| 224 | Optical fiber iv (output) |
| 225 | Optical fiber v (output) |
| 226 | Fiber optic cable housing |
| 250 | Fiber optic cable plug assembly (input; for connecting to a collection optic) |
| 260 | Fiber optic cable plug assembly (output; for connecting to a spectral detector) |
| 290 | Fiber optic cable |
| 300 | Light transmission module (fiber array) configuration B |
| 310 | Optical fiber array connected to a collection optic (input; cross section view) |
| 311 | Optical fiber i (input) |
| 312 | Optical fiber ii (input) |
| 313 | Optical fiber iii (input) |
| 314 | Optical fiber iv (input) |
| 315 | Optical fiber v (input) |
| 316 | Fiber optic cable housing |
| 320 | Optical fiber connected to a point detector (output; cross section view) |
| 321 | Optical fiber i (output) |
| 326 | Fiber optic cable housing |
| 330 | Optical fiber array connected to a spectral detector (output; cross section view) |
| 331 | Optical fiber ii (output) |
| 332 | Optical fiber iii (output) |
| 333 | Optical fiber iv (output) |
| 334 | Optical fiber v (output) |
| 336 | Fiber optic cable housing |
| 350 | Fiber optic cable plug assembly (input; for connecting to a collection optic) |
| 360 | Fiber optic cable plug assembly (output; for connecting to a point detector) |
| 370 | Fiber optic cable plug assembly (output; for connecting to a spectral detector) |
| 390 | Fiber optic cable |
| 400 | Light transmission module (fiber array) configuration C |
| 410 | Optical fiber array connected to a first collection optic (input; cross section view) |
| 411 | Optical fiber i (input) |
| 412 | Optical fiber ii (input) |
| 413 | Optical fiber iii (input) |
| 414 | Optical fiber iv (input) |
| 415 | Optical fiber v (input) |
| 416 | Fiber optic cable housing |
| 420 | Optical fiber array connected to a second collection optic (input; cross section view) |
| 421 | Optical fiber i' (input) |
| 422 | Optical fiber ii' (input) |
| 423 | Optical fiber iii' (input) |
| 424 | Optical fiber iv' (input) |
| 425 | Optical fiber v' (input) |
| 426 | Fiber optic cable housing |
| 430 | Optical fiber connected to a point detector (output; cross section view) |
| 431 | Optical fiber transmitting combined signal from optical fiber i and optical fiber i' (output) |
| 436 | Fiber optic cable housing |
| 440 | Optical fiber array connected to a spectral detector (output; cross section view) |
| 441 | Optical fiber transmitting combined signal from optical fiber ii and optical fiber ii' (output) |
| 442 | Optical fiber transmitting combined signal from optical fiber iii and optical fiber iii' (output) |
| 443 | Optical fiber transmitting combined signal from optical fiber iv and optical fiber iv' (output) |
| 444 | Optical fiber transmitting combined signal from optical fiber v and optical fiber v' (output) |
| 446 | Fiber optic cable housing |
| 450 | Fiber optic cable plug assembly (input; for connecting to a first collection optic) |
| 460 | Fiber optic cable plug assembly (input; for connecting to a second collection optic) |
| 470 | Fiber optic cable plug assembly (output; for connecting to a point detector) |
| 480 | Fiber optic cable plug assembly (output; for connecting to a spectral detector) |
| 490 | Fiber optic cable |
| 500 | Light transmission module (fiber array) configuration D |
| 510 | Optical fiber array connected to a first collection optic (input; cross section view) |
| 511 | Optical fiber i (input) |
| 512 | Optical fiber ii (input) |

-continued

| Callout | Feature |
|---------|---------|
| 513 | Optical fiber iii (input) |
| 514 | Optical fiber iv (input) |
| 515 | Optical fiber v (input) |
| 516 | Fiber optic cable housing |
| 520 | Optical fiber array connected to a second collection optic (input; cross section view) |
| 521 | Optical fiber i' (input) |
| 522 | Optical fiber ii' (input) |
| 523 | Optical fiber iii' (input) |
| 524 | Optical fiber iv' (input) |
| 525 | Optical fiber v' (input) |
| 526 | Fiber optic cable housing |
| 530 | Optical fiber connected to a point detector (output; cross section view) |
| 531 | Optical fiber transmitting signal from optical fiber i (output) |
| 536 | Fiber optic cable housing |
| 540 | Optical fiber array connected to a spectral detector (output; cross section view) |
| 541 | Optical fiber transmitting signal from optical fiber i' (output) |
| 542 | Optical fiber transmitting combined signal from optical fiber ii and optical fiber ii' (output) |
| 543 | Optical fiber transmitting combined signal from optical fiber iii and optical fiber iii' (output) |
| 544 | Optical fiber transmitting combined signal from optical fiber iv and optical fiber iv' (output) |
| 545 | Optical fiber transmitting combined signal from optical fiber v and optical fiber v' (output) |
| 546 | Fiber optic cable housing |
| 550 | Fiber optic cable plug assembly (input; for connecting to a first collection optic) |
| 560 | Fiber optic cable plug assembly (input; for connecting to a second collection optic) |
| 570 | Fiber optic cable plug assembly (output; for connecting to a point detector) |
| 580 | Fiber optic cable plug assembly (output; for connecting to a spectral detector) |
| 590 | Fiber optic cable |
| 600 | Light transmission module (fiber array) configuration E |
| 610 | Optical fiber array connected to a first collection optic (input; cross section view) |
| 611 | Optical fiber i (input) |
| 612 | Optical fiber ii (input) |
| 613 | Optical fiber iii (input) |
| 614 | Optical fiber iv (input) |
| 615 | Optical fiber v (input) |
| 616 | Fiber optic cable housing |
| 620 | Optical fiber array connected to a second collection optic (input; cross section view) |
| 621 | Optical fiber i' (input) |
| 622 | Optical fiber ii' (input) |
| 623 | Optical fiber iii' (input) |
| 624 | Optical fiber iv' (input) |
| 625 | Optical fiber v' (input) |
| 626 | Fiber optic cable housing |
| 530 | Optical fiber connected to a point detector (output; cross section view) |
| 531 | Optical fiber transmitting signal from optical fiber i (output) |
| 536 | Fiber optic cable housing (interior wall) |
| 537 | Fiber optic cable housing (exterior wall) |
| 640 | Optical fiber array connected to a spectral detector (output; cross section view) |
| 641 | Optical fiber transmitting signal from optical fiber i' (output) |
| 642 | Optical fiber transmitting combined signal from optical fiber ii and optical fiber ii' (output) |
| 643 | Optical fiber transmitting combined signal from optical fiber iii and optical fiber iii' (output) |
| 644 | Optical fiber transmitting combined signal from optical fiber iv and optical fiber iv' (output) |
| 645 | Optical fiber transmitting combined signal from optical fiber v and optical fiber v' (output) |
| 646 | Fiber optic cable housing |
| 650 | Fiber optic cable plug assembly (input; for connecting to a first collection optic) |
| 660 | Fiber optic cable plug assembly (input; for connecting to a second collection optic) |
| 670 | Fiber optic cable plug assembly (output) |
| 690 | Fiber optic cable |
| 700 | Detector module without an intermediate slit |
| 705 | Spectral dispersion module |
| 710 | Fiber input adapter |
| 720 | Collimating lens |
| 730 | Notch filter |
| 740 | Grating |
| 750 | Focusing lens |
| 760 | Detector |
| 765 | Detector adapter |
| 800 | Detector module with an intermediate slit |
| 805 | Spectral dispersion module |

-continued

| Callout | Feature |
|---------|---------|
| 810 | Fiber input adapter |
| 820 | First collimating lens |
| 830 | Notch filter |
| 840 | First focusing lens |
| 850 | Slit |
| 860 | Second collimating lens |
| 870 | Grating |
| 880 | Second focusing lens |
| 890 | Detector |
| 895 | Detector adapter |
| 900 | Data flow schematic |
| 910 | Laser module |
| 911 | Laser 1 control |
| 912 | Laser 2 control |
| 913 | Laser 3 control |
| 920 | Light source synchronizer |
| 921 | Programmable delay line |
| 922 | Logic gate, inverter |
| 930 | Spectral module |
| 935 | Spectral control |
| 936 | Spectral trigger |
| 940 | Spectral data |
| 945 | Computer |
| 950 | Point detector (PD, e.g., photodiode) |
| 955 | Point detector data |
| 960 | Data analysis system (hardware and software) |
| 965 | Micro-processor |
| 966 | FLASH RAM |
| 967 | Universal serial bus (USB) |
| 968 | Digital signal processor (DSP) |
| 969 | Random access memory (RAM) |
| 970 | Analogue to digital converter (ADC) |
| 980 | Photomultiplier tube (PMT) detector assembly |
| 981 | Photomultiplier tube (PMT) 1 |
| 982 | Photomultiplier tube (PMT) 2 |
| 983 | Photomultiplier tube (PMT) 3 |
| 984 | Photomultiplier tube (PMT) 4 |
| 990 | Preamp circuits |
| 991 | Preamp circuit 1 |
| 992 | Preamp circuit 2 |
| 993 | Preamp circuit 3 |
| 994 | Preamp circuit 4 |

DETAILED DESCRIPTION

Described herein are spectral flow cytometers and systems that use high resolution, high sensitivity detector arrays for spectral detection, which can allow for hundreds or thousands of spectral data points, and higher sensitivity due to increased quantum efficiency. Conventional flow cytometers that use point detectors (such as PMTs, photodiodes, or avalanche photodiodes) to measure emission from individual probe volumes in defined bandpass ranges often have low spectral resolution and do not collect or analyze single cell data as a hyperspectral data set. Spectral flow cytometers, which use dispersive optics and array detectors to measure the entire optical spectra of individual particles, have certain advantages compared to traditional flow cytometers which include, for example, improved sensitivity, ease of use, flexibility, and the ability to detect more optical properties of particles (e.g., cells). However, certain spectral flow cytometry instruments are unable to provide high resolution, high sensitivity, hyperspectral single particle analysis.

The use of multiple lasers in spectral flow cytometry offers certain advantages including, for example, improved resolution of particle optical properties. However, use of multiple lasers can present several challenges including, for example, more complex instrument design, a need for multiple detectors, and more complicated data analysis. For example, certain high-resolution spectral flow cytometers can measure sensitive high resolution spectra from individual illumination volumes, but measurement of multiple illumination volumes often requires multiple spectral detection modules (e.g., one for each illumination volume). This can make the system complicated, may not allow for collection and analysis of the data as a hyperspectral data set, and can be very expensive. These challenges can result in compromises in instrument performance and capabilities, and higher costs. Certain lower resolution spectral flow cytometers, which use multianode PMTs, are limited in their spectral resolution (e.g., limited to 32 spectral data points), and are limited in their sensitivity by the quantum efficiency of the PMT, which typically decreases significantly in the red part of the spectrum. Thus, there is a need for a spectral flow cytometer that permits the use of multiple lasers with less cost and complexity.

Provided herein are flow cytometry methods and systems that employ multiple, spatially separated laser beams synchronized to the flow of a particle. In some embodiments, flow cytometry devices herein include a single dispersive optical element and a single array photodetector to produce high resolution multispectral data. In some embodiments, flow cytometry devices herein utilize a single spectral detection module. A single particle optical measurement can produce a single hyperspectral data set that provides advantages for data analysis and resolution of different optical properties of individual particles. Flow cytometry devices herein provide for a simpler and more cost-effective approach, and the synchronized control of laser emission permits the system to detect emissions with significantly lower background signals, resulting in improved sensitivity. Flow cytometry devices herein provide new methods for hyperspectral optical analysis of individual particles that facilitate improved resolution of multiple optical properties of cells, cell products, microparticles, nanoparticles, and other particles.

Excitation-Emission Matrix Flow Cytometry (EEM FC) System

Flow cytometry systems provided herein can be referred to as excitation-emission matrix flow cytometers (EEM FCs) or excitation-emission matrix flow cytometry (EEM FC) systems, and can include one or more of the following components: a flow cell or flow channel in which to present and interrogate a sample; a fluidics module that presents the sample to a measurement zone (i.e., flow channel containing a series of measurement sub-zones); a series of focused light sources that create illumination volumes within the measurement zone; optics to collect the light produced from each illumination volume within the measurement zone; one or more optical fiber arrays to deliver collected light produced from each illumination volume to a detector module; a detector module (e.g., containing a point detection module and/or a spectral dispersion module that spectrally separates the light collected from each focused light source and/or a spectral detection module that measures the spectrally-resolved light produced by each focused light source); and a data analysis system that produces spectral data sets for each particle and analyzes the data sets to determine the properties of individual particles.

Flow cytometry systems provided herein can be operated in one of several modes including a) conventional flow cytometry mode, in which the abundance or type of each analyte, or the abundance or type of each inherent or added probe used to detect and/or quantify the analyte, is determined based on a signal from the analyte and/or probe that is observed within a discrete wavelength range, or channel; in certain aspects, the overlap of analyte and/or probe spectral emission into adjacent channels is accounted for by the process of compensation; and b) spectral mode, in which the spectral data is processed to determine the abundance of each probe. As used herein, an analyte is a sample containing particles that can be analyzed by the systems and methods provided herein. Samples that contain particles for analysis according to the systems and methods provided herein generally include particles in a liquid medium. The particles can be biological, i.e., occurring in nature, or can be synthetic or artificially prepared particles. The particles can be analyzed by detection, identification, quantitation, size or other characterization based on the presence of one or more inherent probes, such as molecular markers associated with the particles, or an exogenously added probe, such as a tag, label, fluorophore or the like, can be used. Any samples containing particles in a liquid can be analyzed according to the methods provided herein.

Figure 6:
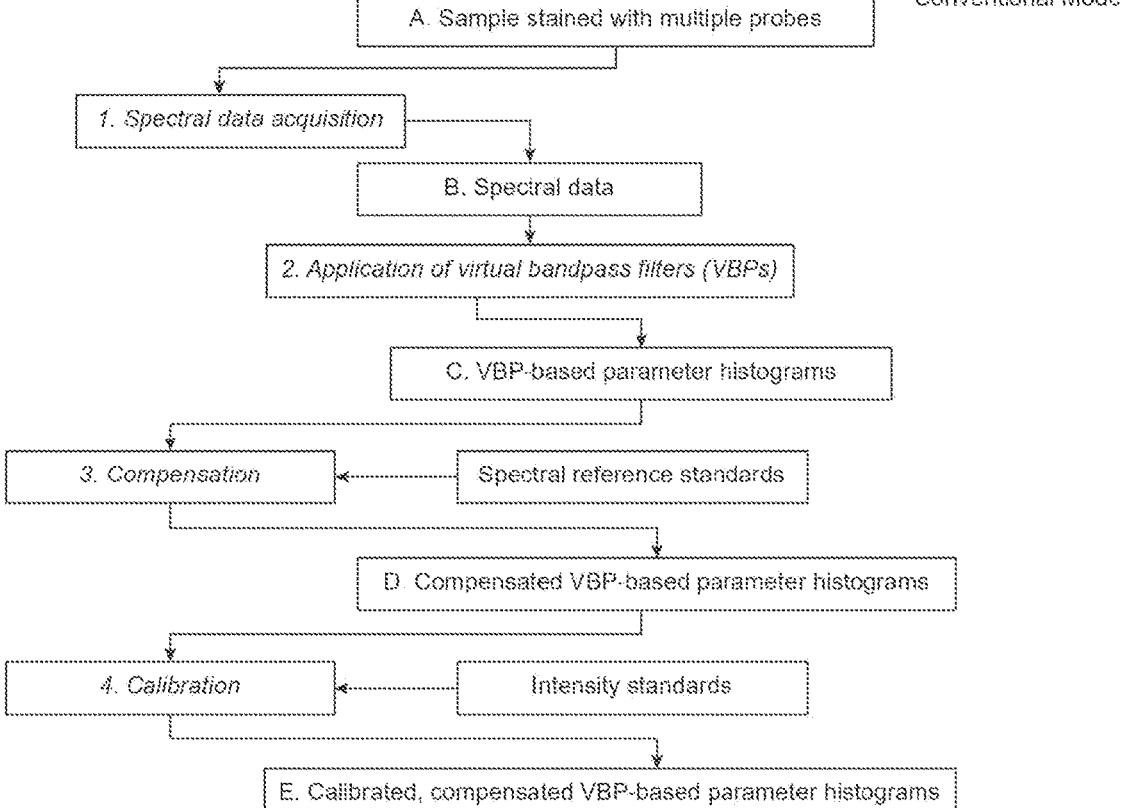
FIG. 6 shows a conventional mode operation.
Figure 7:
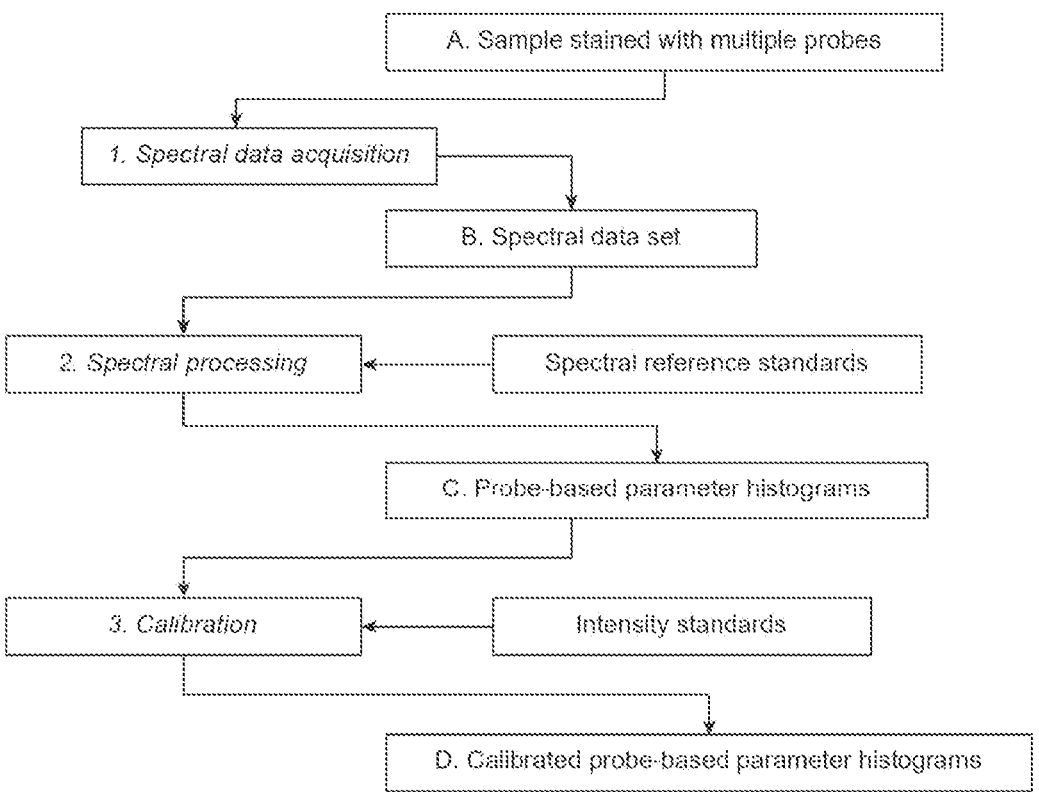
FIG. 7 shows a spectral mode operation.
Figure 8:
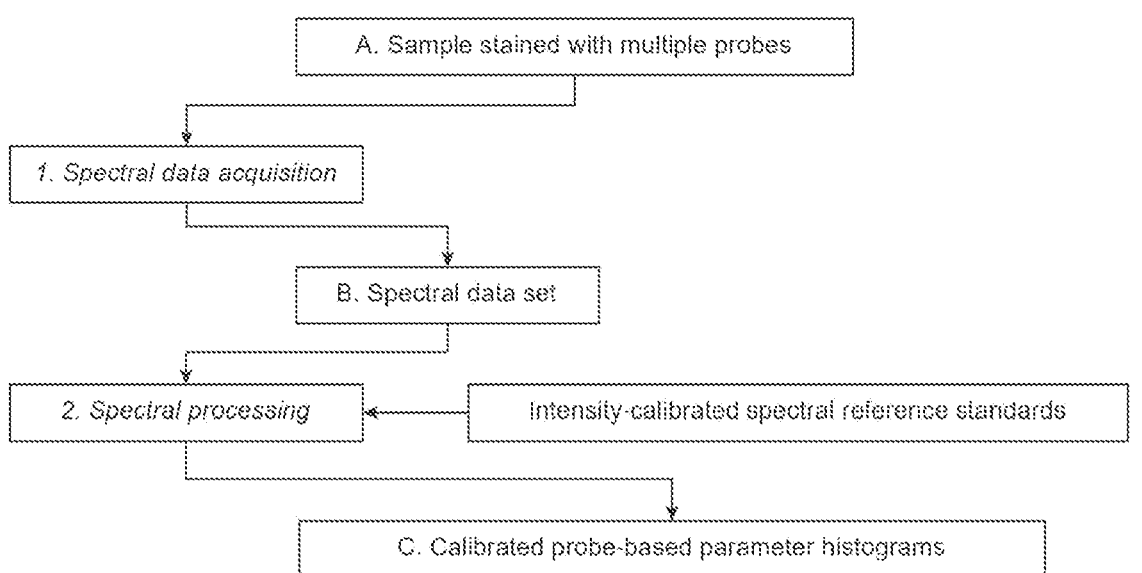
FIG. 8 shows a hyperspectral mode operation.

In conventional flow cytometry, when samples are labeled with multiple different optical probes, the signal from each optical probe generally is detected using a bandpass filter that passes a substantial amount of the light in a discrete wavelength range emitted from that probe upon excitation with a specific laser onto a photodetector such as a photomultiplier tube (PMT) or photodiode (PD), while substantially blocking light from other optical probes. In instances where multiple lasers are used to efficiently excite a greater number of probes, the signals resulting from the laser that most optimally excites a given probe is used for analysis of that probe. The spectral particle analyzer can mimic conventional flow cytometry by operating in conventional mode (FIG. 6) by summing the signal that falls within a discrete wavelength range, or virtual bandpass (VBP), as a result of excitation by a particular laser to produce VBP-based intensity histograms. In practice, some light from other probes will also fall within the discrete wavelength range assigned to a given optical probe, a phenomenon often referred to as spectral spillover. This spillover signal can be measured using a set of particles stained with one of each different optical probe and is generally accounted for by a mathematical process called compensation, which can also be performed on VBP histograms. The intensities represented in VBP histograms can also be calibrated in absolute units referenced to an external standard, for example mean-equivalent soluble fluorochromes (MESF) or equivalent reference fluorochromes (ERF), using appropriately calibrated particles.

Spectral flow cytometry can offer advantages over conventional flow cytometry, for example, by applying spectral processing methods to the single particle spectral data. In spectral mode, the entire emission spectra excited by multiple probes is collected and the signal from each optical probe can be determined by spectral unmixing, a spectral processing method that uses the known spectra of each probe to estimate the contribution of each to the single particle mixture spectra. Spectral unmixing of spectral flow cytometry data produces intensity histograms for each optical probe. These intensities can be calibrated in absolute units (MESF, ERF, or other) as for conventional mode flow cytometry. Other spectral processing methods include classification, and unsupervised analysis approaches including principle components analysis (PCA).

Provided herein are flow cytometry systems capable of multi-parameter single particle analysis. In flow cytometry, as used herein, several terms can be used to refer to multi-parameter single particle analysis. For example, when signals from around 2 to 4 different fluorophores are measured on different detectors, this can be referred to as multi-color flow cytometry. In another example, when multi-laser instruments measure around 12 to 15 fluorophores, this can be referred to as polychromatic flow cytometry to reflect the higher number of "colors" detected. The term "spectral flow cytometry" can be used to refer to instruments that measure the complete spectra of individual particles using a single array detector, rather than using a different point detector (such as a photomultiplier tube (PMT), photodiode (PD), or avalanche photodiode (APD)) for each color.

The terms multispectral flow cytometry and hyperspectral flow cytometry, used interchangeably herein, generally are applied to describe the simultaneous detection of about 10 or >100 bands across an emission spectrum. In spectroscopy, an approach termed excitation-emission matrix (EEM) spectroscopy considers both the excitation and emission spectra of a sample. Such measurements have not previously been reported using flow cytometry because conventional flow cytometry systems typically are not capable of such measurements. Provided herein is a system, referred to herein as an excitation-emission matrix flow cytometer (EEM FC) or an excitation-emission matrix flow cytometry (EEM FC) system, which can simultaneously sample the entire emission spectra at multiple excitation wavelengths. In certain instances, increased information about particle optical properties can lead to improved estimates of the optical probes associated with a particle and their abundance, as well as improved understanding of the signals from intrinsic auto-fluorescence.

A non-limiting example of an EEM FC system is provided in FIG. 1. One embodiment of an EEM FC system is illustrated as system 100. Certain components of the system can be associated with and/or in connection with one or more other components. Components associated with each other can be physically connected (i.e., directly or indi-rectly), or, in certain embodiments, not be physically con-nected. Components associated with each other can be located in close proximity to each other in the system. Components in connection with each other generally are physically connected (i.e., directly or indirectly). Compo-nents can be arranged such that one component is in com-munication with another component. In some configura-tions, components can be arranged such that a signal can pass between one component and another component. In some configurations, components can be arranged such that light can pass between one component and another compo-nent. The system 100 in FIG. 1 contains a plurality of light sources. One embodiment of a plurality of light sources is illustrated as component 110, which includes light source 1 111 (e.g., laser 1, 405 nm), light source 2 112 (e.g., laser 2, 473 nm), light source 3 113 (e.g., laser 3, 488 nm), light source 4 114 (e.g., laser 4, 532 nm), and light source 5 115 (e.g., laser 5, 638 nm). The system can include a beam shaping/focusing optic 120 associated with a flow channel 105 (e.g., a flow channel in a flow cell). A flow channel 105 is in connection with a first collector 130 and a second collector 135. A first collector 130 and a second collector 135 are in connection with a first optical array 140 and a second optical array 145, respectively. A first optical array 140 and a second optical array 145 merge at a merge point 150 (e.g., a merge point for the first optical array and the second optical array), and are in connection with a point detection module 155 (e.g., containing a selective optical element and a point detector) and a spectral dispersion module 170. A spectral dispersion module 170 is in connec-tion with a spectral detection module 175. A point detection module 155 and a spectral detection module 175 are in connection with a data analysis system 180, which is in connection with a computer 185 and a light source synchro-nizer 190. A light source synchronizer 190 is in connection with a plurality of light sources 110.

A flow channel 105 also is in connection with a collection optic 160. In certain embodiments, a collection optic 160 can be a forward angle light scatter (FALS) collection option, which can be used to measure particle light scatter. The FALS scatter can provide information about, e.g., particle size, shape, and refractive index, which can be useful for particle analysis applications. A collection optic 160 is in connection with a point detection module 165 (e.g., containing a selective optical element and a point detector).

An EEM FC system herein can contain one or more of the following components: flow cell/flow channel, fluidics mod-ule, illumination module (e.g., containing light sources and a light source synchronizer), light collector module (e.g., containing one or more collection optics), light transmission module, detector module, and data analysis system, each of which is described in detail below.

Flow Cell

An EEM FC system provided herein can contain a flow cell. A flow cell generally refers to a structure through which a liquid stream carries particles. A flow cell can be mounted within a holder that provides fluidic input for sample fluids and a fluidic output for waste. A flow cell can include inlet tubes (e.g., sample inlet, sheath inlet) and outlet tubes (e.g., sheath outlet); and the sheath and sample inlet tubes may be connected to a fluidics module, as described below. A flow cell can include one or more flow channels, and the terms flow cell and flow channel are, in certain aspects, used interchangeably herein. A flow channel can include an inlet (e.g., for sample input) and an outlet (e.g., for waste output). A flow channel can be a structure (e.g., a rectangular-shaped cuvette) made of optically transparent material (e.g., quartz, glass, plastic). Other types of flow channels include channels with square, triangular, or round cross sections; and flow channels constructed in microfabricated and microfluidics devices. Often, particles are hydrodynamically aligned so that they pass single file through the flow channel. For example, particles can be confined to the center of a flowing stream of fluid by hydrodynamic focusing using a sheath fluid. Particles can also flow in a stream of fluid without use of a sheath. The fluid can transport particles through a measurement zone. A measurement zone generally refers to a section of a flow channel where particles are illuminated. A measurement zone can also be referred to as a measure-ment volume, a sensing zone, a sensing volume, an inter-rogation zone, an interrogation volume, a probe zone, a probe volume, or an observation region. In some embodi-ments, measurements can be taken external to a flow chan-nel, including in a stream, in air or on a substrate.

A measurement zone in a flow channel can include a plurality of measurement subzones. Measurement subzones can be disposed at discrete positions in a flow channel. Discrete positions in a flow channel can refer to measure-ment subzone midpoints that are not located at the same position in a flow channel. Measurement subzones can be adjacent to each other (e.g., directly abutting each other) and/or can be disposed in a flow channel such that non-measurement zone spaces are located between measurement subzones. Measurement subzones can, in certain aspects, be disposed linearly in the direction of fluid flow in the flow channel. A measurement subzone can also be referred to as a measurement subvolume, a sensing subzone, a sensing subvolume, an interrogation subzone, an interrogation sub-volume, a probe subzone, a probe subvolume, or an obser-vation subregion.

Each measurement subzone can correspond to a portion of the measurement zone that is illuminated by a particular focused light source. As an example, measurement subzone A corresponds to a portion of the measurement zone illu-minated by focused light source A, measurement subzone B corresponds to a portion of the measurement zone illumi-nated by focused light source B, and measurement subzone C corresponds to a portion of the measurement zone illu-minated by focused light source C. A measurement subzone may be referred to as a measurement sub-volume, a sensing subzone, a sensing sub-volume, an interrogation subzone, an interrogation sub-volume, a probe subzone, a probe sub-volume, or an observation sub-region. In some embodi-ments, a measurement zone contains between 2 to 20 measurement subzones. For example, a measurement zone can contain 2, 3, 4, 5, 6, 7, 8, 9, 10, 11, 12, 13, 14, 15, 16, 17, 18, 19, or 20 measurement subzones. In some embodi-ments, a measurement zone contains 3 measurement sub-zones. In some embodiments, a measurement zone contains 4 measurement subzones. In some embodiments, a measure-ment zone contains 5 measurement subzones. In some embodiments, a measurement zone contains 6 measurement subzones. In certain embodiments, the measurement sub-zones are illuminated in a strobed manner, e.g., each mea-surement subzone is illuminated sequentially to coincide with the presence, in each subzone, of a particle being analyzed from the analyte/sample of interest, and the illumination in each measurement subzone is turned off sequentially as the particle being analyzed from the analyte/sample of interest leaves that measurement subzone.

Once a measurement subzone is illuminated (e.g., by a focused light source), the space can be referred to as an illumination volume or an illumination zone. Illumination of the measurement subzones can, in certain embodiments, be applied in a strobed manner to coincide with entry and exit of each particle to be analyzed in a given measurement subzone. In some embodiments, between 2 to 20 illumination volumes are generated upon illumination of the corresponding measurement subzones. For example, 2, 3, 4, 5, 6, 7, 8, 9, 10, 11, 12, 13, 14, 15, 16, 17, 18, 19, or 20 illumination volumes can be generated upon illumination of the corresponding measurement subzones. In some embodiments, 3 illumination volumes are generated upon illumination of the corresponding 3 measurement subzones. In some embodiments, 4 illumination volumes are generated upon illumination of the corresponding 4 measurement subzones. In some embodiments, 5 illumination volumes are generated upon illumination of the corresponding 5 measurement subzones. In some embodiments, 6 illumination volumes are generated upon illumination of the corresponding 6 measurement subzones.

Fluidics Module

An EEM FC system herein can include a fluidics module. A fluidics module can be referred to as a fluidics system, and can include a fluid delivery line to the flow channel inlet and fluid emission line from the flow channel outlet. For example, sample aspirated from a sample tube into a sample loop can be delivered via a sample inlet tube to a flow cell, where the sample stream is hydrodynamically focused in the flow cell. Samples can pass through a measurement zone where one or more focused light sources create illumination volumes at each measurement subzone within the sample stream, and collection optics collect and focus light emitted from each illumination volume into an optical fiber contained in a linear fiber array.

A representative fluidics module can include a set of computer-controlled pumps and valves connected via tubing. Pumps can be used for the delivery of sheath and sample to a flow cell via sheath lines, sample lines, and/or sample loops made of tubing. A multiport valve and a switching valve can connect sheath lines, sample lines, and sample loops. In some embodiments, control scripts can control the pumps and valves to execute certain routines including sample load, sample run, and/or sample flush.

Illumination Module

An EEM FC system herein can include an illumination module. An illumination module is described below in the context of an EEM FC system herein, although an illumination module can be useful for systems other than an EEM FC system herein (e.g., for imaging applications and other applications). An illumination module provided herein is for use in a variety of applications and can be referred to as an illumination system.

An illumination module can be configured to sequentially generate a plurality of illumination volumes when measurement subzones are sequentially illuminated. An illumination module can include one or more light sources. An illumination module can include a light delivery module. An illumination module can include a light source synchronizer. An illumination module can include a plurality of light sources, a light delivery module, and a light source synchronizer, each of which is described below.

Light Sources

An illumination module can include one or more light sources. Typically, an illumination module provided herein includes a plurality of light sources. In some embodiments, each of the light sources in a plurality of light sources emits light of a different wavelength. In some embodiments, each light source is in communication with a measurement subzone, where each measurement subzone is located at a different location in a flow channel. In some embodiments, an illumination module contains between about 2 to 20 light sources. For example, an illumination module can contain 2, 3, 4, 5, 6, 7, 8, 9, 10, 11, 12, 13, 14, 15, 16, 17, 18, 19, or 20 light sources. In some embodiments, an illumination module contains 3 light sources. In some embodiments, an illumination module contains 4 light sources. In some embodiments, an illumination module contains 5 light sources. In some embodiments, an illumination module contains 6 light sources.

A light source can include any light source suitable for excitation of a target. For example, a light source can include a laser or light emitting diode (LED). A laser can have a multiple number of excitation wavelengths or a single wavelength. A laser can include a gas laser, solid-state laser, semiconductor diode laser, or dye laser. A light source can include a combination of semiconductor diode lasers of any wavelength with each diode having a different wavelength, for example. In certain instances, a band-pass filter can be placed in front of a laser. If a laser produces more than one line, the unwanted line can be filtered out before it reaches the target.

In some embodiments, a plurality of light sources includes a plurality of lasers, where each laser emits a different wavelength. In some embodiments, a plurality of light sources contains a plurality of lasers, where each laser emits a different wavelength between about 200 nm to about 1200 nm. In some embodiments, a plurality of light sources includes a plurality of lasers, where each laser emits a different wavelength between about 200 nm to about 1200 nm. In some embodiments, a plurality of light sources includes between about 2 to 20 lasers. For example, a plurality of light sources can include 2, 3, 4, 5, 6, 7, 8, 9, 10, 11, 12, 13, 14, 15, 16, 17, 18, 19, or 20 lasers. In some embodiments, a plurality of light sources includes 3 lasers. In some embodiments, a plurality of light sources includes 4 lasers. In some embodiments, a plurality of light sources includes 5 lasers. In some embodiments, a plurality of light sources includes 6 lasers.

Illumination volumes within a measurement zone can be formed by a focused light from each of a plurality of light sources. A representative focused light source includes a series of lasers (e.g., in an integrated laser module) whose beams are focused to a series of spots (measurement subzones) along a flow cell or flow channel using beam shaping optics. Beam shaping optics can include, but are not limited to, spherical optics, crossed cylindrical optics, a Powell lens, or other optical element to produce illumination zones with spherical, elliptical, rectangular or "top-hat" structured or other structured illumination features. Light sources can be positioned at measured intervals along a flow cell or flow channel. For example, light sources can be positioned at measured intervals along the center of a flow channel's long axis. In some configurations, light sources are positioned at about 10 μm to about 200 μm intervals. For example, light sources can be positioned at about 20 μm, 50 μm, 100 μm, or 150 μm intervals. In some embodiments, light sources are positioned at about 100 μm intervals. An interval, as used herein, can be defined as the space between centers of elliptical focus profiles for each laser. Elliptical focus profiles can be of dimensions ranging from 5 μm×20 μm to 20 μm×100 μm. In some embodiments, elliptical focus profiles range from 8 μm×30 μm to 15 μm×80 μm. In certain embodiments, focus profiles can have spherical, rectangular, "top hat" structured or other structured features.

In one configuration, light sources include three lasers whose beams are passed through focusing and shaping optics to produce three illumination volumes. In one configuration, light sources include four lasers whose beams are passed through focusing and shaping optics to produce four illumination volumes. In one configuration, light sources include five lasers whose beams are passed through focusing and shaping optics to produce five illumination volumes. In one configuration, light sources include six lasers whose beams are passed through focusing and shaping optics to produce six illumination volumes. For the above configurations and other configurations, each laser can have an elliptical focus profile of dimensions ranging from 8 μm×30 μm to 15 μm×80 μm, with the profile centers spaced 100 μm apart along the long axis of a flow channel. For the above configurations and other configurations, output of the lasers can be controlled in time by a light source synchronizer described below, which turns each laser on only when a particle is flowing through its corresponding measurement subzone.

Light Delivery Module

An illumination module can include a light delivery module. A light delivery module can be connected to one or more light sources and a flow channel. A light delivery module can include an optical fiber or plurality of optical fibers (e.g., fiber optic cables, optical fiber cables). A light delivery module can include a shaping optic, or a focusing optic, or a shaping optic and focusing optic (e.g., for directing/focusing light from one or more light sources to one or more measurement subzones in a flow channel to form one or more illumination volumes).

Light Source Synchronizer

An illumination module can include a light source synchronizer. A light source synchronizer can be referred to as an illumination controller or an illumination control module. A light source synchronizer can include one or more of the following components: a printed circuit board bearing a logic gate and inverter, a programmable integrated circuit delay line, one or more or a series of resistors, and a potentiometer. A light source synchronizer can receive input from a component of the EEM FC system (e.g., from a data analysis system) at the start of a measurement sequence and can send output to a light source or plurality of light sources (e.g., integrated laser module) to control the output of the individual light sources (e.g., lasers).

A light source synchronizer can be configured to sequentially illuminate a plurality of measurement subzones in a flow channel as a particle (e.g., a particle in a sample) flows through the flow channel. A light source synchronizer can be configured to illuminate a measurement subzone when a particle is present in that subzone. A light source synchronizer can be configured to not illuminate a measurement subzone when a particle is not present in that subzone. In some embodiments, a light source synchronizer is configured to sequentially activate and deactivate a plurality of light sources, where each of the light sources illuminates a different measurement subzone. For example, a light source synchronizer can be configured to sequentially activate one of the light sources after deactivating one of the other light sources.

In one configuration, a light source synchronizer can be configured to (i) activate a light source that illuminates a measurement subzone, while all other light sources are deactivated; (ii) deactivate the light source that illuminates the measurement subzone illuminated in (i) and activate a light source that illuminates a measurement subzone located next to the measurement subzone illuminated in (i) and closer to an outlet in the flow channel, while all other light sources are deactivated, and (iii) repeating (i) and (ii) until a light source that illuminates a measurement subzone closest to the flow channel outlet is activated and then deactivated.

In some embodiments, a light source synchronizer can include a plurality of switches. Switches can be analog and/or digital switches coupled to one or more light sources. In some configurations, each of the switches is in separate communication with each of the light sources. Generally, the term separate communication refers to one switch connected to and operating one light source. In some embodiments, each of the switches is configured to activate and deactivate each of the light sources in a plurality of light sources. In some embodiments, each of the switches is configured to activate each of the light sources in a plurality of light sources one at a time while each of the other light sources is deactivated.

In some embodiments, a light source synchronizer can include a controller. In some embodiments, a controller in a light source synchronizer is configured to activate and deactivate a plurality of switches. In some embodiments, a controller in a light source synchronizer is configured to sequentially activate and deactivate each of the light sources. In some embodiments, a controller in a light source synchronizer is configured to (i) activate and deactivate each of the switches, and (ii) activate each of the light sources one at a time while each of the other light sources is deactivated (e.g., in a strobed manner, as a particle enters (activate) and exits (deactivate) an illumination zone of a light source). In some embodiments, a controller in a light source synchronizer is configured to sequentially activate one of the light sources after deactivating one of the other light sources, e.g., for strobed illumination of particle(s) in a sample. Generally, as used herein, the term sequentially activate refers to illumination of each measurement subzone for a defined time period, where the defined time periods of illumination of each measurement subzone do not overlap and are serially coincident with the passage of a particle through each measurement subzone. In some embodiments, a controller in a light source synchronizer is configured to (i) activate a light source that illuminates a measurement subzone, while all other light sources are deactivated; (ii) deactivate the light source that illuminates the measurement subzone illuminated in (i) and activate a light source that illuminates a measurement subzone located next to the measurement subzone illuminated in (i) and closer to the flow channel outlet, while all other light sources are deactivated, and (iii) repeat (i) and (ii) until a light source that illuminates a measurement subzone closest to the flow channel outlet is activated and then deactivated.

In some embodiments, a light source synchronizer can be configured to activate an illumination sequence when the system is triggered. For example, the presence of a particle in a particular measurement subzone (e.g., trigger subzone) can trigger the system. In some embodiments, a trigger subzone can be a measurement subzone located closest to an inlet in the flow channel. Thus, in some embodiments, a trigger subzone can be the first measurement subzone through which a particle passes. In some embodiments, a light source synchronizer is configured to detect the presence of a particle in a measurement subzone closest to an inlet in the flow channel, and transmit a signal to sequentially activate and deactivate light sources. For example, an illumination module can be in connection with a gate configured to (i) detect the presence of a particle in a measurement subzone closest to a flow channel inlet, and (ii) transmit a signal to a controller in a light source synchronizer to sequentially activate and deactivate light sources. In some embodiments, a light source directed to a trigger subzone remains on during an EEM FC system's default state and turns off when a particle is detected in the trigger subzone.

In some embodiments, a light source synchronizer can be configured to activate and deactivate each light source according to a measured or predicted rate of transit (e.g., time it takes for a particle to traverse one or more measurement subzones and/or time it takes for a particle to pass between measurement subzones). The rate of transit can depend on factors such as physical properties of a particle (e.g., mass, shape) and velocity of the fluid passing through a flow channel. The fluid velocity can be controlled by pumps in a fluidics module. In some embodiments, the rate of transit can be determined prior to activation of an illumination sequence. In some embodiments, an EEM FC system herein includes a detector to determine rate of transit prior to activation of an illumination sequence. In some embodiments, an EEM FC system herein includes an intermediate circuit board for regulating light source activation/deactivation timing (e.g., according to rate of transit).

In one configuration of an EEM FC system herein, the default state for the system is a first, triggering laser is on and all other lasers are off. When a component of the EEM FC system (e.g., data analysis system) detects a pulse from a trigger channel (e.g., detects the presence of a particle in the trigger subzone or first measurement subzone), a signal is sent to the light source synchronizer to initiate a sequence in which:

a) after a first delay time, set to the period of time estimated for the particle to transit its measurement subzone (e.g., trigger subzone), a signal is sent to the integrated laser module to turn OFF the first laser for a time estimated for the particle to transit the final measurement subzone in the measurement zone. The first delay time can be, for example, from less than 1 μsec (microsecond) to greater than 1 msec (millisecond), e.g., about 0.1, 0.2, 0.3, 0.4 0.5 or more μsec to about 2, 3, 4, 5, 6, 7, 8, 9, 10 or more msec. In certain embodiments, the first delay time can be from about 0.1 μsec to about 10 msec;

b) after a second delay time, set to when the particle is estimated to enter a second measurement subzone, a signal is sent to the integrated laser module to turn ON the second laser for a period of time estimated for the particle to transit the second measurement subzone and then to turn the second laser OFF;

c) after a third delay time, set to when the particle is estimated to enter a third measurement subzone, a signal is sent to the integrated laser module to turn ON the third laser for a period of time estimated for the particle to transit the third measurement subzone and then to turn the third laser OFF;

d) for systems that include additional measurement subzones, additional lasers can be activated by repeating step c; and e) at the end of the sequence, when the particle exits the final measurement subzone, the first triggering laser is turned back ON and the system is returned to the default state, ready for the detection of another particle.

For EEM FC systems herein, light source synchronizers and activation/deactivation sequences can be modified to include larger numbers of lasers and/or various delay times to accommodate certain particle types, operating conditions, and/or experimental designs. Delay times can be set to correspond to the transit of particles between and through measurement subzones, which in turn can depend on the speed of the particles and the distance between subzones. In general, the transit times through the measurement subzones and between the measurement subzones can be determined by inspection of the resulting signal pulses, either manually with the assistance of an oscilloscope, or automatically with computational analysis of the signal pulses.

In certain embodiments, there are 5 measurement subzones, each about or at 10 um in height and spaced about or at 100 um apart, center to center. For example, for samples traveling at a linear velocity of approximately 1 meter/second between measurement subzones, approximately 10 micrometers in height and spaced approximately 100 micrometers apart, the transit time through a subzone would be approximately 10 microseconds, the transit time between measurement subzones would be approximately 100 microseconds, and the time to transit the distance from a first measurement subzone to a fifth measurement subzone would be approximately 400 microseconds. In such an example, the timing sequence for the light source synchronizer would be:

| Phase | Transit time (usec) | Laser 1 | Laser 2 | Laser 3 | Laser 4 | Laser 5 | Total time (usec) | | Delay Time (usec) |
|---|---|---|---|---|---|---|---|---|---|
| Ready state | | ON | OFF | OFF | OFF | OFF | | | |
| Subzone 1 transit time | 10 | ON | OFF | OFF | OFF | OFF | 10 | Delay Time 1 | 10 |
| Interzone transit time | 90 | OFF | OFF | OFF | OFF | OFF | 100 | Delay Time 2 | 100 |
| Subzone 2 transit time | 10 | OFF | ON | OFF | OFF | OFF | 110 | | |
| Interzone transit time | 90 | OFF | OFF | OFF | OFF | OFF | 200 | Delay Time 3 | 200 |
| Subzone 3 transit time | 10 | OFF | OFF | ON | OFF | OFF | 210 | | |
| Interzone transit time | 90 | OFF | OFF | OFF | OFF | OFF | 300 | Delay Time 4 | 300 |
| Subzone 4 transit time | 10 | OFF | OFF | OFF | ON | OFF | 310 | | |
| Interzone transit time | 90 | OFF | OFF | OFF | OFF | OFF | 400 | Delay Time 5 | 400 |
| Subzone 5 transit time | 10 | OFF | OFF | OFF | OFF | ON | 410 | | |
| Ready state | | ON | OFF | OFF | OFF | OFF | | | |

In certain embodiments, a light source synchronizer is part of, is connected to, and/or is in communication with a data analysis system, described in further detail below.

Light Collector Module

An EEM FC system herein can include a light collector module. A light collector module can include one or more collectors. Collector, as used herein, can be referred to as collection optics. A light collector module can be in connection with one or more measurement subzones in a flow channel. Light emitted from one or more illumination volumes (i.e., from one or more illuminated measurement subzones in a flow channel) can be collected by a collector coupled to a flow cell. In some embodiments, light emitted from one or more illumination volumes (i.e., from one or more illuminated measurement subzones in a flow channel) can be collected by two collectors coupled to a flow cell. In some configurations, collectors are placed on opposite sides of a flow cell (e.g., on both wide faces of a flow cell) to collect light from both sides of a measurement zone or subzone.

In some embodiments, a collector module includes one or more composite signal output collectors. In some embodiments, a collector module includes a collector positioned parallel to the direction of light emitted from the light sources. In some embodiments, a collector module includes a collector orthogonal to the direction of light emitted from the light sources. In some embodiments, a collector module includes a collector located at a position proximal to the flow channel. In some embodiments, a collector module includes a collector located at a position distal to the flow channel. In some embodiments, a collector module includes a collector located at a position proximal to the flow channel, and includes a collector located at a position distal to the flow channel. In some embodiments, a collector module includes at least two collectors. For example, a collector module can include two collectors positioned orthogonal to the direction of light emitted by the light sources, opposite to one another, and proximal to the flow channel and distal to the flow channel.

Collection optics can be designed to image, with high resolution over a wavelength range from less than about 300 nm to greater than about 1400 nm, for example between less than or about 200, 250, 300, 350, 400, 450 or 500 nm to about or greater than 600, 650, 700, 750, 800, 850, 900, 950, 1000, 1050, 1100, 1150, 1200, 1250, 1300, 1350, 1400 or more nm, light from a series of illumination volumes in the measurement zone onto a custom-fabricated array of optical fibers. In some embodiments, the magnification, focal length, and numerical aperture of the optic match the desired height and spacing of the illumination volumes in the measurement zone to the numerical aperture, diameter, and spacing of the optical fibers in the fiber array. For example, the magnification (about 3.2×), focal length (about 40 mm), and numerical aperture (about 1.0) of the optic can match the desired height (about 5-20 μm) and spacing (about 100 μm, center to center) of the illumination volumes in the measurement zone to the numerical aperture (about 0.28), diameter (about 270 um), and spacing (about 320 μm, center to center) of the optical fibers in the fiber array.

Light Transmission Module

An EEM FC system herein can include a light transmission module. A light transmission module can be connected to a light collector module and a detector module. A light transmission module can be configured to deliver light from a light collector module to a detector module. In some embodiments, a light transmission module can be configured to deliver light from a light collector module to a selective optical element in a detector module. In some embodiments, a light transmission module can be configured to deliver light from a light collector module to a dispersive optical element in a detector module. In some embodiments, a light transmission module can be configured to deliver light from a light collector module to a selective optical element and to a dispersive optical element in a detector module.

A light transmission module can be configured to deliver light from two collectors (i.e., in a light collector module) to a detector module. In some embodiments, a light transmission module can be configured to deliver light from two collectors to a selective optical element in a detector module. In some embodiments, a light transmission module can be configured to deliver light from two collectors to a dispersive optical element in a detector module. In some embodiments, a light transmission module can be configured to deliver light from two collectors to a selective optical element and to a dispersive optical element in a detector module.

In some embodiments, a light transmission module is configured to combine light from two collectors. For example, a first optical fiber from a first collector can fuse or intersect with a second optical fiber from a second collector to form a single fiber for transmitting a combined signal to a detector module. In some instances, a combined signal is more intense than each of the individual signals. In some embodiments, a light transmission module is configured to combine light from two collectors and deliver the combined light from the two collectors to a selective optical element in a detector module. In some embodiments, a light transmission module is configured to combine light from two collectors and deliver the combined light from the two collectors to a dispersive optical element in a detector module. In some embodiments, a light transmission module is configured to combine light from two collectors and deliver the combined light from the two collectors to a selective optical element and to a dispersive optical element in a detector module. In some embodiments, a light transmission module can be configured to 1) deliver light emitted from the measurement subzone closest to a flow channel inlet obtained from two collectors to a selective optical element; and 2) deliver light emitted from the remaining measurement subzones obtained from both collectors to a dispersive optical element. In some embodiments, a light transmission module can be configured to 1) deliver light emitted from the measurement subzone closest to a flow channel inlet obtained from a first collector module to a selective optical element; and 2) deliver light emitted from some or all measurement subzones obtained from a second collector module to a dispersive optical element. In some embodiments, a light transmission module may be configured to 1) deliver light emitted from the measurement subzone closest to a flow channel inlet obtained from a first collector module to a selective optical element; 2) deliver light emitted from the remaining measurement subzones obtained from the first collector to a dispersive optical element; and 3) deliver light emitted from some or all measurement subzones obtained from a second collector module to the dispersive optical element.

A light transmission module can include one optical fiber or a plurality of optical fibers (e.g., fiber optic cables, optical fiber cables, multimode optical fibers). In some configurations, a light transmission module contains one or more optical fiber arrays. An optical fiber array can be configured to deliver light to a detector module (e.g., point detection module and/or a spectral detection module in a detector module), and can be designed and fabricated to accommodate various operating conditions and experimental designs. In one configuration, light from one side of a measurement zone is imaged onto one fiber array, which delivers light from each illumination volume to a unique point in the focal plane of a spectral detection module. In a variant of this configuration, light collected from one of the illumination volumes (e.g., from a trigger subzone) is delivered to a point detection module, while the light collected from each of the other illumination volumes is delivered to a unique point in the focal plane of a spectral detection module. In another configuration, light from two sides of the measurement zone is imaged onto two fiber arrays, which are then combined to deliver light from both sides of each illumination volume to a unique point in the focal plane of a spectral detection module. In a variant of this configuration, light collected from one or two sides of one of the illumination volumes (e.g., from a trigger subzone) is delivered to a point detection module, while the light collected from each of the other illumination volumes is delivered to a unique point in the focal plane of a spectral detection module.

An optical fiber array can include 2 to 20 fibers (e.g., fiber optic cables, optical fiber cables, multimode optical fibers). For example, an optical array can include 2, 3, 4, 5, 6, 7, 8, 9, 10, 11, 12, 13, 14, 15, 16, 17, 18, 19, or 20 fibers. In some embodiments, an optical fiber array contains 3 fibers. In some embodiments, an optical fiber array contains 4 fibers. In some embodiments, an optical fiber array contains 5 fibers. In some embodiments, an optical fiber array contains 5 fibers. Fibers in a fiber array can be arranged in any suitable configuration. In some embodiments, the fibers are stacked in a linear array.

Figure 3A:
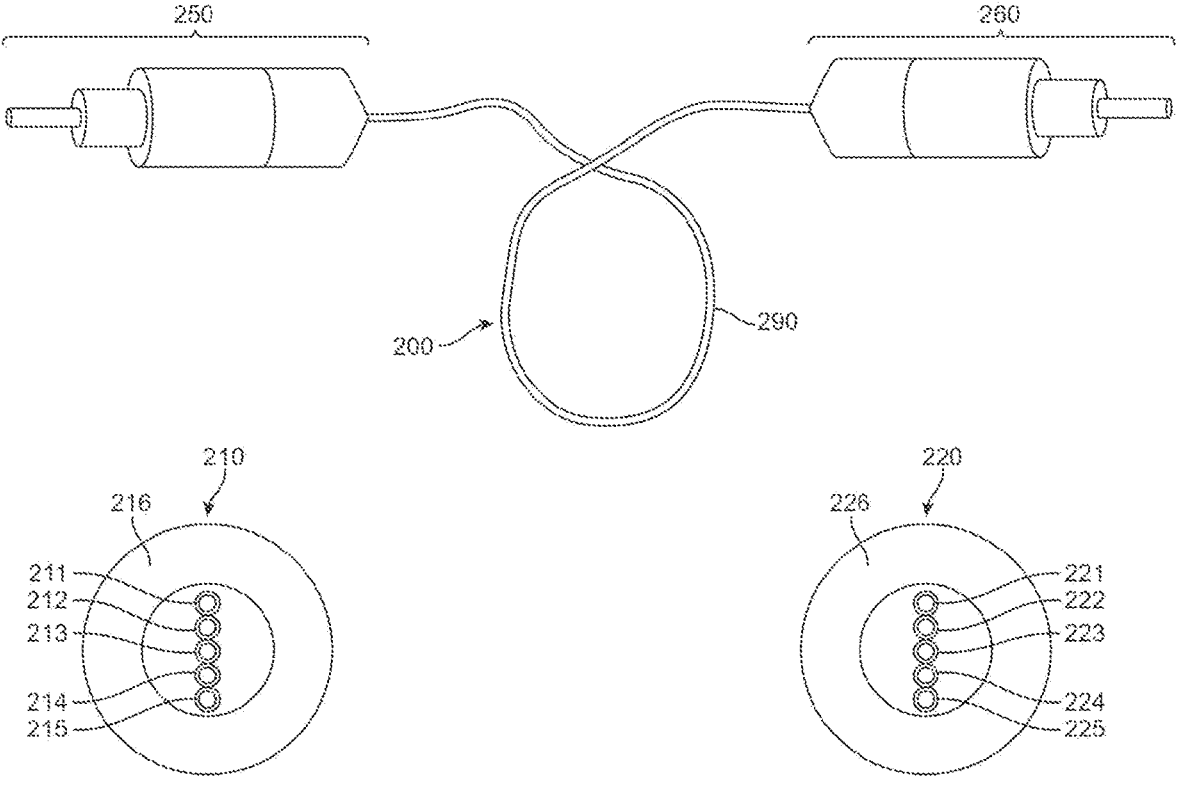
FIG. 3A shows an example of a light transmission module.

FIGS. 3A-3E depict light transmission modules in various configurations. A non-limiting example of a light transmission module is provided in FIG. 3A. One embodiment of a light transmission module is illustrated as module 200 (i.e., light transmission module in configuration A), which includes a fiber optic cable 290, a first fiber optic cable plug assembly 250 (i.e., for connecting to a collection optic), and a second fiber optic cable plug assembly 260 (i.e., for connecting to a spectral detector). FIG. 3A also shows cross section views of the fiber array connected to a collection optic (input) 210 and the fiber array connected to a spectral detector (output) 220. The fiber array connected to a collection optic (input) 210 includes optical fiber i (input) 211, optical fiber ii (input) 212, optical fiber iii (input) 213, optical fiber iv (input) 214, and optical fiber v (input) 215, housed in a fiber optic cable (216). The fiber array connected to a spectral detector (output) 220 includes optical fiber i (output) 221, optical fiber ii (output) 222, optical fiber iii (output) 223, optical fiber iv (output) 224, and optical fiber v (output) 225, housed in a fiber optic cable (226).

Figure 3B:
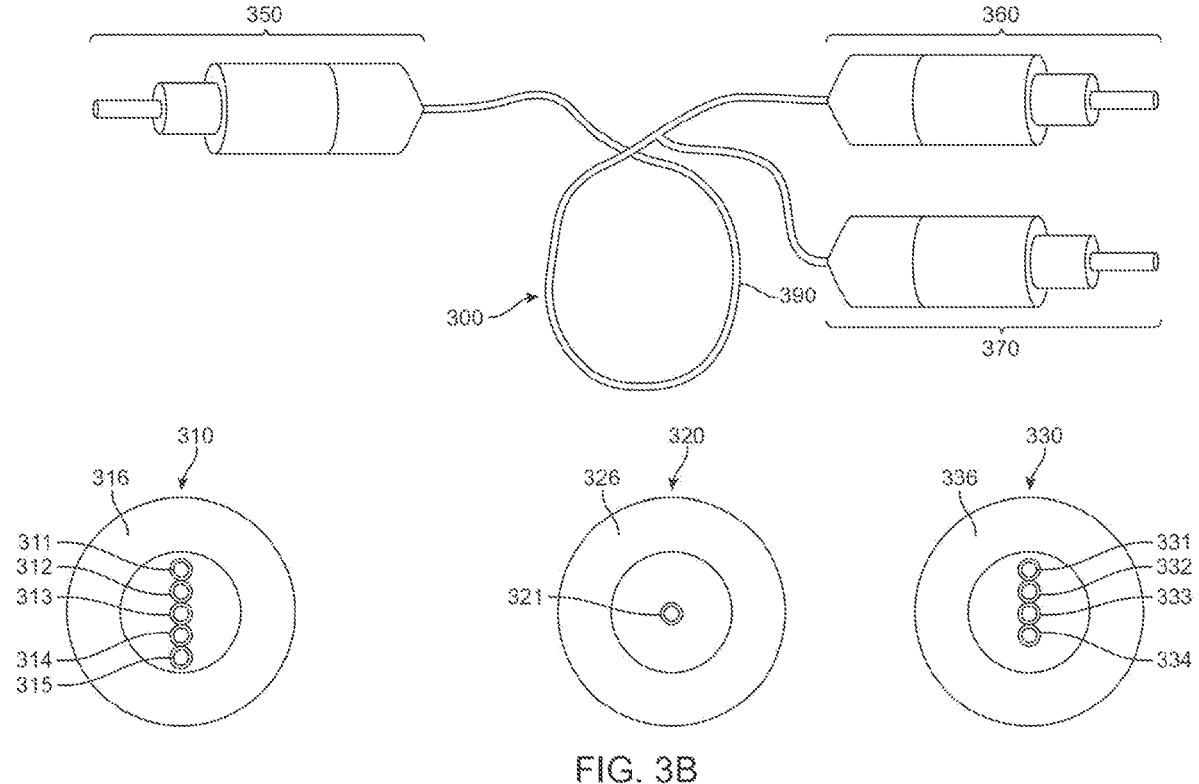
FIG. 3B shows a second example of a light transmission module.

Another non-limiting example of a light transmission module is provided in FIG. 3B. One embodiment of a light transmission module is illustrated as module 300 (i.e., light transmission module in configuration B), which includes a fiber optic cable 390, a first fiber optic cable plug assembly 350 (i.e., for connecting to a collection optic), a second fiber optic cable plug assembly 360 (i.e., for connecting to a point detector), and a third fiber optic cable plug assembly 370 (i.e., for connecting to a spectral detector). FIG. 3B also shows cross section views of the fiber array connected to a collection optic (input) 310 and the fiber array connected to a point detector (output) 320 and a spectral detector (output) 330. The fiber array connected to a collection optic (input) 310 includes optical fiber i (input) 311, optical fiber ii (input) 312, optical fiber iii (input) 313, optical fiber iv (input) 314, and optical fiber v (input) 315, housed in a fiber optic cable 316. The fiber array connected to a point detector (output) 320 includes optical fiber i (output) 321, housed in a fiber optic cable 326. The fiber array connected to a spectral detector (output) 330 includes optical fiber ii (output) 331, optical fiber iii (output) 332, optical fiber iv (output) 333, and optical fiber v (output) 334, housed in a fiber optic cable 336.

Figure 3C:
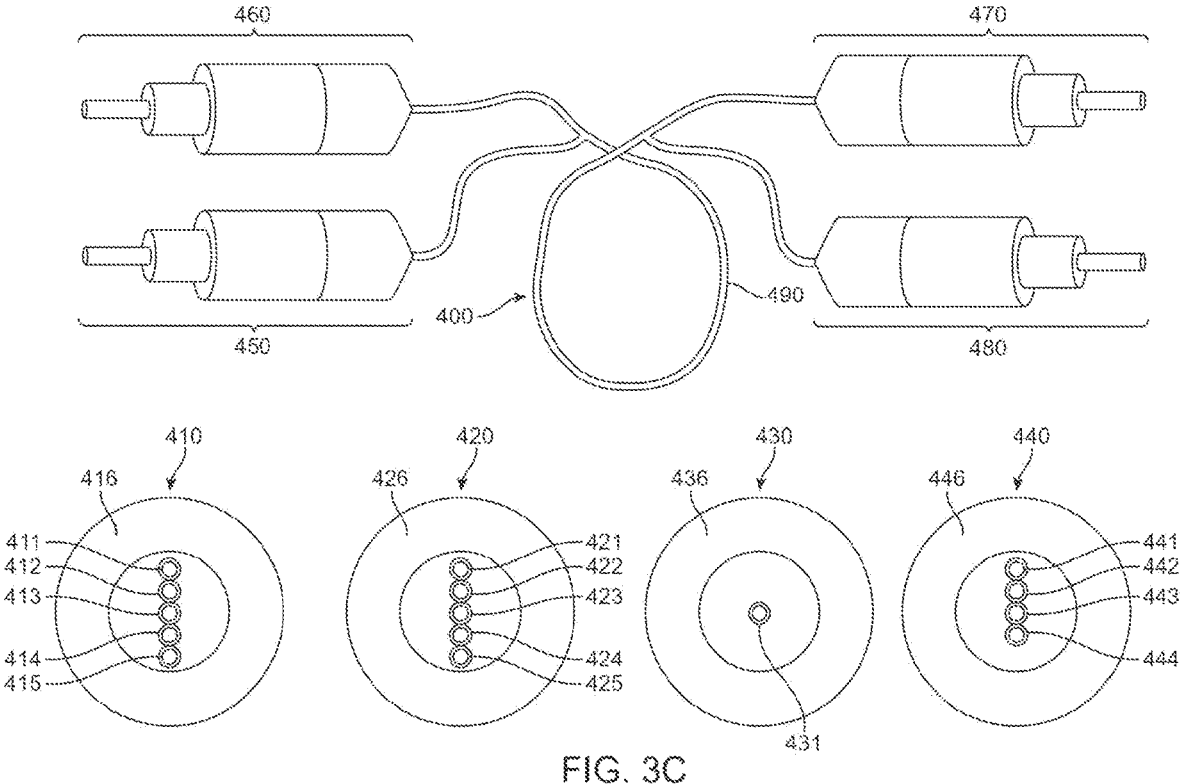
FIG. 3C shows a third example of a light transmission module.

Another non-limiting example of a light transmission module is provided in FIG. 3C. One embodiment of a light transmission module is illustrated as module 400 (i.e., light transmission module in configuration C), which includes a fiber optic cable 490, a first fiber optic cable plug assembly 450 (i.e., for connecting to a first collection optic), a second fiber optic cable plug assembly 460 (i.e., for connecting to a second collection optic), a third fiber optic cable plug assembly 470 (i.e., for connecting to a point detector), and a fourth fiber optic cable plug assembly 480 (i.e., for connecting to a spectral detector). FIG. 3C also shows cross section views of the fiber array connected to a first collection optic (input) 410 and a second collection optic (input) 420; and the fiber array connected to a point detector (output) 430 and a spectral detector (output) 440. The fiber array connected to a first collection optic (input) 410 includes optical fiber i (input) 411, optical fiber ii (input) 412, optical fiber iii (input) 413, optical fiber iv (input) 414, and optical fiber v (input) 415, housed in a fiber optic cable 416. The fiber array connected to a second collection optic (input) 420 includes optical fiber i' (input) 421, optical fiber ii' (input) 422, optical fiber iii' (input) 423, optical fiber iv' (input) 424, and optical fiber v' (input) 425, housed in a fiber optic cable 426. The fiber array connected to a point detector (output) 430 includes an optical fiber transmitting a combined signal from optical fiber i and optical fiber i' (output) 431, housed in a fiber optic cable 436. The fiber array connected to a spectral detector (output) 440 includes an optical fiber transmitting a combined signal from optical fiber ii and optical fiber ii' (output) 441, an optical fiber transmitting a combined signal from optical fiber iii and optical fiber iii' (output) 442, an optical fiber transmitting a combined signal from optical fiber iv and optical fiber iv' (output) 443, and an optical fiber transmitting a combined signal from optical fiber v and optical fiber v' (output) 444, housed in a fiber optic cable 446.

Figure 3D:
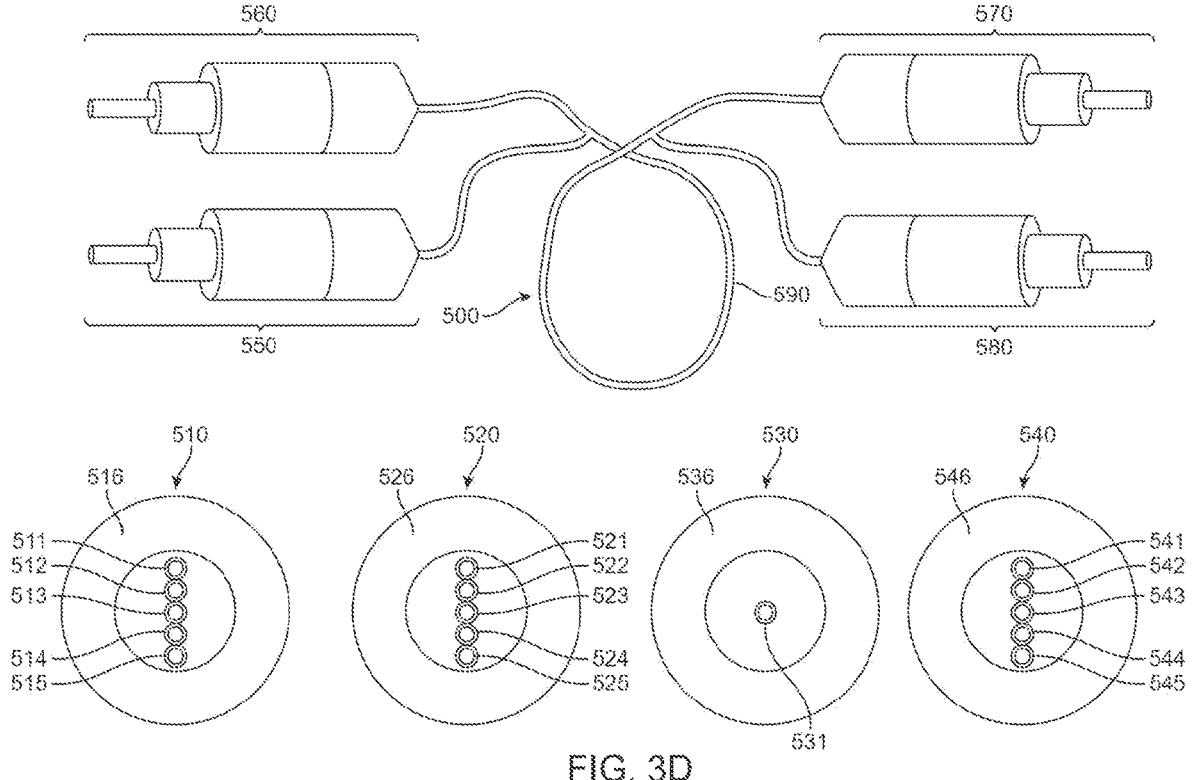
FIG. 3D shows a fourth example of a light transmission module.

Another non-limiting example of a light transmission module is provided in FIG. 3D. One embodiment of a light transmission module is illustrated as module 500 (i.e., light transmission module in configuration D), which includes a fiber optic cable 590, a first fiber optic cable plug assembly 550 (i.e., for connecting to a first collection optic), a second fiber optic cable plug assembly 560 (i.e., for connecting to a second collection optic), a third fiber optic cable plug assembly 570 (i.e., for connecting to a point detector), and a fourth fiber optic cable plug assembly 580 (i.e., for connecting to a spectral detector). FIG. 3D also shows cross section views of the fiber array connected to a first collection optic (input) 510 and a second collection optic (input) 520; and the fiber array connected to a point detector (output) 530 and a spectral detector (output) 540. The fiber array connected to a first collection optic (input) 510 includes optical fiber i (input) 511, optical fiber ii (input) 512, optical fiber iii (input) 513, optical fiber iv (input) 514, and optical fiber v (input) 515, housed in a fiber optic cable 516. The fiber array connected to a second collection optic (input) 520 includes optical fiber i' (input) 521, optical fiber ii' (input) 522, optical fiber iii' (input) 523, optical fiber iv' (input) 524, and optical fiber v' (input) 525, housed in a fiber optic cable 526. The fiber array connected to a point detector (output) 530 includes an optical fiber transmitting a signal from optical fiber i (output) 531, housed in a fiber optic cable 536. The fiber array connected to a spectral detector (output) 540 includes an optical fiber transmitting a signal from optical fiber i' (output) 541, an optical fiber transmitting a combined signal from optical fiber ii and optical fiber ii' (output) 542, an optical fiber transmitting a combined signal from optical fiber iii and optical fiber iii' (output) 543, an optical fiber transmitting a combined signal from optical fiber iv and optical fiber iv' (output) 544, and an optical fiber transmitting a combined signal from optical fiber v and optical fiber v' (output) 545, housed in a fiber optic cable 546.

Figure 3E:
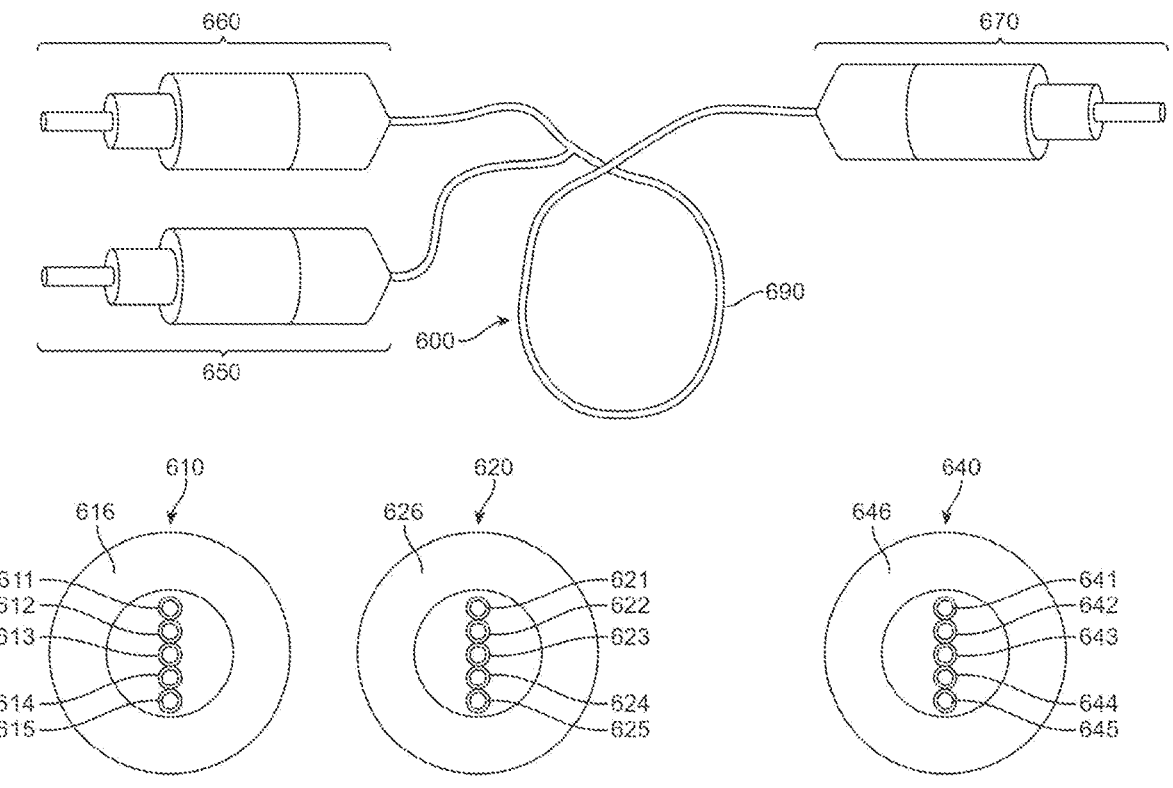
FIG. 3E shows a fifth example of a light transmission module.

Another non-limiting example of a light transmission module is provided in FIG. 3E. One embodiment of a light transmission module is illustrated as module 600 (i.e., light transmission module in configuration E), which includes a fiber optic cable 690, a first fiber optic cable plug assembly 650 (i.e., for connecting to a first collection optic), a second fiber optic cable plug assembly 660 (i.e., for connecting to a second collection optic), a third fiber optic cable plug assembly 670 (i.e., for connecting to a spectral detector). FIG. 3E also shows cross section views of the fiber array connected to a first collection optic (input) 610 and a second collection optic (input) 620; and the fiber array connected to a spectral detector (output) 640. The fiber array connected to a first collection optic (input) 610 includes optical fiber i (input) 611, optical fiber ii (input) 612, optical fiber iii (input) 613, optical fiber iv (input) 614, and optical fiber v (input) 615, housed in a fiber optic cable 616. The fiber array connected to a second collection optic (input) 620 includes optical fiber i' (input) 621, optical fiber ii' (input) 622, optical fiber iii' (input) 623, optical fiber iv' (input) 624, and optical fiber v' (input) 625, housed in a fiber optic cable 626. The fiber array connected to a spectral detector (output) 640 includes an optical fiber transmitting a signal from optical fiber i' (output) 641, an optical fiber transmitting a combined signal from optical fiber ii and optical fiber ii' (output) 642, an optical fiber transmitting a combined signal from optical fiber iii and optical fiber iii' (output) 643, an optical fiber transmitting a combined signal from optical fiber iv and optical fiber iv' (output) 644, and an optical fiber transmitting a combined signal from optical fiber v and optical fiber v' (output) 645, housed in a fiber optic cable 646.

Detector Module

An EEM FC system herein can include a detector module. A detector module can include a selective optical element, a dispersive optical element, or a selective optical element and a dispersive optical element. A selective optical element can be coupled to a point detector. A selective optical element coupled to a point detector can be referred to as a point detection module. A dispersive optical element can be referred to as a spectrograph or an imaging spectrograph. A dispersive optical element can be coupled to a spectral detector. A spectral detector can include a camera or photodetector (e.g., charge coupled device (CCD) camera, CCD detector, CMOS array, photodiode (PD), avalanched photodiode (APD) array, multianode PMT, other appropriate photodetector) interfaced to a data analysis system. A dispersive optical element can be referred to as a spectral dispersion module, and a spectral detector can be referred to as a spectral detection module.

In some embodiments, a detector module includes one or more of a lens, an obscuration bar, a mirror, a photomultiplier tube (PMT), a filter, a slit (a small opening for light diffraction, typically long and narrow; e.g., optical slit), a prism, and a grating. In some embodiments, a detector module includes an obscuration bar. An obscuration bar also can be referred to as a forward scatter obscuration bar and helps to diminish background in a detector by blocking light (e.g., laser light) from interacting with the detector. For example, when no particle is present in a laser beam, scattered laser light hits and can be blocked by an obscuration bar, and when a particle is present in a laser beam, laser light refracted (scattered) by the particle can pass over the bar.

In some embodiments, a detector module includes one or more filters. For example, a detector module can include one or more of a bandpass filter, a notch filter, and an edge filter. In some embodiments, a detector module includes a bandpass filter. A bandpass filter, as used herein, generally is a device that passes frequencies (e.g., wavelengths) within a certain range and rejects (attenuates) frequencies (e.g., wavelengths) outside that range. In some embodiments, a detector module includes a notch filter. A notch filter, as used herein, generally is a type of a band-stop filter (or band-rejection filter), which is a filter that passes most frequencies (e.g., wavelengths) unaltered, but attenuates those in a specific range to very low levels. A notch filter is generally considered a band-stop filter with a narrow stopband. In some embodiments, a detector module includes an edge filter. Edge filters can include long wave pass filters and short-wave pass filters. Long wave pass filters generally minimize transmission below a given wavelength and maximize transmission above it; and short-wave pass filters generally minimize transmission above a given wavelength and maximize transmission below it.

In some embodiments, a detector module includes one or more lenses and/or mirrors. In some embodiments, a detector module includes a collimating lens. A collimating lens generally is a curved optical lens that directs light rays to travel parallel to each other. In some embodiments, a detector module includes a focusing lens. A focusing lens generally directs light rays to a focal point. In some embodiments, a detector module includes a collimating lens and a focusing lens. In some embodiments, a detector module includes a dichroic filter. A dichroic filter (thin-film filter, interference filter) generally is a color filter used to selectively pass light of a small range of colors while reflecting other colors. In some embodiments, a detector module includes a dichroic mirror. A dichroic mirror (dichroic reflector) is similar to a dichroic filter but generally is characterized by the color(s) of light that they reflect, rather than the color(s) they pass.

In some embodiments, the selective optical element includes one or more of a collimating lens, a bandpass filter, a dichroic mirror, a photomultiplier tube (PMT). In some embodiments, the selective optical element includes a photomultiplier tube (PMT). A PMT generally is a type of vacuum phototube that can detect light in the ultraviolet, visible, and near-infrared ranges of the electromagnetic spectrum. A PMT can multiply the current produced by light, permitting detection of individual photons, in certain instances. In some configurations, a PMT is interfaced to a data analysis system.

In some embodiments, the dispersive optical element includes a prism. A prism generally is a transparent optical element that can refract light. A dispersive prism can be used to break light up into its constituent spectral colors (e.g., the colors of the rainbow). In some embodiments, the dispersive optical element includes a grating (e.g., a diffraction grating, volume phase holographic grating). A grating (e.g., a diffraction grating, volume phase holographic grating) generally is an optical component with a periodic structure, which splits and diffracts light into several beams travelling in different directions. In some embodiments, the dispersive optical element includes a prism and a grating.

A dispersive optical element can be coupled to a spectral detector. A spectral detector senses the spectral image of the light collected from each illumination volume on different areas of a sensor surface. In one configuration, the spectral image of each illumination volume is sensed on a different track on the sensor surface reflecting the linear arrangement of optical fibers in the fiber array. The detector can be programmed to read out the signal from the light on each track such that the spectra from each illumination volume is sent to a data analysis system. Instructions for programming the detector operation and readout can be provided by the data analysis system. These instructions can include the measurement time, the electronic gain, the dimensions of each track, and the desired resolution of the spectra from the illumination volumes. When each illumination volume is excited by a different illumination wavelength, the spectral image of the optical fiber array measured on the different detector tracks represents the hyperspectral image of the particle being measured. A spectral detector can include a camera or photodetector (e.g., charge coupled device (CCD) camera, CCD detector, CMOS array, photodiode (PD), avalanched photodiode (APD) array, multianode PMT, other appropriate photodetector) interfaced to a data analysis system.

An example detector module can include a fiber array input adapter, collimating optics, a narrow band notch filter to reject excitation light, a grating to disperse the collected light, a focusing optic, and an array detector (e.g., CCD, CMOS array, photodiode (PD), avalanched photodiode (APD) array, multianode PMT, other appropriate photodetector) interfaced to a data analysis system. In some configurations, a detector module can also include an additional focusing lens, slit or aperture, and a second collimating lens to provide a limiting aperture to adjust light throughput and spectral resolution.

Figure 4A:
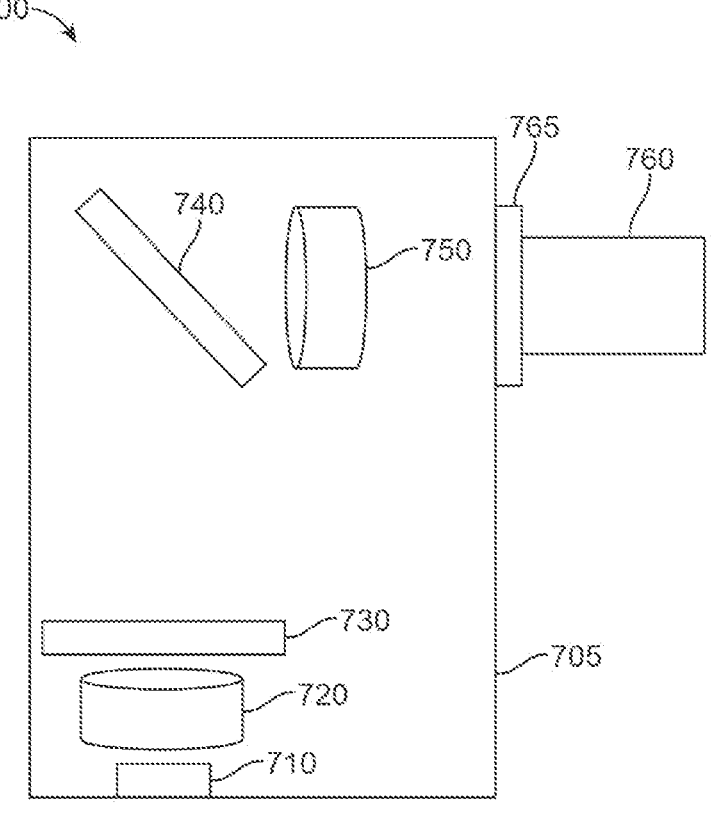
FIG. 4A shows an example of a detector module.
Figure 4B:
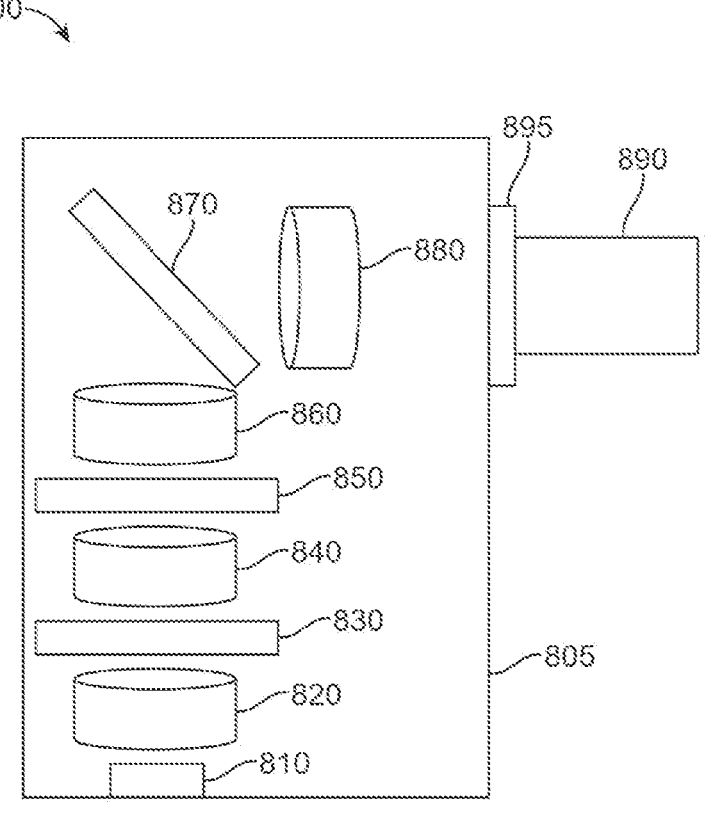
FIG. 4B shows another example of a detector module.

FIGS. 4A and 4B each show a spectral dispersion module and spectral detection module. FIG. 4A shows a module without an intermediate slit. FIG. 4B shows a module with an intermediate slit.

A non-limiting example of a detector module is provided in FIG. 4A. One embodiment of a detector module is illustrated as module 700. In one embodiment, a detector module 700 contains a spectral dispersion module 705, which includes a fiber input adapter 710, collimating lens 720, notch filter 730, grating 740, and focusing lens 750. A detector module 700 further includes a detector 760 and a detector adapter 765 connected to the spectral dispersion module 705.

Another non-limiting example of a detector module is provided in FIG. 4B. One embodiment of a detector module is illustrated as module 800. In one embodiment, a detector module 800 includes a spectral dispersion module 805, which contains a fiber input adapter 810, first collimating lens 820, notch filter 830, first focusing lens 840, slit 850, second collimating lens 860, grating 870, and second focusing lens 880. A detector module 800 further includes a detector 890 and a detector adapter 895 connected to the spectral dispersion module 805.

Data Analysis System

An EEM FC system herein can include a data analysis system. A data analysis system can be referred to as a data system, a data module, a data analysis module, a data acquisition system, or a data acquisition module. A data analysis system generally is configured to analyze light detected by a detector. In some embodiments, a data analysis system is configured to analyze component signals detected by a detector. In some embodiments, a data analysis system is configured to analyze composite signals detected by a detector. In some embodiments, a composite signal is a composite of output signals from a single measurement subzone. In some embodiments, a composite signal is a composite of output signals from a plurality of measurement subzones.

In configurations where the detector contains a selective optical element, a selective subset of component signals obtained by the selective optical element can be analyzed. In configurations where the detector contains a dispersive optical element, component spectral signals from a composite output signal of a single measurement subzone can be analyzed. In configurations where the detector contains a dispersive optical element, component spectral signals from a composite output signal of a plurality of measurement subzones can simultaneously be analyzed. In configurations where the detector contains a dispersive optical element, component spectral signals from a composite output signal of a single measurement subzone can be analyzed and component spectral signals from a composite output signal of a plurality of measurement subzones can simultaneously be analyzed.

A data analysis system can include analogue and digital signal processing hardware and/or software. Analogue hardware can include, for example, preamp circuits to process analogue signals from the photomultiplier tubes (PMTs), photodiodes (PDs), or other detectors, where the processing may include amplification, filtering, and baseline resort to null out DC signal if desired. Digital hardware can include, for example, a microprocessor that contains analogue to digital converters (ADCs) to sample the analogue signals to produce a digital stream of data, random access memory (RAM) to store the data, and a digital signal processor (DSP) core that performs digital signal processing, including digital signal filtering/conditioning, signal pulse detection, signal pulse analysis, and signal pulse classification. Digital hardware also can include digital to analogue converters (DACs) to communicate with detectors and a USB interface between the DSP and an external computer. Software can include routines to communicate with hardware and detectors, including setting detector operating conditions, receiving, processing, and analyzing data, controlling light sources, and controlling a fluidics module.

A data analysis system can be configured to send instructions to point detectors and spectral detection modules, to receive signals and data from point detectors and spectral detection modules, to send instructions to an integrated laser module, and/or to process data to detect and analyze particles for characterization, classification, and/or identification of the particles. Data processing can include spectral analysis, including spectral unmixing, decomposition, and/or classification. Data processing algorithms can be provided and accessed as MatLab scripts, C++ routines in the data analysis software, and/or executed in the data analysis hardware using digital signal processors (DSPs) and/or field-programmable gate arrays (FPGAs). A data analysis system can be configured to control light sources and detectors to produce hyperspectral data sets from single particles, and process and analyze that hyperspectral data set to characterize, classify, and/or identify single particles, and provide high quality single particle resolution.

A representative data analysis system can include hardware and software that accepts data from point detectors (e.g., PDs, APDs, and PMTs) and spectral detectors (e.g., PMT, CCD, CMOS, or APD arrays). A representative data analysis system can digitize and analyzes signal pulses to detect the occurrence of a particle and to extract one or more features of the signal pulses. A representative data analysis system can communicate with a spectral detection module to trigger detection of the spectral signal and to receive, analyze and record the spectral data. A representative data analysis system can control the output of light sources to synchronize with the passage of the particle through subzones within the measurement zone. A representative data analysis system can operate in one of several measurement modes: conventional mode, where signals falling into discrete bandpass ranges are associated with specific fluorophores and/or fluorescent ligands; spectral mode, where the spectra of light coming from each illumination volume is analyzed to determine the signal from each of one or more known or unknown fluorophores; or hyperspectral mode, where the spectra of light from all of the illumination volumes is analyzed to determine the signal from each of one or more known or unknown fluorophores.

Figure 13:
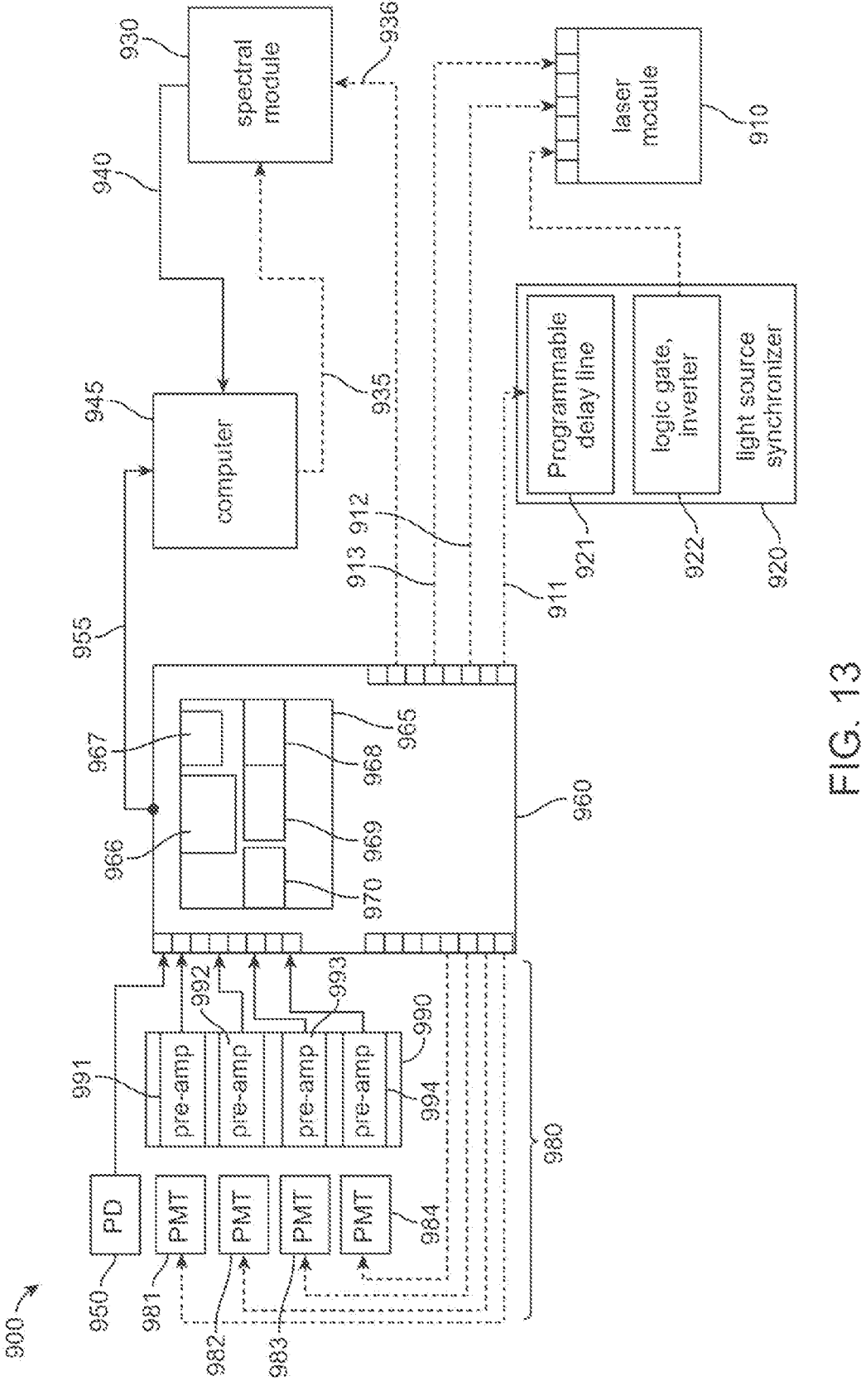
FIG. 13 shows a data flow schematic (Top Left: Signals into Data System. Bottom Left: Detector Gain Control out. Bottom Right: Laser Control Signal out).

A non-limiting example of data flow using a data analysis system is provided in FIG. 13. One embodiment of data flow using a data analysis system is illustrated as schematic 900. In one embodiment, a data flow schematic 900 includes a light source synchronizer 920. A light source synchronizer 920 includes a programmable delay line 921 and a logic gate/inverter 922. In one embodiment, a data flow schematic 900 includes a laser module 910 and laser 1 control 911, laser 2 control 912, and laser 3 control 913. In one embodiment, a data flow schematic 900 includes a spectral module 930, spectral control 935, spectral trigger 936, spectral data 940, and computer 945. In one embodiment, a data flow schematic 900 includes a point detector, e.g., photodiode 950 and point detector data 955. In one embodiment, a data flow schematic 900 includes a data analysis system 960 comprising hardware and software. A data analysis system 960 includes a microprocessor 965. A microprocessor 965 includes FLASH RAM 966, universal serial bus (USB) 967, digital signal processor (DSP) 968, random access memory (RAM) 969, and analog to digital converter (ADC) 970. In one embodiment, a data flow schematic 900 includes a photomultiplier tube (PMT) high voltage (HV) control 980, PMT 1 981, PMT 2 982, PMT 3 983, PMT 4 984, and preamp circuits 990 including preamp circuit 1 991, preamp circuit 2 992, preamp circuit 3 993, and preamp circuit 4 994.

Excitation-Emission Matrix Flow Cytometry (EEM FC) Methods

Provided herein are methods for analyzing biological particles using an excitation-emission matrix flow cytometry (EEM FC) system described herein. Analytes (e.g., biological particles, or artificial/synthetic particles contained in a sample) that can be analyzed are described herein.

A method herein can include analyzing a particle in a flow cytometer (e.g., an excitation-emission matrix flow cytometer (EEM FC) described and provided herein). A method can include: introducing a sample comprising at least one particle to a flow channel comprising a plurality of measurement subzones; sequentially illuminating the measurement subzones in the flow channel as each particle flows through the flow channel; collecting and delivering light emitted by the particle in one or more of the measurement subzones to a detector; and detecting light emitted by the particle.

In some embodiments, a method provided herein includes introducing a sample containing at least one particle to a flow channel containing a plurality of measurement subzones. A sample can be introduced to a flow channel by way of a fluid delivery line, as described herein. Measurement subzones, described herein, can in certain embodiments be positioned linearly in the direction of fluid flow in the flow channel.

In some embodiments, a method herein includes sequentially illuminating measurement subzones in a flow channel as a particle flows through a flow channel. Sequential illumination of measurement subzones in a flow channel can be performed by a light source synchronizer and/or a controller in a light source synchronizer described and provided herein. In some embodiments, a particle emits light in response to being illuminated in at least one of the measurement subzones. Once illuminated, a measurement subzone can be referred to as an illumination volume or an illumination zone. Accordingly, in some embodiments, a method provided herein includes sequentially generating a plurality of illumination volumes when the measurement subzones are sequentially illuminated. In some embodiments, each of the measurement subzones is illuminated with a wavelength of light different than for the other measurement subzones. For example, each of the measurement subzones can be illuminated with a different wavelength of light between about 200 nm to about 500, 550, 600, 650, 700, 750, 800, 850,900, 950, 1000, 1050, 1100, 1150, 1200, 1250, 1300, 1350 or 1400 or more nm.

In some embodiments, each of the measurement subzones is illuminated when a particle is located therein and each of the measurement subzones is not illuminated when the particle is not located therein. Thus, each measurement subzone is illuminated only when a particle is present in the measurement subzone. In some embodiments, a method herein includes sequentially activating and deactivating a plurality of light sources. Typically, each of the light sources illuminates each of the measurement subzones. In other words, each light source can be coupled to a particular measurement subzone such that each light source has a corresponding measurement subzone. Once illuminated, each measurement subzone has a corresponding illumination volume. Thus, each light source also can have a corresponding illumination volume.

In some embodiments, a method provided herein includes activating and deactivating one or more switches. Generally, each switch is configured to activate and deactivate each of the light sources. In other words, each switch can be coupled to a particular light source such that each switch has a corresponding light source. In some embodiments, a method provided herein includes activating each of the light sources in the plurality of light sources one at a time while each of the other light sources is deactivated.

In some embodiments, a method provided herein includes sequentially activating one of the light sources after deactivating one of the other light sources, for example, in a strobed manner. Sequentially activating and deactivating light sources can be performed by a light source synchronizer and/or a controller in a light source synchronizer described herein. In some embodiments, a method provided herein includes (i) activating a light source that illuminates a measurement subzone, while all other light sources are deactivated; (ii) deactivating the light source that illuminates the measurement subzone illuminated in (i) and activating a light source that illuminates a measurement subzone located next to the measurement subzone illuminated in (i) and closer to an outlet in a flow channel, while all other light sources are deactivated, and (iii) repeating (i) and (ii) until a light source that illuminates a measurement subzone closest to the flow channel outlet is activated and then deactivated.

In some embodiments, a method provided herein includes detecting the presence of a particle in a measurement subzone closest to an inlet in a flow channel, and transmitting a signal to sequentially activate and deactivate light sources. A measurement subzone closest to an inlet in a flow channel can be referred to as a trigger zone, as described herein. The presence of a particle in a measurement subzone closest to an inlet in a flow channel can be detected by a detector (e.g., a point detection module described herein). A signal to sequentially activate and deactivate light sources can be transmitted from a detector to a data analysis module, an illumination module and/or a light source synchronizer described herein.

In some embodiments, a method provided herein includes delivering light from light sources to a flow channel. Light can be delivered light from light sources to a flow channel by a light delivery module described and provided herein. In some embodiments, light can be delivered from light sources to a flow channel through an optical fiber. In some embodiments, light can be delivered from light sources to a flow channel through a plurality of optical fibers. In some embodiments, delivering light from light sources to a flow channel includes the use of a shaping optic. In some embodiments, delivering light from light sources to a flow channel includes the use of a focusing optic. In some embodiments, delivering light from light sources to a flow channel includes the use of a shaping optic and a focusing optic.

In some embodiments, a method provided herein includes collecting light emitted by a particle in one or more measurement subzones. Light can be collected using one or more collectors as described herein. In some embodiments, light is collected using at least two collectors. In some embodiments, collecting light includes use of a collector positioned parallel to the direction of light emitted from light sources. In some embodiments, collecting light includes use of a collector positioned orthogonal to the direction of light emitted from light sources. In some embodiments, a collector is located at a position proximal to the flow channel. In some embodiments, a collector is located at a position distal to the flow channel. In some embodiments, a first collector is located at a position proximal to a flow channel and a second collector is located at a position distal to the flow channel. In some embodiments, a method provided herein includes use of two collectors positioned orthogonal to the direction of light emitted by light sources. In some embodiments, a method provided herein includes use of two collectors positioned opposite to one another. In some embodiments, a method provided herein includes use of two collectors positioned proximal to a flow channel and distal to the flow channel. In some embodiments, a method provided herein includes use of two collectors positioned orthogonal to the direction of light emitted by light sources, positioned opposite to one another, and positioned proximal to a flow channel and distal to the flow channel.

In some embodiments, a method provided herein includes delivering light emitted by the particle in one or more of the measurement subzones to a detector. In some embodiments, a method provided herein includes delivering light from one or more collectors to a selective optical element. A selective optical element can contain a photomultiplier tube (PMT). In some embodiments, a method provided herein includes delivering light from one or more collectors to a dispersive optical element. A dispersive optical element can include a prism, or a grating, or a prism and a grating. In some embodiments, a method provided herein includes delivering light from one or more collectors to a selective optical element and to a dispersive optical element. Light can be delivered from a collector to a selective optical element and/or a dispersive optical element through an optical fiber, in some embodiments. Light can be delivered from a collector to a selective optical element through a plurality of optical fibers, in some embodiments. Light can be delivered from a collector to a dispersive optical element through a plurality of optical fibers, in some embodiments. Light can be delivered from a collector to a selective optical element and a dispersive optical element through a plurality of optical fibers, in some embodiments. In some embodiments, light can be be delivered from two collectors to a selective optical element through a plurality of optical fibers. In some embodiments, light can be delivered from two collectors to a dispersive optical element through a plurality of optical fibers. In some embodiments, light can be delivered from two collectors to a selective optical element and a dispersive optical element through a plurality of optical fibers.

In some embodiments, a method provided herein includes combining the light from two collectors. In some embodiments, a method provided herein includes combining the light from two collectors and delivering the combined light from the two collectors to a selective optical element. In some embodiments, a method provided herein includes combining the light from two collectors and delivering the combined light from the two collectors to a dispersive optical element. In some embodiments, a method provided herein includes combining the light from two collectors. In some embodiments, a method provided herein includes combining the light from two collectors and delivering the combined light from the two collectors to a selective optical element and a dispersive optical element.

In some embodiments, a method provided herein includes delivering light emitted from the measurement subzone closest to a flow channel inlet obtained from a collector to a selective optical element; and delivering light emitted from the remaining measurement subzones obtained from both collectors to a dispersive optical element. In some embodiments, a method provided herein includes delivering light emitted from the measurement subzone closest to a flow channel inlet obtained from two collectors to a selective optical element; and delivering light emitted from the remaining measurement subzones obtained from the two collectors to a dispersive optical element. In some embodiments, a method provided herein includes delivering light emitted from the measurement subzone closest to a flow channel inlet obtained from a first collector module to a selective optical element; and delivering light emitted from some or all measurement subzones obtained from a second collector module to a dispersive optical element. In some embodiments, a method provided herein includes delivering light emitted from the measurement subzone closest to a flow channel inlet obtained from a first collector module to a selective optical element; delivering light emitted from the remaining measurement subzones obtained from the first collector to a dispersive optical element; and delivering light emitted from some or all measurement subzones obtained from a second collector module to a dispersive optical element.

In some embodiments, a method provided herein includes delivering light emitted by the particle in one or more of the measurement subzones to a detector. Light emitted by a particle (e.g., an illuminated particle) can be delivered as a composite signal to an optical element (e.g., an optical element coupled to a detector). In some embodiments, a composite signal is separated into component signals. A composite signal can be separated into component signals by a selective optical element described herein. A composite signal can be separated into component signals by a dispersive optical element described herein. A composite signal can be separated into component signals by a selective optical element described herein and a dispersive optical element described herein. In some embodiments, an optical element selectively obtains a subset of component discrete wavelength signals from the composite signal. In some embodiments, an optical element dispersively separates the composite signal into component spectral signals. In some embodiments, an optical element selectively obtains a subset of component discrete wavelength signals from the composite signal and dispersively separates the composite signal into component spectral signals.

In some embodiments, a particle is analyzed according to a selectively obtained subset of component discrete wavelength signals. An optical element can selectively obtain a subset of component discrete wavelength signals from a composite signal, and the selectively obtained subset of component discrete wavelength signals can be analyzed. In some embodiments, a particle is analyzed according to component spectral signals from a composite signal of a single measurement subzone. An optical element can dispersively separate a composite signal into component spectral signals, and the component spectral signals from the composite signal of a single measurement subzone can be analyzed. In some embodiments, a particle is analyzed according to component spectral signals from a composite signal of more than one measurement subzone. An optical element can dispersively separate a composite signal into component spectral signals, and the component spectral signals from the composite signal of more than one measurement subzone can simultaneously be analyzed.

In some embodiments, a method provided herein comprises detecting light emitted by a particle. Light emitted by a particle can be detected by a detector (e.g., a point detector, a spectral detector) described herein. In some embodiments, detecting light emitted by a particle includes use of one or more of a lens, an obscuration bar, a mirror, a photomultiplier tube (PMT), a filter, a slit, a prism, and a grating, each of which is described herein. In some embodiments, detecting light emitted by a particle includes use of a filter comprising a bandpass filter. In some embodiments, detecting light emitted by a particle includes use of a filter comprising a notch filter. In some embodiments, detecting light emitted by a particle includes use of a filter comprising an edge filter. In some embodiments, detecting light emitted by a particle includes use of one or more of a bandpass filter, a notch filer, and an edge filter. In some embodiments, detecting light emitted by a particle includes use of a lens comprising a collimating lens. In some embodiments, detecting light emitted by a particle includes use of a lens comprising a focusing lens. In some embodiments, detecting light emitted by a particle includes use of a collimating lens and a focusing lens.

In some embodiments, a method provided herein includes analyzing light detected by a detector. Analysis of light detected by a detector can be performed using a data analysis system described herein. In some embodiments, a method provided herein includes use of a selective optical element. In such embodiments, analyzing light can include analyzing a selective subset of component signals obtained by a selective optical element. In some embodiments, a method provided herein includes use of a dispersive optical element. In such embodiments, analyzing light can include analyzing component spectral signals from a composite output signal of a single measurement subzone. In some embodiments, analyzing light can include simultaneously analyzing component spectral signals from a composite output signal of a plurality of measurement subzones. In some embodiments, analyzing light can include analyzing component spectral signals from a composite output signal of a single measurement subzone and simultaneously analyzing component spectral signals from a composite output signal of a plurality of measurement subzones.

In some embodiments, a method provided herein includes sending instructions from a data analysis system to point detectors and/or spectral detection modules. In some embodiments, a method provided herein includes sending signals and data from point detectors and/or spectral detection modules to a data analysis system. In some embodiments, a method provided herein includes sending instructions from a data analysis system to an integrated laser module or an illumination module. In some embodiments, a method provided herein includes sending instructions from a data analysis system to a light source synchronizer. In some embodiments, a method provided herein includes processing data to detect and analyze particles for characterization, classification, and/or identification of the particles. Data processing can include spectral analysis, including spectral unmixing, decomposition, and/or classification. Data processing algorithms can be provided and accessed as MatLab scripts, C++ routines in the data analysis software, and/or executed in the data analysis hardware using digital signal processors (DSPs) and/or field-programmable gate arrays (FPGAs). In some embodiments, a data analysis system can control light sources and detectors to produce one or more hyperspectral data sets from single particles, and processes and analyzes the hyperspectral data sets to characterize, classify, and/or identify single particles to provide high quality single particle resolution.

A non-limiting example of a method herein includes analyzing biological particles using an EEM FC system is provided in FIG. 1. One embodiment of an EEM FC system is illustrated as system 100. Light from a plurality of light sources is delivered through a beam shaping/focusing optic 120 to a flow channel 105 (e.g., a flow channel in a flow cell). One embodiment of a plurality of light sources is illustrated as component 110, which includes light source 1 111 (e.g., laser 1, 405 nm), light source 2 112 (e.g., laser 2, 473 nm), light source 3 113 (e.g., laser 3, 488 nm), light source 4 114 (e.g., laser 4, 532 nm), and light source 5 115 (laser 5, 638 nm). Light emitted from particles in the flow channel is collected by a first collector 130 and a second collector 135, and light signals are transmitted via a first optical array 140 and a second optical array 145. Light signals transmitted via a first optical array 140 and a second optical array 145 merge at a merge point 150 (e.g., a merge point for the first optical array and the second optical array). Merged signals are transmitted to a point detection module 155 (e.g., containing a selective optical element and a point detector) and a spectral dispersion module 170. Dispersed light from a spectral dispersion module 170 is detected by a spectral detection module 175. Data generated by a point detection module 155 and a spectral detection module 175 is analyzed by a data analysis system 180 and transmitted to a computer 185 and/or a light source synchronizer 190. The light source synchronizer 190 controls the plurality of light sources 110. Light emitted from particles in the flow channel also is collected by a collection optic 160. A collection optic 160 is a FALS collection optic, in certain embodiments. Light collected by a collection optic 160 is transmitted to a point detection module 165 (e.g., containing a selective optical element and a point detector).

Analytes

Generally, analytes for use in the systems and methods provided herein include particles, where the particles can be analyzed by detection, identification, quantitation, size or other characterization based on the presence of one or more probes. Samples that contain particles for analysis according to the systems and methods provided herein generally include particles in a liquid medium. The particles can be biological, i.e., occurring in nature, or can be synthetic or artificially prepared particles. The particles can be analyzed by detection, identification, quantitation, size or other characterization based on the presence of one or more inherent probes, such as molecular markers associated with the particles, or an exogenously added probe, such as a tag, label, fluorophore or the like, can be used. Any samples containing particles in a liquid can be analyzed according to the methods provided herein.

Any aqueous or organic liquid medium containing particles, where the particles are not dissolved in the liquid medium, are contemplated for use in the methods herein. The liquid medium can be a solution that includes solutes dissolved in the liquid medium, such as buffers. In some embodiments, the samples include a suspension of particles, or a colloidal suspension of particles, in the liquid medium. Representative liquid media containing particles that can be analyzed according to the methods provided herein include, but are not limited to, blood, milk, water, solutions containing particles such as membrane vesicles, lipoproteins, viruses, virus-like particles, apoptotic bodies, synthetic liposomes or extracellular vesicles, and biological fluids other than blood such as plasma, serum, urine, saliva, seminal fluid, lavages (e.g., bronchoalveolar, gastric, peritoneal, ductal, ear, arthroscopic), cervical fluid, cervicovaginal fluid, cerebrospinal fluid, vaginal fluid, breast fluid, breast milk, synovial fluid, semen, seminal fluid, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof.

In some embodiments, the sample containing particles is a biological sample. In embodiments, the biological sample includes a biological fluid. The biological fluid in the biological sample can include, but is not limited to, blood, plasma, serum, urine, saliva, seminal fluid, lavages (e.g., bronchoalveolar, gastric, peritoneal, ductal, ear, arthroscopic), cervical fluid, cervicovaginal fluid, cerebrospinal fluid, vaginal fluid, breast fluid, breast milk, synovial fluid, semen, seminal fluid, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. In certain embodiments, the biological fluid is blood, plasma or serum. In some embodiments, the biological fluid is cerebrospinal fluid.

In certain embodiments, the biological sample is extracted from a cell or tissue sample of a subject, such as a biopsy sample (e.g., cancer biopsy), or is extracted from normal or cancer cell samples or normal or cancer tissue samples where the cell or tissue samples can be derived, e.g., from the liver, lung, kidney, spleen, pancreas, colon, skin, bladder, eye, brain, esophagus, head, neck, ovary, testes, prostate, the like or combination thereof. In some embodiments, the biological sample that is extracted from a cell or tissues sample of a subject includes a biological fluid.

In some embodiments, the biological sample includes particles derived from a cancer biopsy, a cancer cell or a cancer tissue. Cancer biopsy samples, cancer cell types or cancer tissue types from which particles can be present in the biological sample include, but are not limited to, liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney cells, heart cells, muscle cells, blood cells (e.g., white blood cells, platelets), the like and combinations of the foregoing. In embodiments, the cancer is a glioblastoma. In certain embodiments, the cancer is ovarian, lung, bladder or prostate cancer. In some embodiments, the biological sample that includes particles derived from a cancer biopsy, a cancer cell or a cancer tissue further includes a biological fluid. In embodiments, the biological fluid is blood, plasma, serum, saliva, urine or cerebrospinal fluid. In some embodiments, the cancer is ovarian, lung, bladder or prostate cancer and the biological fluid is saliva, urine or serum. In certain embodiments, the cancer is brain cancer. In some embodiments, the cancer is brain cancer and the biological fluid is cerebrospinal fluid. In embodiments, the brain cancer is glioblastoma.

In some embodiments, a sample can be blood and sometimes a blood fraction (e.g., plasma or serum). As used herein, the term "blood" encompasses whole blood or any fractions of blood, such as serum and plasma as conventionally defined, for example. Blood also contains buffy coats. Buffy coats sometimes are isolated by utilizing a Ficoll gradient. Buffy coats can comprise white blood cells (e.g., leukocytes, T-cells, B-cells, platelets, and the like) and samples extracted from buffy coats can include particles, e.g., extracellular vesicles (EVs), derived from these cells. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. In some embodiments, a sample obtained from a subject can contain cellular elements or cellular remnants. In some embodiments, cancer cells may be included in the sample. In embodiments, the sample is obtained from a human subject. In certain embodiments, the human subject is a cancer patient and in embodiments, the human subject does not have cancer.

Particles

1. Types of Particles

Any particles that can bind to or otherwise associate with an optically detectable label are contemplated for analysis according to the methods provided herein. The particles can occur in nature or can be synthetic or artificially prepared. The particles provided herein can be the particles of interest, i.e., the particles that are desired to be analyzed by the methods, or they can be used as optical standard particles for improved accuracy of measurement of the optical intensity.

Optically detectable labels for use in the methods and systems provided herein (e.g., for staining particles, including reference/standard particles, such as antibody capture particles) can include, but are not limited to fluorophores such as di-8-ANEPPS (3-[4-[(E)-2-[6-(dioctylamino)naphthalen-2-yl]ethenyl]pyridin-1-ium-1-yl]propane-1-sulfonate); di-4-ANEPPS (3-[4-[(E)-2-[6-(dibutylamino)naphthalen-2-yl]ethenyl]pyridin-1-ium-1-yl]propane-1-sulfonate)' a carbocyanine dye (e.g., DiO (e.g., $DiOC_{18}(3)$ (3, 3'-dioctadecyloxacarbocyanine perchlorate), DiL (e.g., DilC₁₈(3) (1, 1'-dioctadecyl-3, 3, 3', 3'-tetramethyl indocarbocyanine perchlorate); a PKH dye (lipophilic, long-chain carbocyanine dye); Dylight488® or equivalent green fluorophore that has an excitation wavelength of at or about 493 nm and an emission wavelength of at or about 518 nm; a Brilliant Violet dye (representative of which are BV-421 or equivalent fluorophore that has an excitation wavelength of at or about 407 nm and an emission wavelength of at or about 421 nm, BV-510 or equivalent fluorophore that has an excitation wavelength of at or about 405 nm and an emission wavelength of at or about 510 nm, BV-605 or equivalent fluorophore that has an excitation wavelength of at or about 405 nm and an emission wavelength of at or about 605 nm, and the like); Pacific Blue (3-carboxy-6,8-difluoro-7-hydroxycoumarin); Krome Orange or equivalent fluorophore that has an excitation wavelength of at or about 398 nm and an emission wavelength of at or about 528 nm; Brilliant Blue 515 or equivalent fluorophore that has an excitation wavelength of at or about 490 nm and an emission wavelength of at or about 515 nm; phycoerythrin (PE), rhodamine, fluorescein, FITC (fluorescein isothiocyanate), PerCPCy5.5, i.e., PerCP(peridinin-chlorophyll-protein complex) conjugated to Cy5.5, (6-[(2E)-1,1-dimethyl-2[(2E,4E)-5)-(1,1,3-trimethylbenzo[e]indol-3-ium-2-yl)penta-2,4-dienylidene]benzo[e]indol-3-yl]hexanoic acid; PE-Cy5.5 (phycoerythrin conjugated to Cy5.5); PE-Cy7 (phycoerythrin) conjugated to Cy7 (1-(5-carboxypentyl)-2-[7-(1-ethyl-5-sulfo-1,3-dihydro-2H-indol-2-ylidine)hepta-1,3,5-trien-1-yl]-3H-indolium-5-sulfonate); APC (allophycocyanin); the family of Alexa Fluor® dyes, such as Alexa647, APC-Alexa700 and APC-Alexa750 (Thermo Fisher Scientific, Waltham, MA):

The Alexa Fluor dyes were chemically synthesized through sulfonation and additional chemical modifications made to coumarin, rhodamine, and cyanine dyes, and to the xanthene family, of which fluorescein is a part. Examples of dyes from this family are set forth in the Table below:

| Name | Color | Absorb (Excitation) (nm) | Emission (nm) | MM (g/mol)[ | ε (cm⁻¹M⁻¹) | Quantum Yield |
|---|---|---|---|---|---|---|
| Alexa Fluor 350 | Blue | 346 | 442 | 410 | 19,000 | — |
| - 405 | Blue | 401 | 421 | 1028 | 35,000 | — |
| - 430 | Green | 434 | 541 | 702 | 15,000 | — |
| - 488 | Green | 495 | 519 | 643 | 73,000 | 0.92 |
| - 500 | Green | 502 | 525 | 700 | 71,000 | — |
| - 514 | Green | 517 | 542 | 714 | 80,000 | — |
| - 532 | Yellow | 532 | 554 | 721 | 81,000 | 0.61 |
| - 546 | Yellow | 556 | 573 | 1079 | 112,000 | 0.79 |
| - 555 | Orange | 555 | 565 | ~1250 | 155,000 | 0.1 |
| - 568 | Orange | 578 | 603 | 792 | 88,000 | 0.69 |
| - 594 | Red | 590 | 617 | 820 | 92,000 | 0.66 |
| - 610 | Red | 612 | 628 | 1172 | 144,000 | — |
| - 633 | Far-red | 632 | 647 | ~1200 | 159,000 | — |
| - 635 | Far-red | 633 | 647 | — | 140,000 | — |
| - 647 | Far-red | 650 | 665 | 1155.06 | 270,000 | 0.33 |
| - 660 | Near-IR | 663 | 690 | ~1100 | 132,000 | 0.37 |
| - 680 | Near-IR | 679 | 702 | ~1150 | 183,000 | 0.36 |
| - 700 | Near-IR | 702 | 723 | ~1400 | 205,000 | 0.25 |

-continued

| Name | Color | Absorb (Excitation) (nm) | Emission (nm) | MM (g/mol)[ | ε (cm⁻¹M⁻¹) | Quantum Yield |
|---|---|---|---|---|---|---|
| - 750 | Near-IR | 749 | 775 | ~1300 | 290,000 | 0.12 |
| - 790 | Near-IR | 782 | 805 | ~1750 | 260,000 | — |

ε = extinction coefficient

Other xanthene-based fluorophores, such as those of the Oregon Green® family, derivatives of rhodamine (e.g., Texas Red and tetrarhodimine isothiocynate (TRITC)), AMCA (aminomethyl coumarin acetate), Li-COR®, CyDyes® or DyLight® Fluors); fluorescent proteins and other fluorophores such as tdTomato, mCherry, mPlum, Neptune, TagRFP, mKate2, TurboRFP and TurboFP635 (Katushka).

Optical Standard Particles

In some aspects of the methods provided herein, one or more optical standard particles can be used to provide improved accuracy in determining the optical intensity of the optically detectable labels associated with the particles. In certain aspects, the optical standard particle can be a particle whose size (e.g., volume, diameter), type and/or amount is predetermined by a method that does not use an optically detectable label, such as NTA, tunable resistive pulse sensing (TRPS), electron microscopy (EM) or other methods. In aspects, the optical standard particle is capable of binding to or otherwise associating with an optically detectable label. The optical standard particle can then be contacted with an optically detectable label and the intensity of the label associated with the optical standard particle obtained, thereby providing a correlation between size and/or amount of the optical standard particle, and optical intensity.

In certain aspects, the optical standard particle is a bead. In aspects, the optical standard particle is a liposome or other lipid-containing particle. In aspects, the amount of lipid in the lipid-containing optical standard particle is known. In some aspects, the optical standard particle is a silica particle. In aspects, the silica particle includes a lipid bilayer. In aspects, the optical standard particle can include capture ligands that can bind to one or more molecular markers associated with a particle. In aspects, the ligand is an antibody. In certain aspects, the ligand is conjugated to an optically detectable label. In some aspects, the optical standard particle is a bead and the bead can capture ligands that can bind to one or more molecular markers associated with the particle.

In some aspects, the optical standard particle is in a collection or preparation of optical standard particles that include a size distribution of optical reference particles, whereby a regression correlation between a distribution of sizes and/or amounts and optical intensities of the optical standard particles associated with an optically detectable label can be obtained. In aspects, the optical standard particle is in a collection or preparation of optical standard particles that include a distribution of numbers of molecular markers associated with each particle in the preparation, whereby a regression correlation between a distribution of numbers of molecules of molecular marker per optical standard particle and the optical intensities of the optical standard particles associated with an optically detectable label can be obtained.

In certain aspects, the optical standard particles can be used for the analysis of particles according to the methods provided herein. In some aspects, the analysis is by flow cytometry. In aspects, the optical standard particle is a liposome, or a silica particle that includes a lipid bilayer. In some aspects, the optically detectable label associated with the liposome or the lipid bilayer of the silica particle is di-8-ANEPPS or fluorescently labeled (e.g., with DyLight488) annexin V. In certain aspects, the optical standard particle is a bead. In aspects, the optical standard particle can bind to or otherwise associate with a ligand.

In aspects, the ligand is an antibody. Any antibody as known and as described herein with respect to any aspect of the methods provided herein can be used as a ligand. In some aspects, the antibody is labeled with a fluorophore. In aspects, the antibody is selected from among anti-CD20, anti-CD3, anti-CD5, anti-CD56, anti-CD13, anti-CD4, anti-CD8, anti-CD19, anti-CD16, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG. In some aspects, the fluorophore is selected from among DyLight488, a Brilliant Violet dye, Pacific Blue, Krome Orange, Brilliant Blue 515, PE, FITC, PerCPCy5.5, PerCP, PE-Cy5.5, PE-Cy7, APC, Alexa647, AlexaFluor647, APC-Alexa700 and APC-Alexa750.

In certain aspects, the methods provided herein are for simultaneously analyzing a plurality of particles of different size and/or having different molecular markers. In some aspects, the different molecular markers can simultaneously be detected according to the methods provided herein, using optically detectable labels that are distinct from one another for each of the different molecular markers. In aspects, for multispectral analysis of a plurality of particles having a plurality of molecular markers, provided herein is a panel of optical standard particles, each conjugated to a distinct optically detectable label or associated with a distinct molecular marker conjugated to a distinct optically detectable label whereby, based on the measured optical intensities of the panel of optical standard particles, the optical intensities of the corresponding optically detectable labels associated with the particles or associated with the molecular markers of the particles are measured with improved accuracy (e.g., by facilitating "spectral unmixing"). In some aspects, the analysis is by flow cytometry. In aspects, the panel of optical standard particles includes fluorescent beads. In some aspects, the panel of optical standard particles includes beads that can bind to or otherwise associate with ligands, which in turn can be labeled with a fluorophore. In aspects, the ligand is an antibody. In aspects, the antibody is selected from among anti-CD20, anti-CD3, anti-CD5, anti-CD56, anti-CD13, anti-CD4, anti-CD8, anti-CD19, anti-CD16, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG. In some aspects, the fluorophore is selected from among DyLight488, a Brilliant Violet dye, Pacific Blue, Chrome Orange, Krome Orange, Brilliant Blue 515, PE, FITC, PerCPCy5.5, PerCP, PE-Cy5.5, PE-Cy7, APC, Alexa647, AlexaFluor647, APC-Alexa700 and APC-Alexa750.

The size of an optical standard particle for use in the methods provided herein can be between about 20 nm to about 1, 2, 3, 4, 5, 10 or more microns. In some aspects, the size of the optical standard particle is between about 20 nm to about 5 microns, about 30 nm to about 3 microns, about 40 nm to about 2 microns, about 50 nm to about 1 micron, about 50 nm to about 500 nm, about 50 nm to about 450 nm, about 50 nm to about 400 nm, about 100 nm to about 450 nm, or about 100, 110, 120, 130, 140, 150, 160, 170,180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nm.

In aspects of the methods provided herein, an optical standard particle that is not associated with an optically detectable label can be used, thereby improving accuracy by correcting the background optical signal obtained from the particle alone. In certain aspects, the optical standard particle is a bead. In aspects, the bead is coated with, bound to, or otherwise associated with a molecule. In some aspects, the molecule is a polymer. In certain aspects, the polymer is polyethylene glycol (PEG). In aspects, the polymer is a protein that does not associate with an optically detectable label. In certain aspects, the protein is BSA.

Biological Particles

Biological particles that can be analyzed using systems and methods provided herein include, for example, cells, cell products, cell components, cell compartments, extracellular vesicles (EVs), cell-derived vesicles (exosomes, endosomes, unilamellar vesicles, multilamellar vesicles), liposomes, lipoproteins, microparticles, nanoparticles, viruses, viral particles, virus-like particles, apoptotic bodies, and other particles. A particle can include a lipid bilayer. For example, a particle containing a lipid bilayer can be a membrane vesicle, a lipoprotein, a liposome or an extracellular vesicle. Biological particles can be derived from human cells, animal cells, plant cells, bacteria, viruses, and the like. Biological particles can be present in a sample, and can include one or more markers, tags, and/or stains. Biological particles can be capable of emitting light and/or exhibiting luminescence (e.g., fluorescence, phosphorescence, chemiluminescence, and the like). Inert particles that can be analyzed using systems and methods provided herein include metalloids, non-limiting examples of which include boron and silicon, the like and combinations thereof.

Membrane Vesicles

In embodiments, the particles analyzed by the systems and methods provided herein include membrane vesicles. A membrane vesicle, as used herein, refers to a particle that includes fluid enclosed within a lipid-containing outer shell. The enclosed fluid can include additional components, such as proteins and small molecules. A lipid molecule typically includes at least one hydrophobic chain and at least one polar head. When exposed to an aqueous environment, lipids often will self-assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A vesicle also can be a lipid bilayer configured as a spherical shell enclosing a small amount of water or aqueous solution and separating it from the water or aqueous solution outside the vesicle. Membrane vesicles also can contain a fluid with, optionally, one or more molecular components, enclosed within a lipid bilayer. Because of the fundamental similarity to a cell wall, vesicles have been used to study the properties of lipid bilayers. Vesicles also are readily manufactured. A sample of dehydrated lipid spontaneously forms vesicles, when exposed to water. Spontaneously formed vesicles can be unilamellar (single-walled) or multilamellar (many-walled) and are of a wide range of sizes from tens of nanometers to several micrometers. A lipid bilayer typically includes a sheet of lipids, generally two molecules thick, arranged so that the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect and are held together by non-covalent forces that do not involve formation of chemical bonds between individual molecules.

In some embodiments, lipid bilayers are natural, and in certain embodiments lipid bilayers are artificially generated. Natural bilayers often are made mostly of phospholipids, which have a hydrophilic head and two hydrophobic tails (e.g., lipid tails), and form a two-layered sheet as noted above, when exposed to water or an aqueous environment. The center of this bilayer contains almost no water and also excludes molecules like sugars or salts that dissolve in water, but not in oil. Lipid tails also can affect lipid composition properties, by determining the phase of the bilayers, for example. A bilayer sometimes adopts a solid gel phase state at lower temperatures and undergoes a phase transition to a fluid state at higher temperatures. Artificial bilayers of membrane vesicles can be any bilayers assembled through artificial means, as opposed to bilayers that occur naturally (e.g., cell walls, lipid bilayers that cover various sub-cellular structures).

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of bilayer constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), phosphosphingolipids, glycolipids including gangliosides, surfactants, the like and combinations thereof.

Different types or forms of lipid compositions (e.g., monolayers and/or bilayers) can be found naturally or generated artificially. Non-limiting examples of lipid compositions include monolayers (e.g., micelles), supported lipid bilayers, linear lipid bilayers and the like.

A protein, glycoprotein, glycolipid, nucleic acid or carbohydrate often is inserted into a structure (e.g., monolayer and/or bilayer) formed by the lipid or amphiphilic material composition, or is encapsulated within the interior of the structure (membrane vesicle or other particle as described herein). A protein that is inserted into the structure can be water soluble, detergent-solubilized or incorporated into a lipid bilayer (e.g., vesicle, liposome) or a lipid monolayer (e.g., micelle) in some embodiments.

Some types of membrane vesicles can include lipoproteins, endosomes, apoptotic bodies, viruses, virus particles and virus-like particles. Endosomes are membrane-bound vesicles, formed via a complex family of processes collectively known as endocytosis, and found in the cytoplasm of virtually every animal cell. The basic mechanism of endocytosis is the reverse of what occurs during exocytosis or cellular secretion or the release of extracellular vesicles (EVs, e.g., ectosomes, exosomes) as it involves the invagination (folding inward) of a cell's plasma membrane to surround macromolecules or other matter diffusing through the extracellular fluid. The encircled foreign materials are then brought into the cell, and following a pinching-off of the membrane (termed budding), are released to the cytoplasm of the cell in a sac-like vesicle. The sizes of the endosomal vesicles can vary and generally are nanoparticles. Endosomes larger than 100 nanometers in diameter typically are referred to as vacuoles.

Viruses, virus particles and virus-like particles can include a lipid bilayer and, in embodiments, carry proteins on their surface, including envelope proteins, coat proteins and cellular membrane proteins. "Naked viruses" generally lack surface proteins and can be modified to include surface proteins (e.g., by insertion of the proteins into the outer lipid bilayer of the virus). Viruses include for example, but are not limited to, retroviruses and DNA viruses. Virus particles can include the fully or partially assembled capsid of a virus. A viral particle may or may not contain nucleic acid. Virus particles generally include one or more of or two or more of the following: genetic material made from either DNA or RNA; a protein coat that protects the genetic material; and in some embodiments an envelope of lipids that surrounds the protein coat when they are outside a cell.

Lipoproteins are globular, micelle-like particles that include a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver. Lipoprotein particles undergo continuous metabolic processing and can have variable properties and compositions. Lipoprotein densities can increase without decreasing particle diameter because the density of their outer coatings is less than that of the inner core. The protein components of lipoproteins are known as apolipoproteins. At least nine apolipoproteins are distributed in significant amounts among the various human lipoproteins.

Apoptotic bodies are released during apoptosis (programmed cell death). When a cell undergoes apoptosis, the structure of the cell breaks down. The breakdown components are packaged into apoptotic bodies, which can include membrane bound "sacs" that contain nucleic acids, proteins and lipids. When the ability of neighboring cells and/or macrophages to clear these breakdown components is overwhelmed by high numbers of apoptotic bodies ("excessive" apoptosis) or defects in clearing the bodies, apoptotic bodies are released into circulation and can be detected in blood plasma or serum (Holdenrieder et al, 2001a; Holdenrieder et al, 2001b; Holdenrieder et al, 2001c; Lichtenstein et al, 2001). Above-average levels of apoptotic bodies in the bloodstream have been correlated, e.g., with the presence tumors and cancers. An "apoptotic body" can contain nucleic acids, proteins, lipids, but no nucleus, although it may contain fragmented nuclei. In general, apoptotic bodies are less than 10 microns in size, generally between about 25 nm, 50 nm, 75 nm or 100 nm to about 150 nm, 200 nm, 250, 300 nm, 350 nm, 400 nm, 400 nm, 500 nm, 1 micron, 1.5 micron, 2 microns, 2.5 microns, 3 microns, 3.5 microns, 4 microns, 4.5 microns or 5 microns in size.

Liposomes

In embodiments, the particles analyzed by the systems and methods provided herein include liposomes. A liposome is an artificially prepared vesicle that includes at least one lipid bilayer and also can be made of naturally occurring or synthetic lipids, including phospholipids. Liposomes can include MLV (multilamellar vesicles), SUV (Small Unilamellar Vesicles), LUV (Large Unilamellar Vesicles) and GUV (Giant Unilamellar Vesicles). Unilamellar vesicles generally contain a single lipid bilayer, while multilamellar vesicles generally include more than one lipid bilayer. As used herein, "multivesicular liposome" refers to man-made, microscopic lipid vesicles containing lipid membranes enclosing multiple concentric or non-concentric aqueous chambers.

Various types of lipids can be used to make liposomes, including neutral lipids and amphipathic lipids. Examples of neutral lipids include diglycerides, such as diolefin, dipalmitolein; propylene glycol esters such as mixed diesters of caprylic/capric acids on propylene glycol; triglycerides such as triolein, tripalmitolein, trilinolein, tricaprylin and trilaurin; vegetable oils, such as soybean oil; lard or beef fat; squalene; tocopherol; and combinations thereof. Examples of amphipathic lipids include those with net negative charge, zero net charge, and net positive charge at pH 7.4. These include zwitterionic, acidic or cationic lipids. Such representative amphipathic lipids include, but are not limited to, phosphatidylglycerol (PG), cardiolipin (CL), phosphatidylserine (PS), phosphatidic acid (PA), phosphatidylinositol, phosphatidylcholine (PC), phosphatidylethanolamine (PE), sphingomyelin, diacyl trimethylammonium propane (DITAP), DOPC or DC18:1PC=1,2-dioleoyl-sn-glycero-3-phosphocholine; DLPC or DC12:0PC=1,2-dilauroyl-sn-glycero-3-phosphocholine; DMPC or DC14:0PC=1,2-dimyristoyl-sn-glycero-3-phosphocholine; DPPC or DC16:0PC=1,2-dipalmitoyl-sn-glycero-3-phosphocholine; DSPC or DC18:0PC=1,2-distearoyl-sn-glycero-3-phosphocholine; DAPC or DC20:0PC=1,2diarachidoyl-sn-glycero-3-phosphocholine; DBPC or DC22:0PC=1,2-dibehenoyl-sn-glycero-3-phosphocholine; DC14:1PC=1,2-dimyristoleoyl-sn-glycero-3-phosphocholine; DC16:1PC=1,2-dipalmitoleoyl-sn-glycero-3-phosphocholine; DC20:1PC=1,2-dieicosenoyl-sn-glycero-3-phosphocholine; DC22:1PC=1,2-dierucoyl-sn-glycero-3-phosphocholine; DPPG=1,2-dipalmitoyl-sn-glycero-3-phosphoglycerol; DOPG=1,2-dioleoyl-sn-glycero-3-phosphoglycerol and combinations thereof. Additionally, lipoproteins, gangliosides, cholesterol or plant sterols can be used to make, or are a part of, liposomes.

Some examples of lipid-polymer conjugates and liposomes are disclosed in U.S. Pat. No. 5,631,018, which is incorporated herein by reference in its entirety. Examples of processes to make multilamellar and unilamellar liposomes are known in the art (see e.g. U.S. Pat. Nos. 4,522,803, 4,310,506, 4,235,871, 4,224,179, 4,078,052, 4,394,372, 4,308,166, 4,485,054 and 4,508,703).

Extracellular Vesicles

In embodiments, the particles analyzed by the systems and methods provided herein include extracellular vesicles (EVs). The term "extracellular vesicles," as used herein, can include membrane vesicles secreted from cell surfaces (ectosomes), internal stores (exosomes), cancer cells (oncosomes), or released as a result of apoptosis and cell death. In addition to lipid membranes, depending on their cell or tissue of origin, EVs can include additional components such as lipoproteins, proteins, nucleic acids, phospholipids, amphipathic lipids, gangliosides and other particles contained within the lipid membrane or encapsulated by the EVs.

All cells likely release EVs, making them attractive clinical diagnostic and therapeutic targets for a range of diseases. Non-limiting examples of normal or cancer cell types that can release EVs include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney cells, heart cells, muscle cells, blood cells (e.g., white blood cells, platelets), the like and combinations of the foregoing. Because EVs are involved in cell-cell communication, their characterization casts light upon their role in normal physiology and pathology. EVs in biological fluids including saliva, urine and sera are being interrogated as biomarkers of ovarian, lung, bladder and prostate cancers.

Glioblastoma is the most common form of primary brain cancer and is one of the deadliest of human cancers. Glioblastoma cells release extracellular vesicles (EVs) containing amplified and mutated genetic materials derived from the tumor. The circulating EVs significantly exceed tumor-derived circulating tumor cells and tumor derived circulating DNA and RNA. The released EVs appear in the local environment, the sera and cerebrospinal fluid (CSF). Amplification of EGFR is the most frequent genetic abnormality associated with GBM, and EGFR overexpression has been shown in up to 40% of cases. GBM also often expresses EGFRvIII, a genomic deletion variant of EGFR that is constitutively active and oncogenic. Thus, the analyses of GBM EVs offer a potential tool for monitoring tumor presence, phenotypic/genotypic features, and pathophysiology.

EVs are abundant in various biological fluids, including blood, urine, and cerebrospinal fluid, but because they are released by different mechanisms and by many different cell types, EVs in biofluids can be heterogeneous. While multi-spectral optical methods can detect vesicles that have different molecular markers, the small average size of EVs can result in small optical signals from labels bound to or otherwise associated with these small particles, making it a challenge to analyze the EVs by optical methods.

EVs can be released by all normal and cancer cells. With a mean diameter of ~100-200 nm, however, individual EVs have ~$\frac{1}{10,000}$ the surface area and ~$\frac{1}{1,000,000}$ the volume of a whole cell, making them difficult to detect using available single cell analysis tools, including conventional flow cytometry. As a result, most proteomic and genomic analysis is performed in bulk on thousands or millions of EVs. However, EVs in biofluids come from many different cell types, and from different locations from within the cell (exosomes secreted from intracellular multi-vesicular bodies, ectosomes/microvesicles shed from the plasma membrane surface, membrane fragments released as a result of cell apoptosis, necrosis, etc). Thus, in a bulk analysis, the signature from tumor EVs may be lost in the background of vesicles from other sources. Single EV measurement approaches such as nanoparticle tracking analysis (NTA) and resistive pulse sensing (RPS) can report particle concentrations but provide no information on the cell of origin. Thus, provided herein are methods of analyzing EV particles wherein the EV particles are characterized for their size, quantity, number of associated specific molecular markers and/or cell/tissue of origin.

Inert Particles

In certain embodiments, the particles analyzed by the systems and methods provided herein include inert particles that can associate with an optically detectable label or can be modified for association with an optically detectable label. Such particles can include metalloids, non-limiting examples of which include boron and silicon, the like and combinations thereof. A particle sometimes can include, consist essentially of, or consist of, silica (e.g., silicon dioxide (i.e., $SiO_2$)). A particle sometimes can include one or more metals including, but not limited to, iron, gold, copper, silver, platinum, aluminum, titanium, tantalum, vanadium, the like, oxides thereof and combinations thereof. A particle sometimes can include glass (e.g. controlled-pore glass (CPG)), nylon, Sephadex®, Sepharose®, cellulose, a magnetic material or a plastic material. A particle sometimes is a polymer or includes more than one polymer. Non-limiting examples of polymers include polypropylene (PP), polyethylene (PE), polyamide, high-density polyethylene (HDPE), low-density polyethylene (LDPE), polyester, polyvinylidenedifluoride (PVDF), polyethylene teraphthalate (PET), polyvinyl chloride (PVC), polytetrafluoroethylene (PTFE), polystyrene (PS), high-density polystyrene, acrylnitrile butadiene styrene copolymers, crosslinked polysiloxanes, polyurethanes, (meth)acrylate-based polymers, cellulose and cellulose derivatives, polycarbonates, ABS, tetrafluoroethylene polymers, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyorthoesters, polycyanoacrylates, polycaprolactone, the like, copolymers thereof and combinations of the foregoing.

2. Shapes/Sizes of Particles

The particles analyzed by the systems and methods provided herein can be solid particles or particles that contain internal voids. The particles can have a regular (e.g., spheroid, ovoid) or irregular shape (e.g., rough, jagged), and sometimes can be non-spherical (e.g., angular, multi-sided).

The size of the particles (e.g., inert particles, liposomes or EVs) analyzed according to the methods provided herein can include particles in the size range (average length, width or diameter) of about or at 10 nm to about or at 5 microns, but generally are in the range of about or at 50 nm to about or at 100, 125, 150, 175, 200, 250, 300, 350, 400, 450, 500, 550, 600, 650, 700, 750, 800, 850, 900 or 950 nm or 1.0 to 1.5, 2.0, 2.5, 3.0, 3.5, 4.0, 4.5 or 5.0 microns. Any particle in the size range of nm to microns or larger can be analyzed according to the systems and methods provided herein. In certain aspects, a particle is a nanoparticle of less than 1 micron in diameter. In some embodiments, nanoparticles in a sample can include at least one particle with a size of about 500 nm or less in diameter, between about 10 nm to about 200 nm in diameter, between about 50 nm to about 200 nm in diameter, between about 50 nm to about 150 nm in diameter, between about 10 nm to about 500 nm in diameter, between about 50 nm to about 200 nm in diameter, or between about 50 nm to about 150 nm in diameter.

3. Analysis of Particles

Analyzing particles in a sample can include detecting, quantitating, determining one or more of the type, size and/or shape of the particle, classifying the particle according to its properties, and the like. In general, "analyzing particles," as used herein, refers to the analysis of individual particles in a sample, based on detecting an individual particle at a time. In certain aspects, analyzing particles in a sample can include determining the surface area and/or volume of the particle based on a detected optical signal of one or more particle-associated surface area probes or volume probes, respectively. A probe can be an optically detectable molecular marker or other optically detectable marker that is intrinsic to the particle, or it can be an extrinsic probe that is added to the particle and becomes associated with the particle, such as a chromophore or fluorophore, or the particle can have both intrinsic and extrinsic probes or molecular markers that are analyzed. In some aspects, the size of a particle can be determined based on the surface area or volume. In certain aspects, determining the size of a particle can include determining the diameter of the particle.

In some embodiments, analyzing particles in a sample can include determining the type and/or number of intrinsic and/or extrinsic molecular markers or other probe(s) associated with a particle, based on the detected optical signal of the probe. In some aspects, a particle can be identified and/or quantified based on the type and/or number of probes associated with the particle. The terms "associated," "associated with" or "interact," can be used interchangeably with "bound" or "containing," e.g., "lipid-containing particle," and can refer to a variety of different types of contact between, for example, a particle and its components (lipids, proteins, nucleic acids, carbohydrates, glycoproteins, glycolipids, phospholipids, phosphosphingolipids, and the like), or between a particle and an optically detectable label that can include, but is not limited to, covalent bonds or non-covalent interactions, non-limiting examples of which include van der Waals interactions, hydrogen bonding, ionic interactions, electrostatic interactions and/or hydrophilic or hydrophobic interactions. In some embodiments, a molecule that is the probe is also an optically detectable label and in certain embodiments, a molecule that is the probe (e.g., a molecular marker) is detected using an extrinsically added optically detectable label.

With respect to the interaction of membrane vesicles, liposomes, extracellular vesicles and other lipid bilayer or lipid membrane containing particles with an optically detectable label, the terms "associated," "associated with" or "interact," as used herein, also can refer to intercalation of an optically detectable label into the membrane, or binding of the optically detectable label to a molecular marker within or at the surface of the membrane vesicles, liposomes, extracellular vesicles and other lipid bilayer or lipid membrane containing particles. The term "free" or "unbound," as used herein, refers to molecules, including optically detectable labels, which are not in contact with a particle. "Free" or "unbound" optically detectable label, e.g., in the staining solution, generally is detected as a background signal or no signal, relative to the higher signal intensity of the optically detectable label when it is associated with a particle (i.e., a particle-associated surface area probe or volume probe, or a particle-associated molecular marker-specific probe).

Representative optically detectable labels can include, for example, chromophores, chemiluminescent moieties, bioluminescent moieties, fluorescent moieties and metals. Such labels can be detected, for example, by visual inspection, by spectroscopy, by fluorescence spectroscopy, by fluorescence imaging (e.g., using a fluorescent microscope or fluorescence stereomicroscope), by flow cytometry and the like.

In embodiments, the optically detectable label can be conjugated to a molecule (e.g., a protein, an antibody, a lectin, a peptide, a nucleic acid, a carbohydrate, a glycan and the like) that binds to or otherwise associates with a molecular marker on the particle, or associates with/intercalates into the particle membrane (e.g., when the particle is a vesicle, liposome or EV).

Representative chromophores include, but are not limited to, 3,3'-diaminobenzidine (DAB); 3-amino-9-ethyl carbazole (AEC); Fast Red; FD&C Yellow 5 (Tartrazine); Malachite Green Carbinol hydrochloride; Crocein Scarlet 7B (Dark Red); Erioglaucine (Dark Blue); Crystal Violet (Dark Purple); Bromophenol Blue; Cobalt(II) Chloride Hexahydrate (Red); Basic Violet 3; Acid Blue 9; Acid Red 71; FD&C Blue 1 (Brilliant Blue FCF); FD&C Red 3 (Erythrozine); and FD&C Red 40 (Allura Red AC). Representative fluorophores include, but are not limited to, di-8-ANEPPS, di-4-ANEPPS, a carbocyanine dye (e.g., DiO, DiL), a PKH dye, Dylight488, Brilliant Violet, Pacific Blue, Chrome Orange, Krome Orange, Brilliant Blue 515, phycoerythrin (PE), rhodamine, fluorescein, FITC, PE-Cy5.5, PE-Cy7, APC, Alexa647, APC-Alexa700 and APC-Alexa750, Oregon Green®, derivatives of rhodamine (e.g., Texas Red and tetrarhodimine isothiocynate (TRITC)), AMCA, Alexa Fluor®, Li-COR®, CyDyes® or DyLight® Fluors); tdTomato, mCherry, mPlum, Neptune, TagRFP, mKate2, TurboRFP and TurboFP635 (Katushka). The fluorescent reagent can be chosen based on desired excitation and emission spectra. Also representative of fluorescent reagents are macromolecules that emit an optically detectable signal, including fluorescent proteins, such as a green fluorescent protein (GFP) or a red fluorescent protein (RFP). A variety of DNA sequences encoding proteins that can emit a detectable signal or that can catalyze a detectable reaction, such as luminescent or fluorescent proteins, are known and can be used in the methods provided herein. Representative genes encoding light-emitting proteins include, for example, genes from bacterial luciferase from *Vibrio harveyi* (Belas et al., (1982) *Science* 218:791-793), bacterial luciferase from *Vibrio fischerii* (Foran and Brown, (1988) *Nucleic acids Res.* 16:177), firefly luciferase (de Wet et al., (1987) *Mol. Cell. Biol.* 7:725-737), aequorin from *Aequorea victoria* (Prasher et al., (1987) *Biochem.* 26:1326-1332), *Renilla* luciferase from *Renilla renformis* (Lorenz et al, (1991) *Proc Natl Acad Sci USA* 88:4438-4442) and green fluorescent protein from *Aequorea victoria* (Prasher et al., (1987) *Gene* 111:229-233). The luxA and luxBgenes of bacterial luciferase can be fused to produce the fusion gene (Fab$_2$), which can be expressed to produce a fully functional luciferase protein (Escher et al., (1989) *PNAS* 86: 6528-6532).

In some embodiments, a surface area probe or volume probe is a fluorescent label. In some aspects, a molecular marker-specific probe is a fluorescent label. Any fluorescent label can be used herein including, but not limited to, a fluorophore, a tandem conjugate between more than one fluorophore, a fluorescent polymer, a fluorescent protein, or a fluorophore conjugated to a molecule that interacts with one or more particles of the sample.

In some aspects, a molecule that interacts with one or more particles of the sample includes, but is not limited to, a protein, an antibody, a lectin, a peptide, a nucleic acid, a carbohydrate or a glycan. The molecule can interact with a particle in a manner that is proportional to the surface area or volume of the particle or can bind or otherwise associate specifically with one or more molecular markers on the particle. In some embodiments, the molecule that interacts with one or more particles of a sample is an antibody, or a molecular marker-binding/associating fragment thereof. Antibodies generally bind to specific antigens and contain two identical heavy chains and two identical light chains covalently linked by disulfide bonds. In certain aspects, an antibody or portion thereof is conjugated to a fluorophore. An antibody can be selected from among anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54, anti-CD45 and anti-IgG, for example.

A fluorophore (e.g., conjugated to an antibody) can be selected from among DyLight488, a Brilliant Violet dye (representative of which are BV-421, BV-510, BV-605 and the like), Pacific Blue, Chrome Orange, Krome Orange, Brilliant Blue 515, PE, FITC, PE-Cy5.5, PE-Cy7, APC, Alexa647, APC-Alexa700 and APC-Alexa750, for example.

In some embodiments, a molecular marker-specific probe is a fluorophore conjugated to a protein. A protein can be selected from among annexin V, cholera toxin B-subunit, anti-CD61, anti-CD171, anti-CD325, anti-CD130, anti-GLAST, anti-EGFRvIII, anti-EGFR, anti-CD133, anti-CD15, anti-CD63, anti-CD9, anti-CD41, anti-CD235, anti-CD54 and anti-CD45, for example. A fluorophore (e.g., conjugated to a protein) may be selected from among Dylight488, a Brilliant Violet dye, Pacific Blue, Chrome Orange, Krome Orange, Brilliant Blue 515, PE, rhodamine, FITC, PE-Cy5.5, PE-Cy7, APC, Alexa647, APC-Alexa700 and APC-Alexa750, for example.

A sample can be prepared for analysis of the particles therein by labeling the particles therein with a probe, such as a light emitting agent or optically detectable label as described herein. Optically detectable labels can include, for example, chromophores, chemiluminescent moieties, bioluminescent moieties, fluorescent moieties and metals. As described above, an optically detectable label can be conjugated to a molecule (e.g., a protein, an antibody, a lectin, a peptide, a nucleic acid, a carbohydrate, a glycan and the like) that binds to or otherwise associates with a molecular marker on a particle, or associates with and/or intercalates into a particle membrane (e.g., when the particle is a vesicle, liposome or EV). More than one optically detectable label can be used to label the particles in the sample, for example, according to size, shape, type, abundance or other property.

Certain Implementations

Following are non-limiting examples of certain implementations of the technology.

A1. A method for analyzing a particle in a flow cytometer, comprising:
- (a) introducing a sample comprising one or more particles to a flow channel comprising a plurality of measurement subzones;
- (b) sequentially illuminating the measurement subzones in the flow channel as each of the one or more particles flows through the flow channel, wherein:
  - each of the measurement subzones is illuminated with a wavelength of light different than for the other measurement subzones,
  - each of the measurement subzones is illuminated when a particle is located therein and each of the measurement subzones is not illuminated when a particle is not located therein, and
  - a particle emits light in response to being illuminated in at least one of the measurement subzones;
- (c) collecting and delivering light emitted by the one or particles in one or more of the measurement subzones to a detector; and
- (d) detecting light emitted by the one or more particles, thereby analyzing the particle.

A1.1 The method of embodiment A1, comprising sequentially generating a plurality of illumination volumes when the measurement subzones are sequentially illuminated in (b).

A2. The method of embodiment A1 or A1.1, wherein (c) comprises delivering light emitted by the illuminated particle as a composite signal to an optical element.

A3. The method of embodiment A2, wherein the optical element (i) selectively obtains a subset of component discrete wavelength signals from the composite signal, (ii) dispersively separates the composite signal into component spectral signals, or (iii) a combination of (i) and (ii), whereby the composite signal is separated into component signals.

A4. The method of embodiment A3, wherein (i) the optical element selectively obtains a subset of component discrete wavelength signals from the composite signal, and (ii) the selectively obtained subset of component discrete wavelength signals are analyzed, whereby the particle is analyzed.

A5. The method of embodiment A3, wherein (i) the optical element dispersively separates the composite signal into component spectral signals, and (ii) the component spectral signals from the composite signal of a single measurement subzone are analyzed, whereby the particle is analyzed.

A6. The method of embodiment A3, wherein (i) the optical element dispersively separates the composite signal into component spectral signals, and (ii) the component spectral signals from the composite signal of more than one measurement subzone are simultaneously analyzed, whereby the particle is analyzed.

A7. The method of any one of embodiments A1 to A6, wherein (b) comprises sequentially activating and deactivating a plurality of light sources, wherein each of the light sources illuminates each of the measurement subzones.

A8. The method of embodiment A7, wherein (b) comprises activating and deactivating each switch in a plurality of switches, wherein each of the switches is configured to activate and deactivate each of the light sources, and (ii) activating each of the light sources in the plurality of light sources one at a time while each of the other light sources is deactivated.

A9. The method of embodiment A7 or A8, wherein (b) comprises sequentially activating one of the light sources after deactivating one of the other light sources.

A10. The method of any one of embodiments A1 to A9, wherein the measurement subzones are positioned linearly in the direction of fluid flow in the flow channel.

A11. The method of embodiment A10, wherein (b) comprises (i) activating a light source that illuminates a measurement subzone, while all other light sources are deactivated; (ii) deactivating the light source that illuminates the measurement subzone illuminated in (i) and activating a light source that illuminates a measurement subzone located next to the measurement subzone illuminated in (i) and closer to an outlet in the flow channel, while all other light sources are deactivated, and (iii) repeating (i) and (ii) until a light source that illuminates a measurement subzone closest to the flow channel outlet is activated and then deactivated.

A12. The method of any one of embodiments A1 to A11, wherein (b) comprises (i) detecting the presence of a particle in a measurement subzone closest to an inlet in the flow channel, and (ii) transmitting a signal to sequentially activate and deactivate light sources.

A13. The method of any one of embodiments A7 to A12, wherein (b) comprises delivering light from the light sources to the flow channel.

A14. The method of embodiment A13, wherein light is delivered from the light sources to the flow channel through an optical fiber or a plurality of optical fibers.

A15. The method of embodiment A13 or A14, wherein delivering light from the light sources to the flow channel comprises use of shaping optic, or a focusing optic, or a shaping optic and focusing optic.

A16. The method of any one of embodiments A7 to A15, wherein the collecting in (c) comprises use of a collector positioned parallel to the direction of light emitted from the light sources.

A17. The method of any one of embodiments A7 to A16, wherein the collecting in (c) comprises use of a collector positioned orthogonal to the direction of light emitted from the light sources.

A18. The method of embodiment A17, wherein the collector is located at a position (i) proximal to the flow channel, (ii) distal to the flow channel, or (iii) a combination of (i) and (ii).

A19. The method of any one of embodiments A7 to A18, wherein the collecting in (c) comprises use of at least two collectors.

A20. The method of embodiment A19, comprising use of two collectors positioned (i) orthogonal to the direction of light emitted by the light sources, (ii) opposite to one another, and (iii) proximal to the flow channel and distal to the flow channel.

A21. The method of any one of embodiments A16 to A20, wherein the delivering in (c) comprises delivering light from one or more collectors to (i) a selective optical element, (ii) a dispersive optical element, or (iii) a combination of (i) and (ii).

A22. The method of embodiment A21, wherein light is delivered from a collector to (i) the selective optical element, (ii) the dispersive optical element, or (iii) a combination of (i) and (ii) through one optical fiber or a plurality of optical fibers.

A23. The method of embodiment A21, wherein light is delivered from two collectors to (i) the selective optical element, (ii) the dispersive optical element, or (iii) a combination of (i) and (ii) through a plurality of optical fibers.

A24. The method of embodiment A23, comprising combining the light from two collectors.

A25. The method of embodiment A23, comprising combining the light from two collectors and delivering the combined light from the two collectors to (i) the selective optical element, (ii) the dispersive optical element, or (iii) a combination of (i) and (ii).

A26. The method of any one of embodiments A23 to A25, comprising 1) delivering light emitted from the measurement subzone closest to the flow channel inlet obtained from both collectors to the selective optical element; and 2) delivering light emitted from the remaining measurement subzones obtained from both collectors to the dispersive optical element.

A27. The method of any one of embodiments A23 to A25, comprising 1) delivering light emitted from the measurement subzone closest to the flow channel inlet obtained from a first collector module to the selective optical element; and 2) delivering light emitted from some or all measurement subzones obtained from a second collector module to the dispersive optical element.

A28. The method of any one of embodiments A23 to A25, comprising 1) delivering light emitted from the measurement subzone closest to the flow channel inlet obtained from a first collector module to the selective optical element; 2) delivering light emitted from the remaining measurement subzones obtained from the first collector to the dispersive optical element; and 3) delivering light emitted from some or all measurement subzones obtained from a second collector module to the dispersive optical element.

A29. The method of any one of embodiments A1 to A28, wherein (d) comprises use of one or more of a lens, photomultiplier tube (PMT), filter, slit, prism and grating.

A30. The method of embodiment A29, wherein the filter comprises (i) a bandpass filter, (ii) a notch filter, or combination of (i) and (ii).

A31. The method of embodiment A29 or A30, wherein the lens comprises (i) a collimating lens, (ii) a focusing lens, or combination of (i) and (ii).

A32. The method of any one of embodiments A21 to A31, wherein the selective optical element comprises a PMT.

A33. The method of any one of embodiments A21 to A32, wherein the dispersive optical element comprises a prism, or a grating, or a prism and a grating.

A34. The method of any one of embodiments A1 to A33, comprising analyzing light detected in (d).

A35. The method of embodiment A34, wherein (d) comprises use of a selective optical element, and wherein analyzing light detected in (d) comprises analyzing a selective subset of component signals obtained by the selective optical element.

A36. The method of embodiment A34 or A35, wherein (d) comprises use of a dispersive optical element, and wherein analyzing light detected in (d) comprises (i) analyzing component spectral signals from a composite output signal of a single measurement subzone, (ii) simultaneously analyzing component spectral signals from a composite output signal of a plurality of measurement subzones, or (iii) a combination of (i) and (ii).

B1. A flow cytometry system, comprising:
   a flow channel comprising an inlet and an outlet and a plurality of measurement subzones;
   a fluidics module comprising a fluid delivery line to the flow channel inlet and fluid emission line from the flow channel outlet;
   an illumination module comprising a plurality of light sources and a light source synchronizer, wherein:
      each of the light sources emits light of a different wavelength; and
      each of the light sources is in communication with a measurement subzone located at a different location in the flow channel;
   a light collector module in communication with the measurement subzones of the flow channel;
   a detector module; and
   a light transmission module connected to the light collector module and the detector module.

B11.1 The flow cytometry system of embodiment B1, wherein the light source synchronizer comprises a controller and a plurality of switches.

B11.2 The flow cytometry system of embodiment B11.1, wherein each of the switches is in separate communication with each of the light sources.

B2. The flow cytometry system of embodiment B11.1 or B11.2, wherein the controller in the light source synchronizer is configured to sequentially activate and deactivate each of the light sources.

B3. The flow cytometry system of embodiment B2, wherein the controller in the light source synchronizer is configured to (i) activate and deactivate each of the switches, and (ii) activate each of the light sources one at a time while each of the other light sources is deactivated.

B4. The flow cytometry system of embodiment B2 or B3, wherein the controller in the in the light source synchronizer is configured to sequentially activate one of the light sources after deactivating one of the other light sources.

B5. The flow cytometry system of any one of embodiments B1-B4, wherein the measurement subzones are disposed at discrete positions in the flow channel and are disposed linearly in the direction of fluid flow in the flow channel.

B6. The flow cytometry system of embodiment B5, wherein the controller in the light source synchronizer is configured to (i) activate a light source that illuminates a measurement subzone, while all other light sources are deactivated; (ii) deactivate the light source that illuminates the measurement subzone illuminated in (i) and activate a light source that illuminates a measurement subzone located next to the measurement subzone illuminated in (i) and closer to the flow channel outlet, while all other light sources are deactivated, and (iii) repeat (i) and (ii) until a light source that illuminates a measurement subzone closest to the flow channel outlet is activated and then deactivated.

B7. The flow cytometry system of any one of embodiments B1.1-B6, wherein the illumination module is in connection with a gate configured to: (i) detect the presence of a particle in a measurement subzone closest to the flow channel inlet, and (ii) transmit a signal to the controller in the light source synchronizer to sequentially activate and deactivate light sources.

B7.1 The flow cytometry system of any one of embodiments B1-B7, wherein the illumination module is configured to sequentially generate a plurality of illumination volumes when each of the measurement subzones are sequentially illuminated.

B8. The flow cytometry system of any one of embodiments B1-B7.1, wherein the illumination module comprises 2, 3, 4, 5, 6, 7, 8, 9, 10, 11, 12, 13, 14, 15, 16, 17, 18, 19 or 20 light sources.

B9. The flow cytometry system of any one of embodiments B1-B8, wherein the illumination module comprises a light delivery module connected to the light sources and the flow channel.

B10. The flow cytometry system of embodiment B9, wherein the light delivery module comprises an optical fiber or plurality of optical fibers.

B11. The flow cytometry system of embodiment B9 or B10, wherein the light delivery module comprises a shaping optic, or a focusing optic, or a shaping optic and focusing optic.

B12. The flow cytometry system of any one of embodiments B1-B11, wherein the collector module comprises a collector positioned parallel to the direction of light emitted from the light sources.

B13. The flow cytometry system of any one of embodiments B1-B12, wherein the collector module comprises a collector orthogonal to the direction of light emitted from the light sources.

B14. The flow cytometry system of embodiment B13, wherein the collector module comprises a collector located at a position (i) proximal to the flow channel, (ii) distal to the flow channel, or (iii) a combination of (i) and (ii).

B15. The flow cytometry system of any of embodiments B1-B14, wherein the collector module comprises at least two collectors.

B16. The flow cytometry system of embodiment B15, wherein the collector module comprises two collectors positioned (i) orthogonal to the direction of light emitted by the light sources, (ii) opposite to one another, and (iii) proximal to the flow channel and distal to the flow channel.

B17. The flow cytometry system of any one of embodiments B1-B16, wherein the detector module comprises (i) a selective optical element, (ii) a dispersive optical element, or (iii) a combination of (i) and (ii).

B18. The flow cytometry system of embodiment B17, wherein the light transmission module is configured to deliver light from the collector module to (i) the selective optical element, (ii) the dispersive optical element, or (iii) a combination of (i) and (ii).

B19. The flow cytometry system of any one of embodiments B1-B18, wherein the light transmission module comprises one optical fiber or a plurality of optical fibers.

B20. The flow cytometry system of any one of embodiments B15 to B17, wherein the light transmission module is configured to deliver light from two collectors to (i) the selective optical element, (ii) the dispersive optical element, or (iii) a combination of (i) and (ii).

B21. The flow cytometry system of embodiment B20, wherein the light transmission module comprises a plurality of optical fibers.

B22. The flow cytometry system of embodiment B21, wherein the light transmission module is configured to combine the light from two collectors.

B23. The flow cytometry system of embodiment B21, wherein the light transmission module is configured to combine the light from two collectors, and deliver the combined light from the two collectors to (i) the selective optical element, (ii) the dispersive optical element, or (iii) a combination of (i) and (ii).

B24. The flow cytometry system of any one of embodiments B20 to B23, wherein the light transmission module is configured to 1) deliver light emitted from the measurement subzone closest to the flow channel inlet obtained from both collectors to the selective optical element; and 2) deliver light emitted from the remaining measurement subzones obtained from both collectors to the dispersive optical element.

B25. The flow cytometry system of any one of embodiments B20 to B23, wherein the light transmission module is configured to 1) deliver light emitted from the measurement subzone closest to the flow channel inlet obtained from a first collector module to the selective optical element; and 2) deliver light emitted from some or all measurement subzones obtained from a second collector module to the dispersive optical element.

B26. The flow cytometry system of any one of embodiments B20 to B23, wherein the light transmission module is configured to 1) deliver light emitted from the measurement subzone closest to the flow channel inlet obtained from a first collector module to the selective optical element; 2) deliver light emitted from the remaining measurement subzones obtained from the first collector to the dispersive optical element; and 3) deliver light emitted from some or all measurement subzones obtained from a second collector module to the dispersive optical element.

B27. The flow cytometry system of any one of embodiments B1-B26, wherein the detector module comprises one or more of a lens, photomultiplier tube (PMT), filter, slit, prism and grating.

B28. The flow cytometry system of embodiment B27, wherein the detector module comprises (i) a bandpass filter, (ii) a notch filter, or combination of (i) and (ii).

B29. The flow cytometry system of embodiment B27 or B28, wherein the detector module comprises (i) a collimating lens, (ii) a focusing lens, or combination of (i) and (ii).

B30. The flow cytometry system of any one of embodiments B17-B29, wherein the selective optical element comprises a PMT.

B31. The flow cytometry system of any one of embodiments B17-B30, wherein the dispersive optical element comprises a prism, or a grating, or a prism and a grating.

B32. The flow cytometry system of any one of embodiments B1-B31, comprising a data analysis system.

B33. The flow cytometry system of embodiment B32, where the data analysis system is configured to analyze light detected by the detector.

B34. The flow cytometry system of embodiment B32 or B33, wherein the detector comprises a selective optical element, and a selective subset of component signals obtained by the selective optical element is analyzed.

B35. The flow cytometry system of any one of embodiments B32-B34, wherein the detector comprises a dispersive optical element, and (i) component spectral signals from a composite output signal of a single measurement subzone are analyzed, (ii) component spectral signals from a composite output signal of a plurality of measurement subzones are simultaneously analyzed, or (iii) a combination of (i) and (ii).

C1. An illumination system comprising a measurement zone for analyzing an analyte, a plurality of light sources and a light source synchronizer, wherein:
    (a) the measurement zone comprises two or more discrete measurement subzones;
    (b) each of the light sources emits light of a different wavelength;
    (c) each of the light sources is configured for transmission to a unique measurement subzone; and
    (d) the light source synchronizer is configured to activate and/or deactivate each light source in a predetermined sequence and at predetermined time intervals relative to each other.

C2. The illumination system of embodiment C1, wherein the light source synchronizer comprises a controller and a plurality of switches, wherein:
    the plurality of switches activate and deactivate each of the light sources; and
    the controller independently directs each of the plurality of switches to activate or deactivate a light source.

C3. The illumination system of embodiment C2, wherein each of the switches is in separate communication with each of the light sources.

C4. The illumination system of embodiment C2 or C3, wherein the controller in the light source synchronizer is configured to sequentially activate and deactivate each of the light sources.

C5. The illumination system of embodiment C4, wherein the controller in the light source synchronizer is configured to (i) activate a first light switch, whereby a first measurement subzone is illuminated for analysis of the analyte, (ii) deactivate the first light switch following the time interval needed for the analyte to transit the first measurement subzone, (iii) activate the second light switch at a time when the analyte enters a second measurement subzone, whereby a second measurement subzone is illuminated for analysis of the analyte, (iv) deactivate the second light switch following the time interval needed for the analyte to transit the second measurement subzone, and (v) repeat parts (iii) and (iv) until the analyte has transited all or a desired portion of the total number of measurement subzones in the illumination system.

C6. The illumination system of embodiment C4 or C5, wherein the controller in the light source synchronizer is configured to sequentially activate one of the light sources after deactivating one of the other light sources.

C7. The illumination system of any one of embodiments C1 to C6, wherein the measurement zone is in a flow channel.

C8. The illumination system of embodiment C7, wherein the measurement subzones are positioned linearly in the direction of fluid flow in the flow channel.

C9. The illumination system of embodiment C7 or C8, wherein the controller in the light source synchronizer is configured to (i) activate a light source that illuminates a measurement subzone, while all other light sources are deactivated; (ii) deactivate the light source that illuminates the measurement subzone illuminated in (i) and activate a light source that illuminates a measurement subzone located adjacent to the measurement subzone illuminated in (i) and closer to the flow channel outlet, while all other light sources are deactivated, and (iii) repeat (i) and (ii) until a light source that illuminates a measurement subzone closest to the flow channel outlet is activated and then deactivated.

C10. The illumination system of any one of embodiments C7 to C9, which is in connection with a gate configured to: (i) detect the presence of a particle in a measurement subzone closest to the flow channel inlet, and (ii) transmit a signal to the controller in the light source synchronizer to sequentially activate and deactivate light sources.

C10.1 The illumination system of any one of embodiments C7 to C10, wherein the flow channel is in a flow cytometer.

C11. The illumination system of any one of embodiments C1-C10.1, which is configured to sequentially generate a plurality of illumination volumes when each of the measurement subzones are sequentially illuminated.

C12. The illumination system of any one of embodiments C1-C11, comprising 2, 3, 4, 5, 6, 7, 8, 9, 10, 11, 12, 13, 14, 15, 16, 17, 18, 19 or 20 light sources.

C12.1 The illumination system of embodiment C12, comprising 3 light sources.

C13. The illumination system of any one of embodiments C1-C12.1, comprising a light delivery module connected to the light sources and the measurement zone.

C14. The illumination system of embodiment C13, wherein the light delivery module comprises an optical fiber or plurality of optical fibers.

C15. The illumination system of embodiment C13 or C14, wherein the light delivery module comprises a shaping optic, or a focusing optic, or a shaping optic and focusing optic.

D1. A kit, comprising:
    a panel of optical standard particles, each capable of being conjugated to a distinct type/amount of optically detectable label or associated with a distinct molecular marker capable of being conjugated to a distinct type/amount of optically detectable label wherein:
    the signals from the optically detectable labels of each member of the panel are calibrated according to size, type and/or amount of the particles, based on the measured optical intensities of each member of the panel of optical standard particles; and
    each member of the panel of optical standard particles has an excitation spectrum that is different than the excitation spectra of the other members of the panel, and/or each member of the panel of optical standard particles has an emission spectrum that is different than the emission spectra of the other members of the panel.

D1.1. A kit, comprising:
    a panel of optical standard particles, each capable of being conjugated to a distinct type/amount of optically detectable label or associated with a distinct molecular marker capable of being conjugated to a distinct type/amount of optically detectable label wherein:
    the signals from the optically detectable labels of each member of the panel are calibrated according to size, type and/or amount of the particles, based on the measured optical intensities of each member of the panel of optical standard particles; and
    each member of the panel of optical standard particles has excitation and/or emission spectra that is different than the excitation and/or emission spectra of the other members of the panel.

D2. The kit of embodiment D1 or D1.1, wherein the optically detectable label is selected from among a fluorophore, a chromophore, a chemiluminescent label and a bioluminescent label.

D3. The kit of any one of embodiments D1, D1.1 or D2, wherein one or more of the optical standard particles is associated with a ligand.

D4. The kit of embodiment D3, wherein the ligand is an antibody.

D5. The kit of any one of embodiments D1 to D4, wherein one or more of the optical standard particles is/are conjugated to an optically detectable label and/or are associated with one or more ligands that is/are conjugated to an optically detectable label.

D6. The kit of any one of embodiments D1 to D5, wherein the optically detectable label is a fluorophore.

D7. The kit of embodiment D6, wherein the fluorophore is selected from among DyLight488, a Brilliant Violet dye, Pacific Blue, Chrome Orange, Krome Orange, Brilliant Blue 515, PE, FITC, PE-Cy5.5, PE-Cy7, APC, Alexa647, APC-Alexa700 and APC-Alexa750.

D7.1. The kit of embodiment D6 or D7, wherein each member of the panel of optical standard particles is associated with a fluorophore.

D7.2. The kit of any one of embodiments D6 to D7.1, wherein the brightness (signal intensity) of each fluorophore is calibrated.

D7.3. The kit of any one of embodiments D1 to D6, wherein the optical standard particles comprise fluorophore capture moieties that can be stained with fluorophores to provide quantitative reference spectra for spectral unmixing.

D7.4. The kit of embodiment D7.3, further comprising instructions for use comprising an assay protocol providing instructions for sample staining, preparation of the optical standard particles, and setting of delay times for data acquisition.

D8. The kit of any one of embodiments D1 to D7.4, further comprising instructions for use in the flow cytometry system of any one of embodiments B1 to B35 and/or for use in the illumination system of any one of embodiments C1 to C15.

D9. The kit of any one of embodiments D1 to D8, further comprising instructions for use comprising an assay protocol providing procedures for sample preparation, fluorescent staining, and data acquisition.

D10. The kit of any one of embodiments D1 to D8, further comprising instructions for use comprising an assay protocol providing procedures for sample preparation, fluorescent staining, and data acquisition.

D11. The kit of any one of embodiments D1 to D10, further comprising instructions for use comprising a data analysis protocol for producing intensity estimates for each optically detectable label present in or on an optical standard particle or a particle to be analyzed in a sample.

D12. The kit of embodiment D11, wherein the data analysis protocol further comprises:

one or more procedures for obtaining intensity-calibrated reference spectra; and one or more procedures for spectral unmixing using the intensity-calibrated reference spectra to produce quantitative estimates of the brightness (intensity of the signal) from each optically detectable label.

D13. The kit of embodiment D12, wherein the quantitative estimates are absolute.

E1. A combination, comprising:

the kit of any one of embodiments D1 to D13; and the flow cytometry system of any one of embodiments B1 to B35, or the illumination system of any one of embodiments C1 to C15.

EXAMPLES

The examples set forth below illustrate certain implementations and do not limit the technology.

Example 1: Resolution of Multi-Intensity Beads

An excitation-emission matrix flow cytometer (EEM FC) was constructed around a flow cell with a gel-coupled collection optic on one face of the flow cell to collect fluorescence signals, a 40× microscope objective on the opposite side to collect orthogonal light scatter, and a forward angle light scatter assembly containing a focusing lens, obscuration bar, adjustable iris, and an amplified photodiode. A fluidics module was used to establish a hydrodynamically focused sample stream in the center of the flow cell. Three laser beams were focused into the middle of the flow cell (onto corresponding measurement subzones), using beam steering and shaping optics to create three spatially separated illumination volumes in the center of the flow cell. A linear array of optical fibers was positioned relative to the collection optic so that the light emitted from each of the illumination volumes was imaged onto the face of the fibers. The other end of the fiber arrays was positioned at the focal plane of the spectral detection module such that the light from each fiber was spectrally imaged onto the detector, where it was processed and read out to the EEM FC data analysis system.

Figures 9A, 9B, 9C, 9D, 9E, 9F:
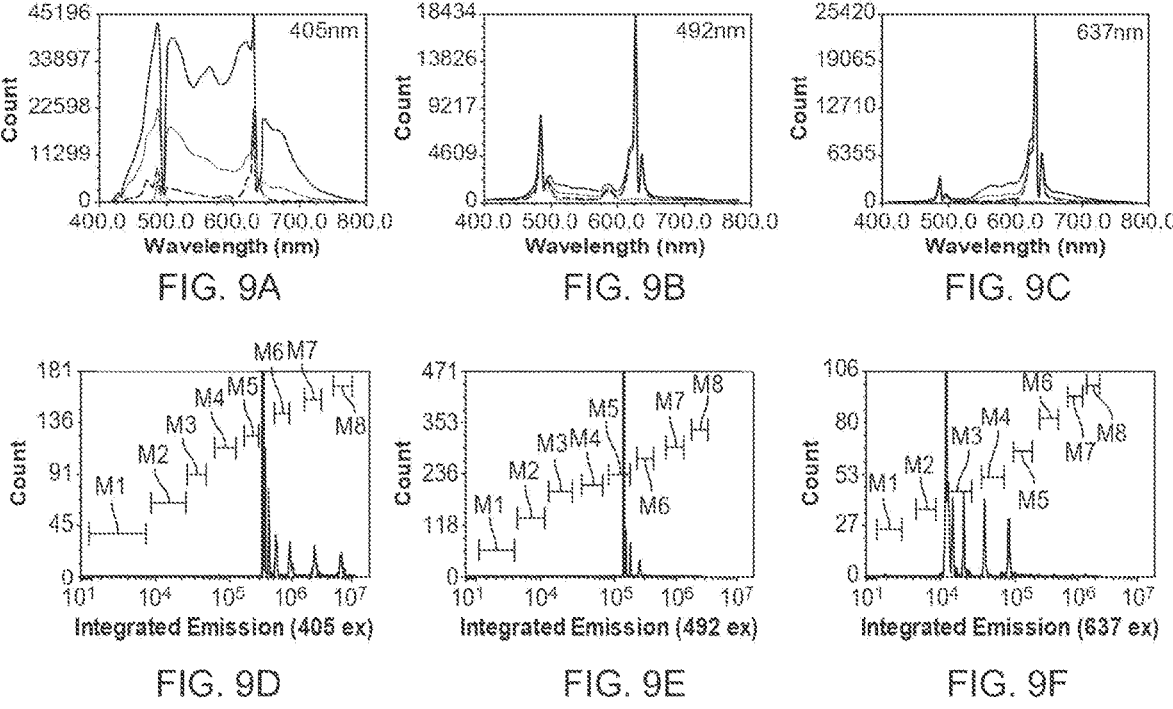
FIG. 9A shows the average spectra of all beads measured from the violet illumination volume.
FIG. 9B shows the average spectra of all beads measured from the blue illumination volume.
FIG. 9C shows the average spectra of all beads measured from the red illumination volume.
FIG. 9D shows a frequency histogram of the integrated intensity measured from the violet illumination volume.
FIG. 9E shows a frequency histogram of the integrated intensity measured from the blue illumination volume.
FIG. 9F shows a frequency histogram of the integrated intensity measured from the red illumination volume.

To assess the performance of the multilaser hyperspectral flow cytometer system described above, multi-intensity Rainbow beads (Spherotech, Inc) made up of eight (8) bead populations with different intensities were measured. Bead detection was triggered by light scatter as beads passed through the blue laser spot. As each bead flowed through each of the blue, red, and violet lasers, fluorescence emitted by each illumination volume was collected by the collection optic, focused into the fiber array, and delivered to the spectral detection module where the light from each illumination volume was dispersed and detected on a discrete region of the detector. FIGS. 9A-9F show resolution of multi-intensity beads without illumination control. Shown in FIG. 9 are average spectra of all beads measured from the violet (upper left panel, A), blue (upper middle panel, B), and red (upper right panel, C) illumination volumes, and frequency histograms of integrated intensities measured from the three illumination volumes (three lower panels, D, E, and F, corresponding to upper panels A, B and C, respectively). The system showed very high background signals, as indicated by the integrated intensity signal associated with the dimmest bead (405 nm: >340,000 counts; 492 nm: >140,000 counts; and 637 nm: >10,000 counts). Only 5 of the 8 bead populations were resolved in the violet probe volume, 2 of the 8 bead populations were resolved in the blue probe volume, and 3 of the 8 bead populations were resolved in the red probe volume. Light from the three lasers appeared to cause an increased background signal from the detector, resulting in loss of resolution of particles with lower intensities.

Example 2: Improved Resolution of Multi-Intensity Beads

Figures 10A, 10B, 10C, 10D, 10E, 10F:
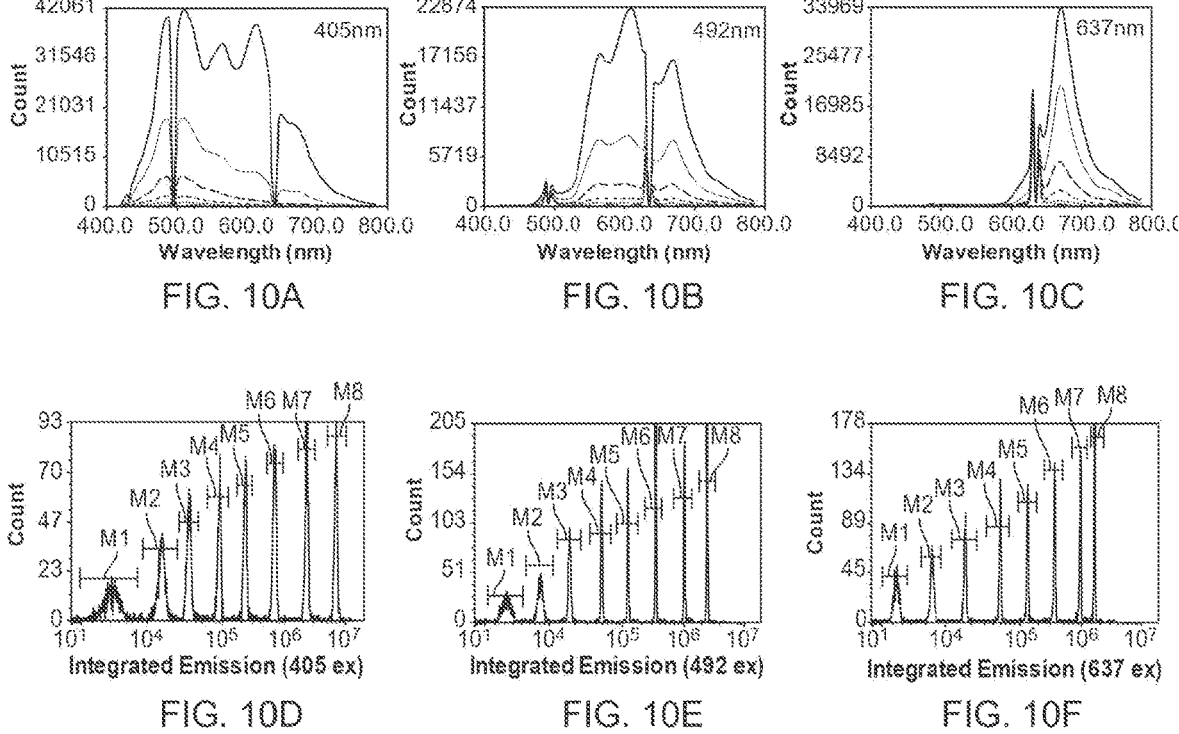
FIG. 10A shows the average spectra of all beads measured from the violet illumination volume.
FIG. 10B shows the average spectra of all beads measured from the blue illumination volume.
FIG. 10C shows the average spectra of all beads measured from the red illumination volume.
FIG. 10D shows a frequency histogram of the integrated intensity measured from the violet illumination volume.
FIG. 10E shows a frequency histogram of the integrated intensity measured from the blue illumination volume.
FIG. 10F shows a frequency histogram of the integrated intensity measured from the red illumination volume.
Figure 11A:
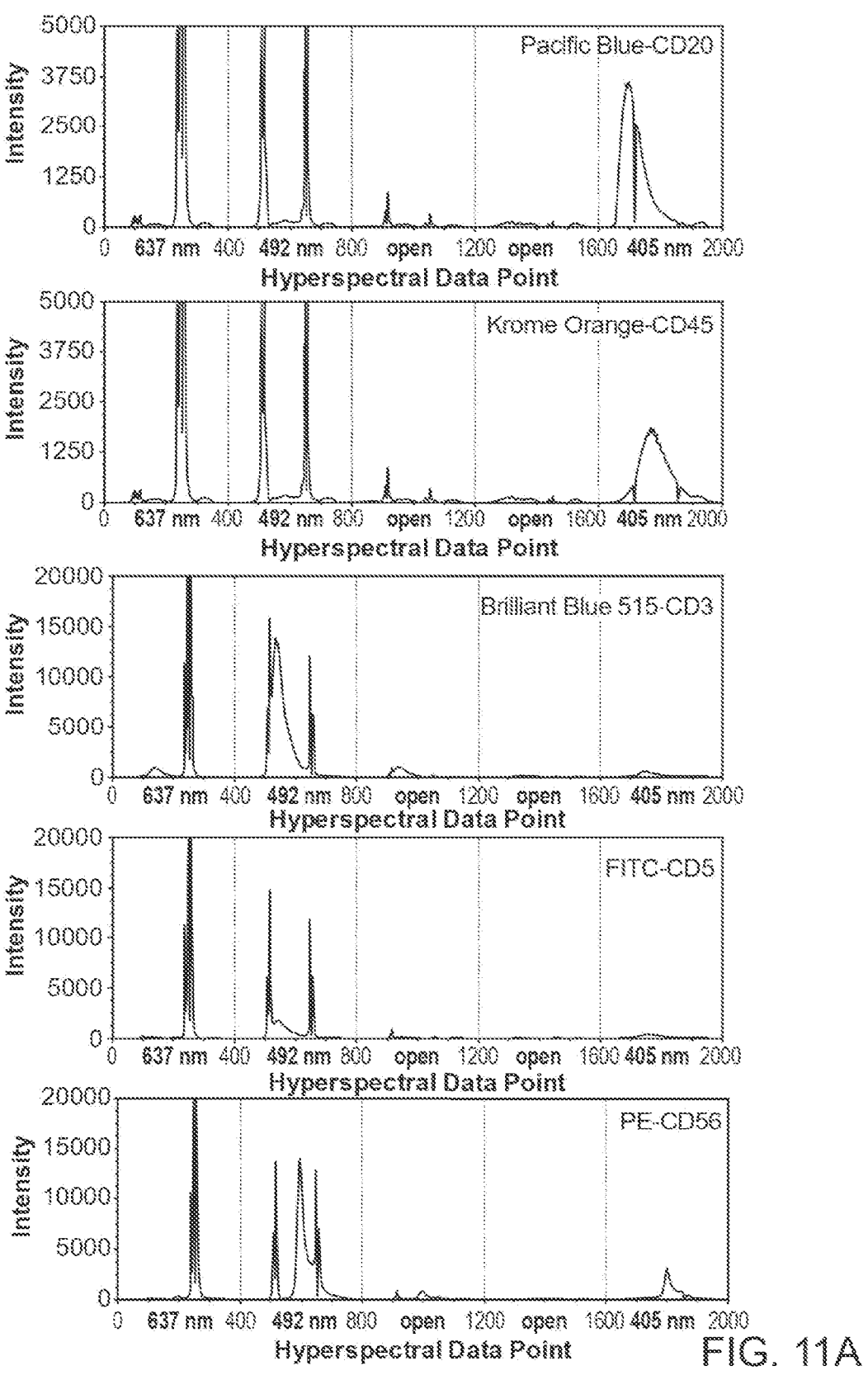
FIG. 11A shows the spectral measurements of antibody capture beads stained with, from top to bottom, the following fluorophores: Pacific Blue (anti-CD20 capture antibody), Krome Orange (anti-CD45 capture antibody), Brilliant Blue 515 (anti-CD3 capture antibody), FITC (anti-CD5 capture antibody) and PE (anti-CD56 capture antibody).
Figure 11B:
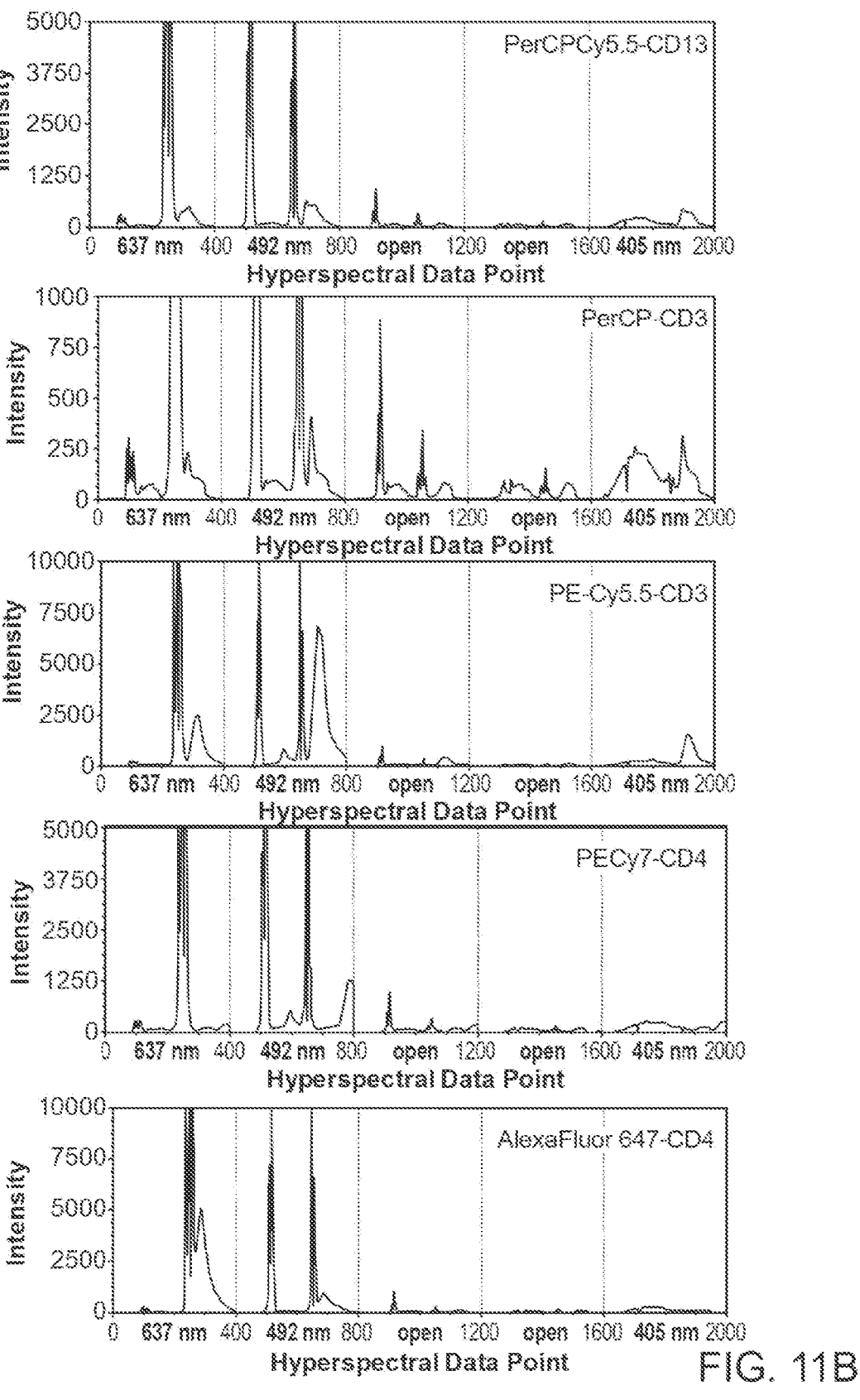
FIG. 11B shows the spectral measurements of antibody capture beads stained with, from top to bottom, the following fluorophores: PerCPCy5.5 (anti-CD13 capture antibody), PerCP (anti-CD3 capture antibody), PE-Cy5.5 (anti-CD3 capture antibody), PECy7 (anti-CD4 capture antibody) and AlexaFluor 647 (anti-CD56 capture antibody).
Figure 11C:
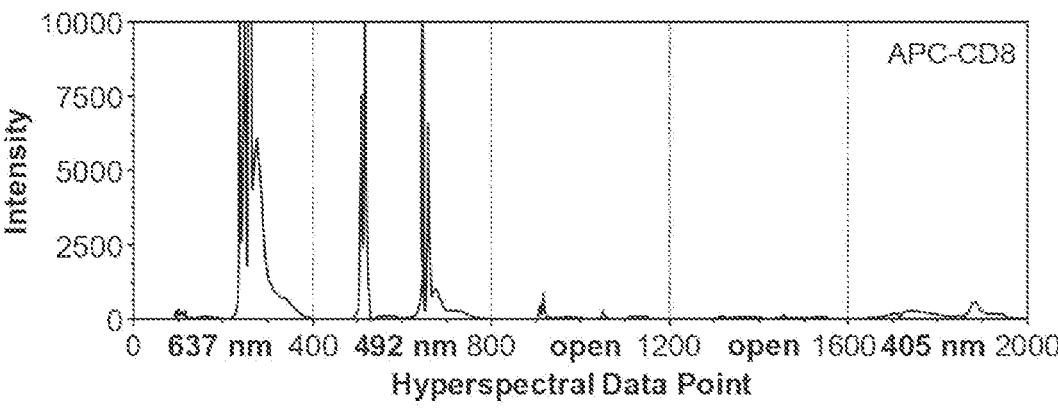
FIG. 11C shows the spectral measurements of antibody capture beads stained with, from top to bottom, the following fluorophores: APC (anti-CD8 capture antibody), APC-Alexa700 (anti-CD19 capture antibody) and APC-Alexa750 (anti-CD16 capture antibody).
Figure 11C:
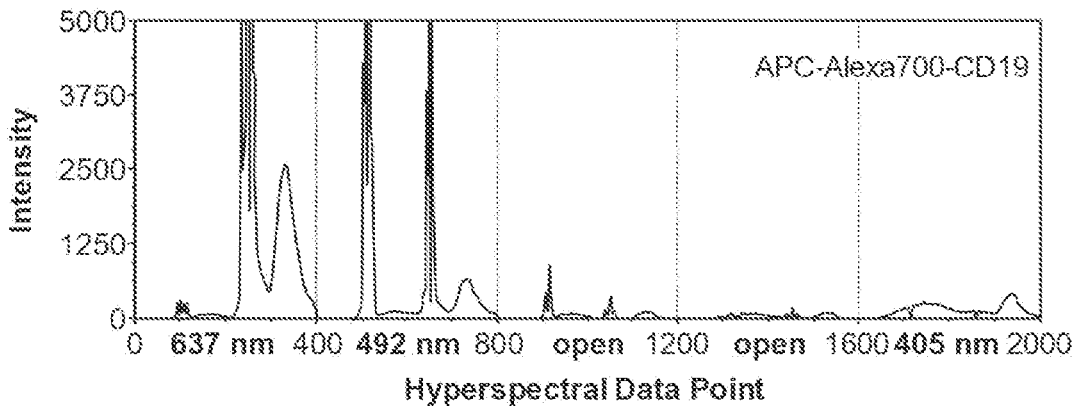
Figure 11C:
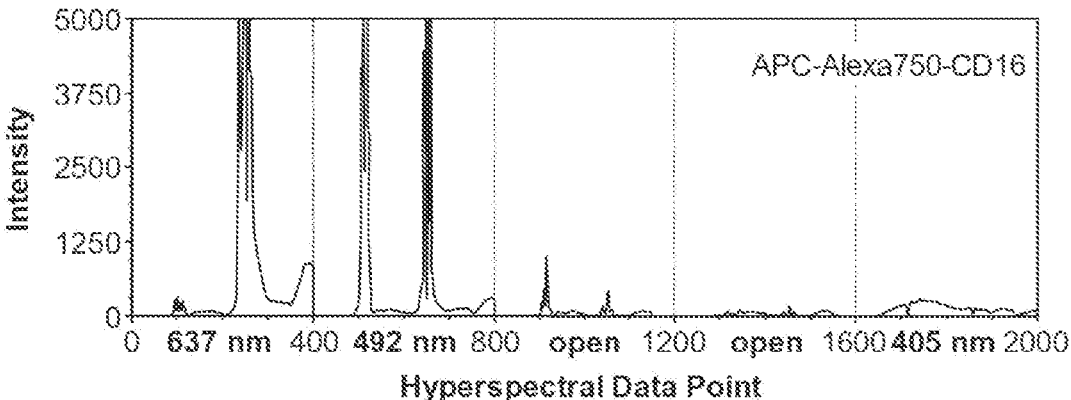
Figure 11D:
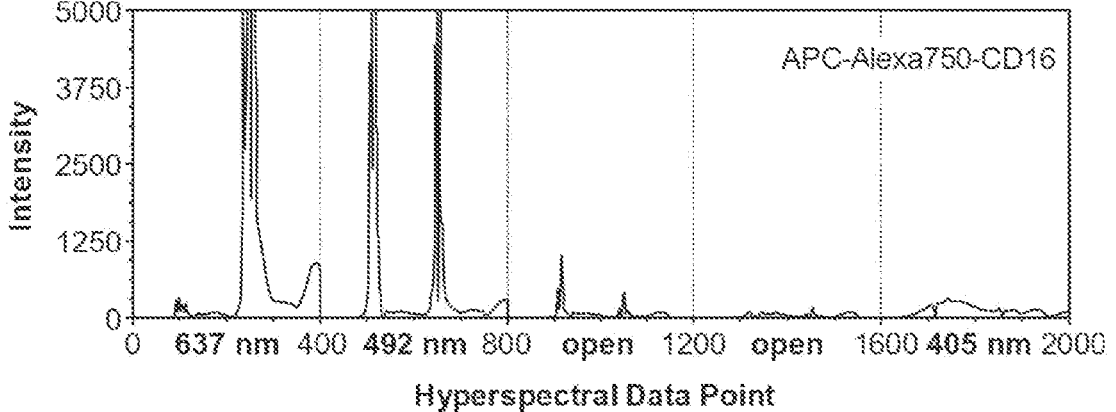
FIG. 11D shows the spectral measurements of antibody capture beads stained with APC-Alexa750 (anti-CD16 capture antibody).

To address the problem of high background described in Example 1, a custom designed light source synchronizer was developed for the flow cytometer data analysis system. The light source synchronizer controlled the emission from each laser to illuminate its corresponding measurement subzone (and generate an illumination volume) only when a particle was passing through, and not to illuminate its measurement subzone when there was no particle present in that subzone. FIGS. 10A-10F show resolution of multi-intensity beads with illumination control (i.e., light source synchronization). Shown in FIG. 10 are average spectra of all beads measured from the violet (upper left panel, A), blue (upper middle panel, B), and red (upper right panel, C) illumination volumes, and frequency histograms of integrated intensities measured from the three illumination volumes (three lower panels, D, E, and F, corresponding to upper panels A, B and C, respectively). When the system was operated with the light source synchronizer operating, the background integrated emission signal was greatly reduced (405 nm: <4000 counts; 492 nm: <3200 counts and 637 nm: <2400 counts) and permitting all eight peaks to be resolved in each of the probe volumes (e.g., compare panels D, E and F of FIG. 10 with corresponding panels D, E and F, respectively, in FIG. 9). Thus, using a light source synchronizer to control the illumination at each of the measurement sub-zones results in significantly improved measurement performance and resolution of dim particles.

Example 3: Improved Resolution of Multi-Intensity Beads

To evaluate the capabilities of an excitation-emission matrix flow cytometer (EEM FC) to measure fluorescence-labeled antibodies used in a typical cell analysis application, antibody capture beads were stained with each of thirteen different fluorescence-labeled antibodies. FIGS. 11A-11D show spectral measurements of multicolor fluorescent antibody-stained particles. The emission spectra of the stained capture beads were measured at 3 different excitation wavelengths (405 nm, 492 nm and 637 nm) to generate the EEM spectra of each single fluorochrome-stained capture bead (FIG. 11). These were analyzed by EEM FC to measure the excitation-emission matrix (EEM) spectra of each fluorescence-labeled antibody. The EEM spectra contain the emission spectra produced by excitation of the fluorochromes as they pass through each measurement sub-zone and are illuminated by each different illumination wavelength. FIG. 11 shows that each of the nine different fluorochromes has a different emission spectrum intensity produced by each different excitation wavelength. This is important because the ability to measure both a fluorophore's emission spectrum and its excitation spectrum via its passage through different measurement sub-zones illuminated by different illumination wavelengths, resulting in distinct EEM spectra for each fluorochrome, provides significantly more information to assist in identifying the fluorophores present and estimating their abundance.

The EEM flow cytometer can be operated in a "conventional" mode, where each fluorescent label is associated with a single excitation wavelength and emission spectral range, termed a virtual band pass (VBP), as is done conventionally by flow cytometry, or can be operated by EEM FC to measure the excitation-emission matrix (EEM) spectra of each particle. The advantages of spectral flow cytometry using VBP filters, over conventional flow cytometry, include: (a) eliminating the need to change physical filters to optimize light detection from individual fluorochromes, and (b) having the ability to change the VBPs after data acquisition, thereby improving resolution of individual fluorophores. However, analyses of spectral flow cytometry data using VBPs is still essentially a conventional approach in that the full amount of information present in the spectra from each particle is not exploited. The information in the particle emission spectra can be more fully exploited using various spectral analysis approaches, including spectral unmixing and other algorithms including classical least squares (CLS) unmixing, non-negative least squares (NNLS) unmixing, alternating least squares (ALS) unmixing, principal components analysis (PCA), negative matrix factorization (NMF), linear discriminant analysis (LDA), multivariate curve resolution (MCR), and classification algorithms. Several such analysis approaches can be used for spectral flow cytometers. These examples restrict their spectral analysis to emission spectra generated by one or two lasers. The system described herein, by extending the spectral analysis to emission spectra generated by each of three or more discrete and individual excitation wavelengths, provides the first excitation emission matrix-based flow cytometry system, obtaining and exploiting information about both the excitation and emission properties of the particles, which provides increased ability to resolve optical probes with different spectral properties from one another.

Example 4: Analysis of Bacterial Cell Expressing Different Fluorescent Proteins The analysis of genetically encoded fluorescent proteins in individual cells is another useful application of flow cytometry. It can be challenging to measure multiple fluorescent proteins in combination with other fluorescence probes because the spectral emission spectra often overlap significantly, precluding their effective use in conventional flow cytometry systems. Spectral flow cytometry using spectral unmixing approaches can offer improved performance in resolving fluorescent proteins, but for fluorescent proteins that have a high degree of spectral emission overlap with other fluorescence, resolution can still be limited. Exploitation of the fluorescence excitation as well as the spectral emission via excitation emission matrix flow cytometry offers the potential for improved resolution of fluorophores with a high degree of spectral emission overlap.

To test the ability to simultaneously measure the excitation and emission properties of various fluorescent proteins, a set of eight bacterial cultures was obtained, each expressing a different fluorescent protein, using methods as described in Shaner et al., Nature Methods, DOI:10.1038/NMETH.2413 (2013). Briefly, fluorescent protein-coding sequences for the following fluorescent proteins: Blueberry, Venus, Banana, Blue, Turquoise, Orange, Apple and Emerald, were inserted into the constitutive expression vector pNCS. Fluorescent proteins were expressed in *E. coli* strain NEBTurbo (New England BioLabs) or Mach1 (Invitrogen) by growing cultures in 2×YT (yeast extract and tryptone) medium supplemented with ampicillin overnight at 37° C., with shaking at 250 r.p.m.

Figure 12A:
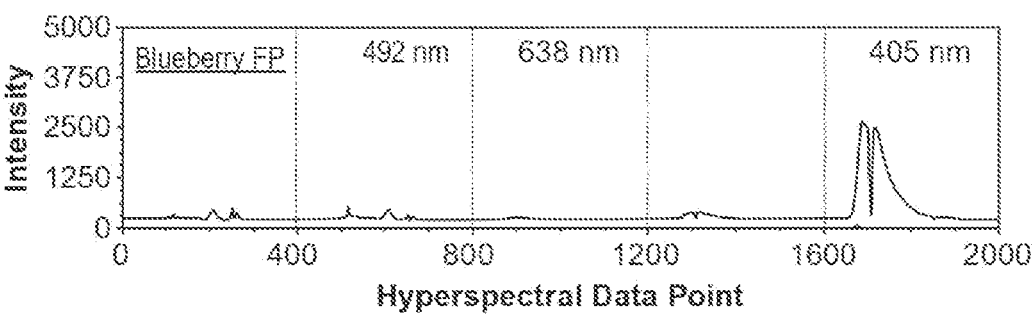
FIG. 12A shows spectral measurements of cells expressing the following fluorescent proteins (FP) from top to bottom: Blueberry, Venus, Banana and Blue.
Figure 12A:
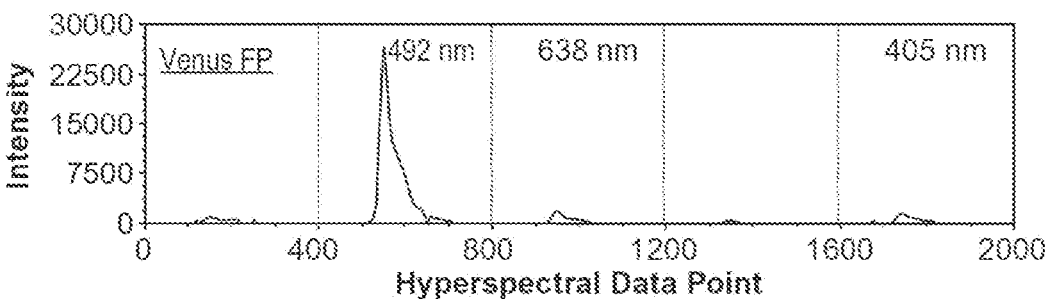
Figure 12A:
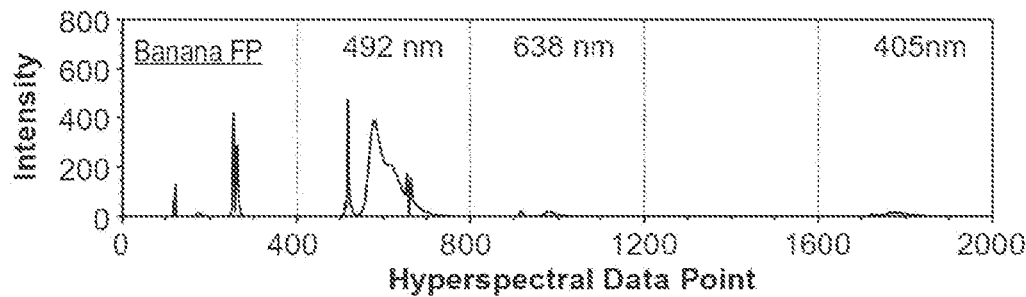
Figure 12A:
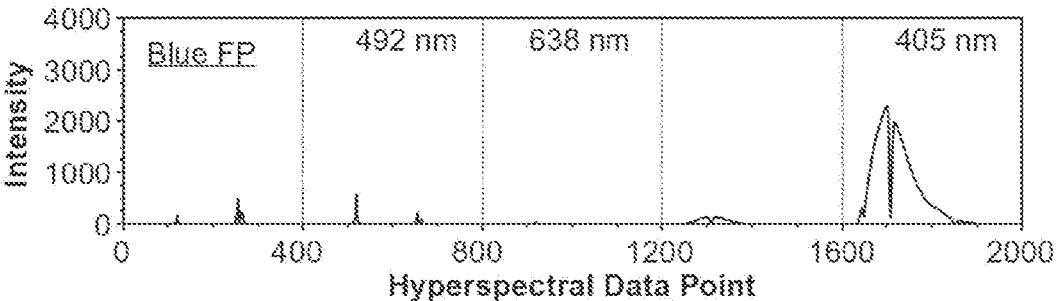
Figure 12B:
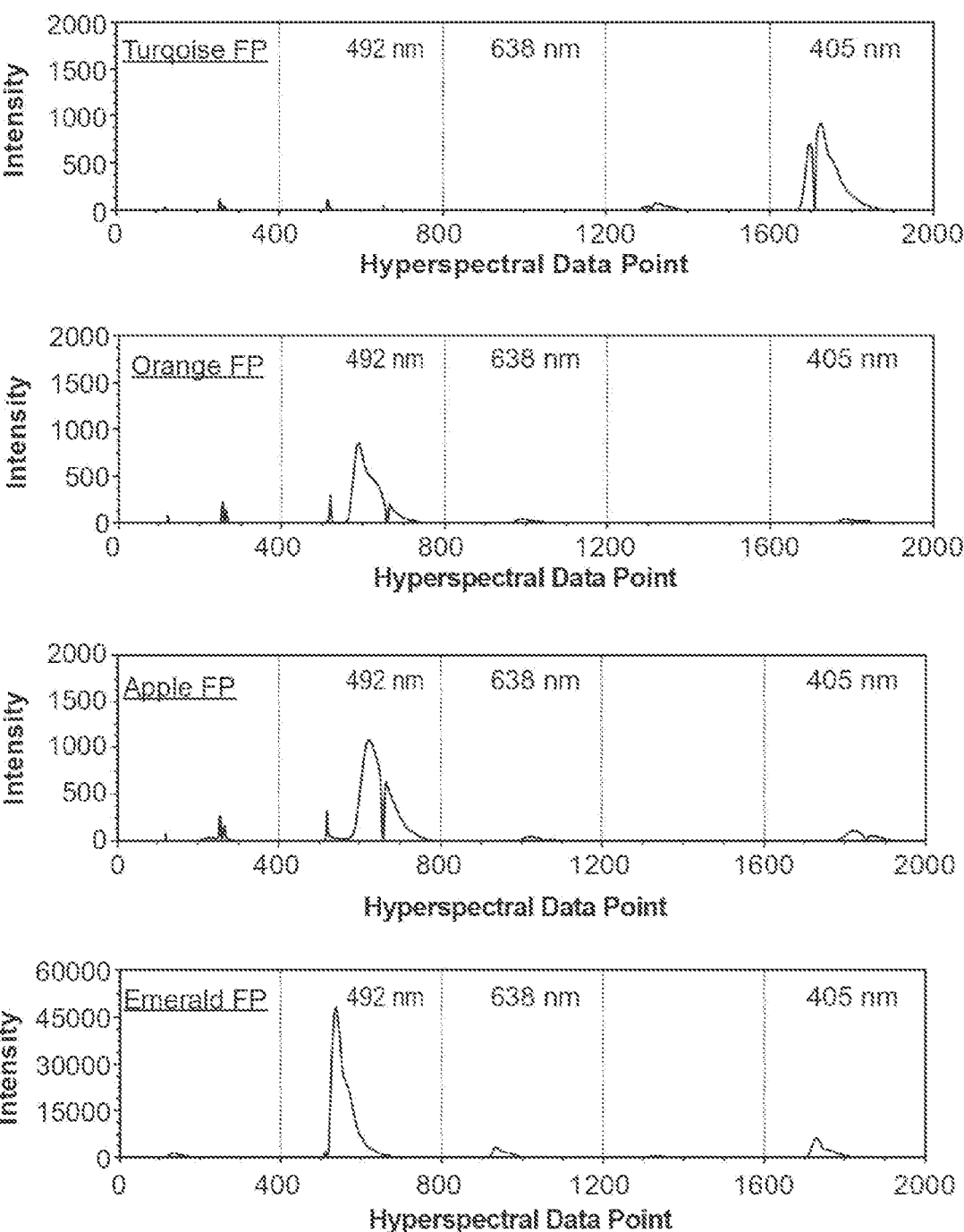
FIG. 12B shows spectral measurements of cells expressing the following fluorescent proteins (FP) from top to bottom: Turquoise, Orange, Apple and Emerald.

FIGS. 12A and 12B show spectral measurements of fluorescent protein-expressing cells. Cultures were diluted in phosphate buffered saline (PBS) to a suitable single cell concentration ($\sim5\times10^6$/mL) and samples were measured at 3 different excitation wavelengths (405 nm, 492 nm and 638 nm) to generate EEM spectra of each single fluorescent protein expressing cell culture (FIG. 12).

As was seen for the fluorescent-labeled antibodies in Example 3, each fluorescent protein produces a characteristic EEM spectrum made up of emission spectra produced by each different illumination wavelength as the particles pass through each measurement sub-zone. Thus, measuring both the excitation and emission spectra of each particle provides more information to improve the identification of different fluorophores associated with a particle, as well as determination of the abundance of each of those fluorophores.

Example 5: Representative Particle Analysis Method

Below is an outline of a representative method for analyzing particles using a flow cytometry device and/or system provided herein. Provided are various options for conducting certain steps.

1. Prepare sample
2. Stain sample
3. Measure individual particles
   a. Flow through a flow cell/channel
      i. Hydrodynamically focused
   b. Illuminate with lasers
      i. Multiple lasers ii. Multiple lasers focused and steered to discrete foci iii. Multiple lasers whose intensity is modulated to coincide with particle passage through discrete foci c. Collect emitted light i. Using high NA collection optics ii. Using high NA collection optics on two sides of the flow cell iii. Using an array of optical fibers to collect light emitted from discrete laser foci iv. Using an array of optical fiber to collect light emitted from discrete laser foci from two sides of the flow cell and combine for dispersion and/or detection d. Disperse collected light i. Using an optical fiber to introduce into a spectrograph/dispersion element ii. Using optical fibers to introduce light emitted from multiple discrete foci into multiple spectrographs iii. Using optical fibers to introduce light from multiple discrete foci into a single spectrograph e. Detect dispersed light i. Using an array detector ii. Using multiple array detectors iii. Using a single array detector to detect dispersed light emitted from multiple discrete laser foci f. Analyze detected light i. Using spectral analysis algorithms ii. Using spectral analysis algorithms on hyperspectral data sets iii. Using hyperspectral data analysis algorithms in real-time iv. Using hyperspectral data analysis algorithms in real-time to enable single particle sorting based on estimated particle properties g. Estimate particle properties i. Particle abundance of probes used ii. Particle autofluorescence Below is a Table providing an overview of certain steps of particle analysis using flow cytometry.

TABLE

| Particle analysis using flow cytometry (overview of certain steps) | |
| --- | --- |
| Step | Purpose |
| Sample delivery | Present particles to the measurement volumes |
| Sample illumination | Excite fluorescent dyes, induce light scatter |
| Light collection | Collect emitted fluorescence light scatter |
| Spatial filtering | Reject out of focus light not originating from the measurement probe volume |
| Spectral filtering | Select emission wavelength range(s) for measurement |
| Detection | Determine the amount of light emitted from each particle in an emission wavelength range |

Example 6: Representative Flow Cytometry Device

A representative flow cytometry device contains:

1. a flow channel in which to present and interrogate a sample;

2. a fluidics module that presents the sample to a measurement zone (e.g., flow channel containing a series of measurement sub-zones);

3. a series of focused light sources that create illumination volumes within the measurement zone (e.g., in each of the measurement sub-zones);

4. a light source synchronizer to control the illumination at each of the measurement subzones;

5. optics to collect the light produced from each illumination volume within the measurement zone;

6. an optical fiber array to deliver collected light produced from each illumination volume to a point detection module and a spectral dispersion module;

7. a spectral dispersion module that spectrally separates the light collected from each focused light source;

8. a spectral detection module that measures the spectrally-resolved light produced by each focused light source; and 9. a data analysis system that produces spectral data sets of each particle and analyzes the data sets to determine the properties of individual particles.

A representative spectral flow cytometer (e.g., an EEM FC system) includes: (a) a flow channel through which sample flows, (b) one or more illumination volumes formed within a measurement zone by the focused output of one of more light sources, (c) collection optics that collect light produced within each illumination volume in the measurement zone and deliver it to a fiber optic array that carries the collected light from each illumination volume to a point detection module and/or (d) a spectral dispersion module that disperses the light from each illumination volume into a spectral detection module that measures the spectrally resolved light from each illumination volume. A data analysis system processes and analyzes the data to produce information about sample that passes through the measurement zone and writes it to a data file that is stored on a computer.

A representative EEM FC system described below includes the following components: flow channel, fluidics module, focused light sources, light source synchronizer (illumination control module), collection optics, light delivery, spectral detection module, detector, and data analysis system, each of which is described in detail below.

Flow Channel

A representative flow channel is a rectangular quartz (Hypersil) flow cell with interior dimensions of 180 μm×430 μm, exterior dimensions of 2 mm×4 mm, and a length of 7 mm or 20 mm. The flow cell is mounted within a custom designed holder that provides fluidic input for sample fluids and a fluidic output for waste. Specifically, the flow cell is mounted in a custom holder with stainless steel sheath inlets and outlet tubes with a 0.33" (inch) inner diameter, and a graduated stainless steel sample inlet tube with a 0.006" (inch) inner diameter. The flow cell and holder are mounted in a 60 mm×60 mm cage cube component (ThorLabs). The sheath and sample inlet tubes are connected to the fluidics module.

Fluidics Module

Sample aspirated from a sample tube into a sample loop is delivered via the sample inlet tube to the flow cell, where the sample stream is hydrodynamically focused in the flow cell. Samples pass through a measurement zone where one or more focused light sources create illumination volumes within the sample stream, and collection optics collect and focus light emitted from each illumination volume into an optical fiber contained in a linear fiber array.

A representative fluidics module includes a set of computer-controlled pumps and valves (Global FIA) connected via PEEK tubing. Two pumps are used to deliver the sheath and sample to the flow cell via sheath lines, sample lines, and sample loops comprised of PEEK tubing. A multiport valve and a switching valve (Valco) connect sheath lines, sample lines, and sample loops, and control scripts control the pumps and valves to execute routines including sample load, sample run, and sample flush.

Focused Light Sources

Illumination volumes within the measurement zone are formed by a focused light from one or more light sources. A representative focused light source includes a series of lasers in an integrated laser module (VersaLase, Vortran Laser Technologies) whose beams are focused to a series of spots (measurement subzones) along the flow cell. In certain configurations, light sources are positioned at 100 µm intervals along the center of the flow channel's long axis. In one configuration, light sources include three lasers whose beams are passed through focusing and shaping optics to produce three illumination volumes, each with an elliptical focus profiles of dimensions ranging from 8 µm×30 µm to 15 µm×80 µm, with the profile centers spaced 100 µm apart along the long axis of the flow channel. The output of the lasers is controlled in time by a light source synchronizer (also referred to as an illumination control module), which turns each laser on only when a particle of interest is flowing through its corresponding measurement subzone. In some configurations, focused light sources are part of an illumination module, which is described in further detail in Example 7.

Light Source Synchronizer

A representative light source synchronizer (also referred to herein as an illumination control module) includes a printed circuit board bearing a logic gate and inverter, a programmable integrated circuit delay line, a series of resistors, and a potentiometer. The synchronizer receives input from the data analysis system at the start of a measurement sequence and sends output to the integrated laser module to control the output of the individual lasers.

The default state for the system is the first, triggering laser is ON and all of the other lasers are OFF. When the data analysis system detects a pulse from the trigger channel, its sends a signal to the light source synchronizer to initiate a sequence in which:

a) after a first delay time as described herein, set to the period of time estimated for the particle to transit its measurement subzone, a signal is sent to the integrated laser module to turn OFF the first laser for a time estimated for the particle to transit the final measurement subzone in the measurement zone;

b) after a second delay time as described herein, set to when the particle is estimated to enter a second measurement subzone, a signal is sent to the integrated laser module to turn ON the second laser for a period of time estimated for the particle to transit the second measurement subzone and then to turn the second laser OFF;

c) after a third delay time as described herein, set to when the particle is estimated to enter a third measurement subzone, a signal is sent to the integrated laser module to turn ON the third laser for a period of time estimated for the particle to transit the third measurement subzone and then to turn the third laser OFF;

d) for systems that include additional measurement subzones, additional lasers can be activated by repeating step c; and e) at the end of the sequence, when the particle exits the final measurement subzone, the first triggering laser is turned back ON and the system is returned to the default state, ready for the detection of another particle.

In some configurations, a light source synchronizer is part of an illumination module, which is described in further detail in Example 7.

Collection Optics

Light emitted from illumination volumes in the measurement zone is collected by a custom optic coupled to the flow cell via an index-matching gel. The optic is designed to image, with high resolution over a wavelength range from less than 200 nm to 1400 nm or greater, light from a series of illumination volumes in the measurement zone onto a custom-fabricated array of optical fibers. The magnification (3.2×), focal length (40 mm), and numerical aperture (1.0) of the optic match the desired height (5-20 µm) and spacing (100 µm, center to center) of the illumination volumes in the measurement zone to the numerical aperture (0.28), diameter (270 um), and spacing (320 µm, center to center) of the optical fibers in the fiber array. In some configurations, collection optics are placed on both wide faces of the flow cell to collect light from both sides of the measurement zone.

Figure 2A:
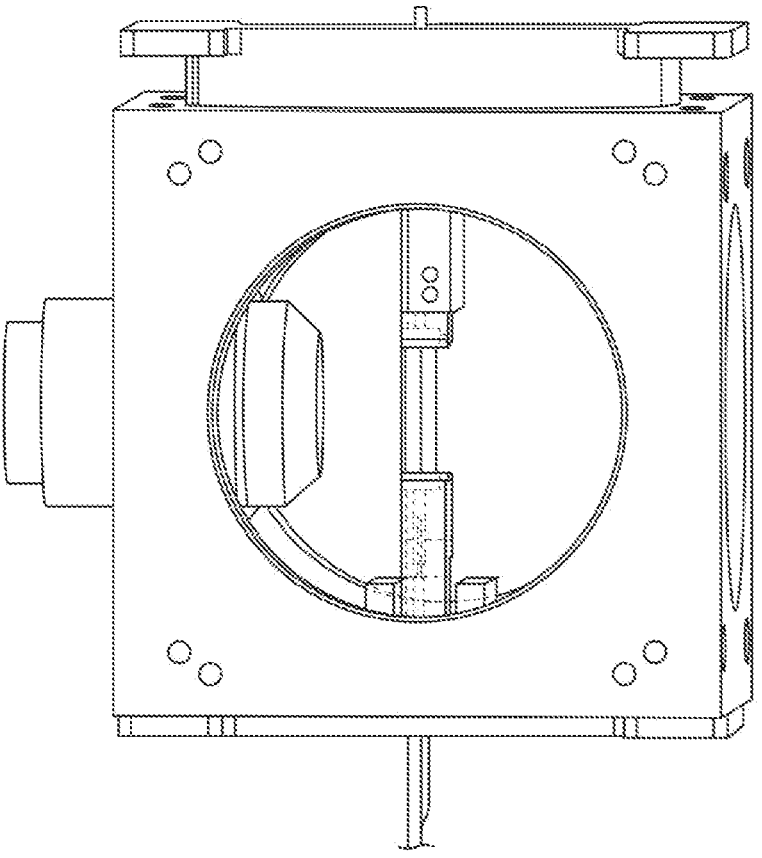
FIG. 2A shows a flow channel with collector, transverse view.
Figure 2B:
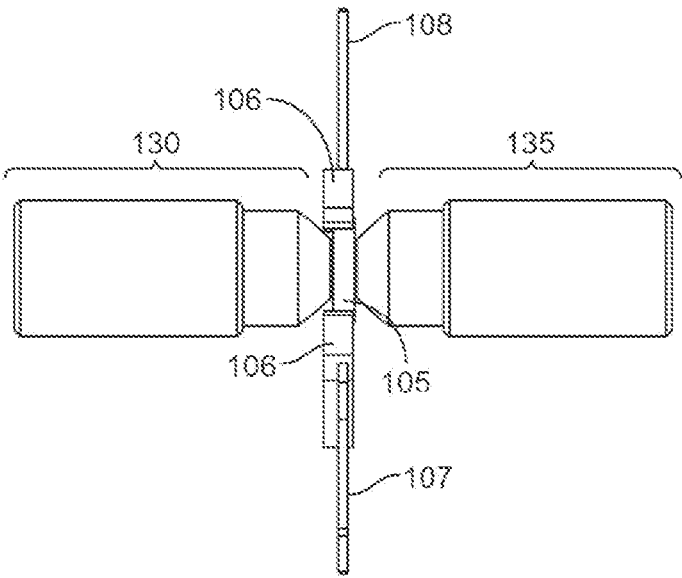
FIG. 2B shows a flow channel with two collectors.

A representative collection optic is shown in FIG. 2A, which includes a multi-lens assembly coupled to the long side of a flow cell using an index matching gel. The multi-lens assembly has a numerical aperture of ~1.0, a focal length of ~40 mm, and a magnification of ~3.2×. The multi-lens assembly collects light from each illumination volume within the measurement zone with a numerical aperture of 1.0 and images this light onto an array of optical fibers positioned at a distance of 14.98 mm from the rear lens of the assembly. In some configurations, collection optics are placed on opposite sides of the flow cell such that light is collected from both sides of the illumination volumes within the measurement zone (FIG. 2B).

Light Delivery

An optical fiber array delivers light to a point detection module and/or a spectral detection module. Custom optical fiber arrays are designed and fabricated to enable different operating conditions and experimental designs. In one configuration, light from one side of the measurement zone is imaged onto one fiber array, which delivers light from each illumination volume to a unique point in the focal plane of the spectral detection module. In a variant of this configuration, light collected from one of the illumination volumes is delivered to a point detection module, while the light collected from each of the other illumination volumes is delivered to a unique point in the focal plane of a spectral detection module. In another configuration, light from two sides of the measurement zone is imaged onto two fiber arrays, which are then combined to deliver light from both sides of each illumination volume to a unique point in the focal plane of the spectral detection module. In a variant of this configuration, light collected from one or two sides of one of the illumination volumes is delivered to a point detection module, while the light collected from each of the other illumination volumes is delivered to a unique point in the focal plane of the spectral detection module.

One implementation is to use a linear array of optical fibers spaced so that the light from each illumination volume is directed into a different fiber, and the output of that fiber is coupled into the spectral detection module such that a spectrally-resolved image of the fiber array is detected on a CCD sensor, with the spectrally resolved light from each probe volume detected on a different part of the CCD sensor (FIG. 3A). A representative optical fiber array is made of five 270 µm multimode fibers with 50 µm cladding stacked in a linear array with center-to-center spacing of ~320 µm, packaged in a SMA connector. The other end of the fiber array is positioned in front of a spectral dispersion module consisting of an imaging spectrograph with a collimating lens, edge and/or notch filters, a focusing lens, an aperture with a replaceable slit, a volume phase holographic grating, and a second focusing lens. Coupled to the spectral dispersion module is a spectral detection module, which includes a CCD camera interfaced to the data analysis system.

One of the fibers can be terminated separately (FIG. 3B). In this configuration, a fiber corresponding to one of the illumination volumes is terminated separately and coupled into a point detector for measurement, while the remaining fibers terminate in a linear array that is coupled to a spectral detection module.

In another configuration, two fiber arrays are used to collect light from two sides of the flow channel, the light from the two fiber arrays is combined and terminated in the fiber array and in a separate terminus (FIG. 3C and FIG. 3D). FIG. 3C shows two linear arrays of fibers used to collect light from two sides of the flow channel, fibers from corresponding illumination volumes combined, and one pair of combined fibers is terminated separately and coupled into a point detector for measurement, while the remaining fibers terminate in a linear array that is coupled into a spectral detection module. FIG. 3D shows two linear arrays of fibers used to collect light from two sides of the flow channel, and one fiber from one side is terminated separately and coupled into a point detector for measurement, while the corresponding fiber from the other side and the other combined corresponding fibers terminate in a linear array that is coupled into a spectral detection module. The separately terminated fiber is positioned in front of a point detection module which includes a collimating lens, bandpass filter and/or dichroic mirror, and photomultiplier tube (PMT) interfaced to the data analysis system.

Spectral Detection Module

A spectral detection module includes a Holospec imaging spectrograph and an Andor Newton EM CCD detector. The spectrograph employs interchangeable volume phase holographic (VPH) gratings for spectral dispersion of the light. The system is provided with interchangeable slits that can control the limiting aperture and spectral resolution of the spectrograph. In the absence of the slits, the optical fibers in the custom fiber array described above define the limiting aperture, and thus the minimum spectral resolution of the system. The spectral detection module images the spectral image of each fiber in the fiber array such that the spectral image of the light from each illumination volume is imaged onto a unique area on the detector. This is controlled by a custom-developed data analysis system.

A representative spectral detection module (FIG. 4A) includes a fiber array input adapter, collimating optics, a narrow band notch filter to reject excitation light, a grating to disperse the collected light, a focusing optic, and an array detector (e.g., CCD, CMOS array, avalanched photodiode array, or multianode PMT). In some configurations, the spectral detection module also has an additional focusing lens, slit or aperture, and a second collimating lens to provide a limiting aperture to adjust light throughput and spectral resolution (FIG. 4B).

Detector

A detector senses the spectral image of the light collected from each illumination volume on different areas of the sensor surface. In one configuration, the spectral image of each illumination volume is sensed on a different track on the sensor surface reflecting the linear arrangement of optical fibers in the fiber array. The detector can be programmed to read out the signal from the light on each track such that the spectra from each illumination volume is sent to the EEM FC data analysis system. Instructions for programming the detector operation and readout are provided by the EEM FC data analysis system. These instructions include measurement time, electronic gain, dimensions of each track, and desired resolution of the spectra from the illumination volumes. When each illumination volume is excited by a different illumination wavelength, the spectral image of the optical fiber array measured on the different detector tracks represents the hyperspectral image of the particle being measured.

Data Analysis System

A data analysis system includes custom analogue and digital signal processing hardware and software. Analogue hardware includes preamp circuits to process analogue signals from the PMTs, photodiodes, or other detectors, including amplification, filtering and baseline resort to null out DC signal if desired. The digital hardware includes a microprocessor that contains analogue to digital converters (ADCs) to sample the analogue signals to produce a digital stream of data, random access memory (RAM) to store the data, and a digital signal processor (DSP) core that performs digital signal processing, including digital signal filtering/conditioning, signal pulse detection, signal pulse analysis, and signal pulse classification. The digital hardware also includes digital to analogue converters (DACs) to communicate with detectors and a USB interface between the DSP and an external computer. The software includes routines to communicate with hardware and detectors, including setting detector operating conditions, receiving, processing, and analyzing data, controlling light sources, and controlling the fluidics module. The data analysis system sends instructions to the point detectors and spectral detection modules, receives signals and data from point detectors and spectral detection modules, sends instructions to the integrated laser module, processes data to detect and analyze particles to characterize, classify, or identify them. Data processing includes spectral analysis, including spectral unmixing, decomposition, and/or classification. Data processing algorithms are provided and accessed as MatLab scripts, C++ routines in the data analysis software, and/or executed in the data analysis hardware using DSPs and FPGAs. In controlling the light sources and detectors to produce hyperspectral data sets from single particles, and processing and analyzing that hyperspectral data set to characterize, classify, and/or identify single particles, the data analysis system provides high quality single particle resolution.

Figure 5:
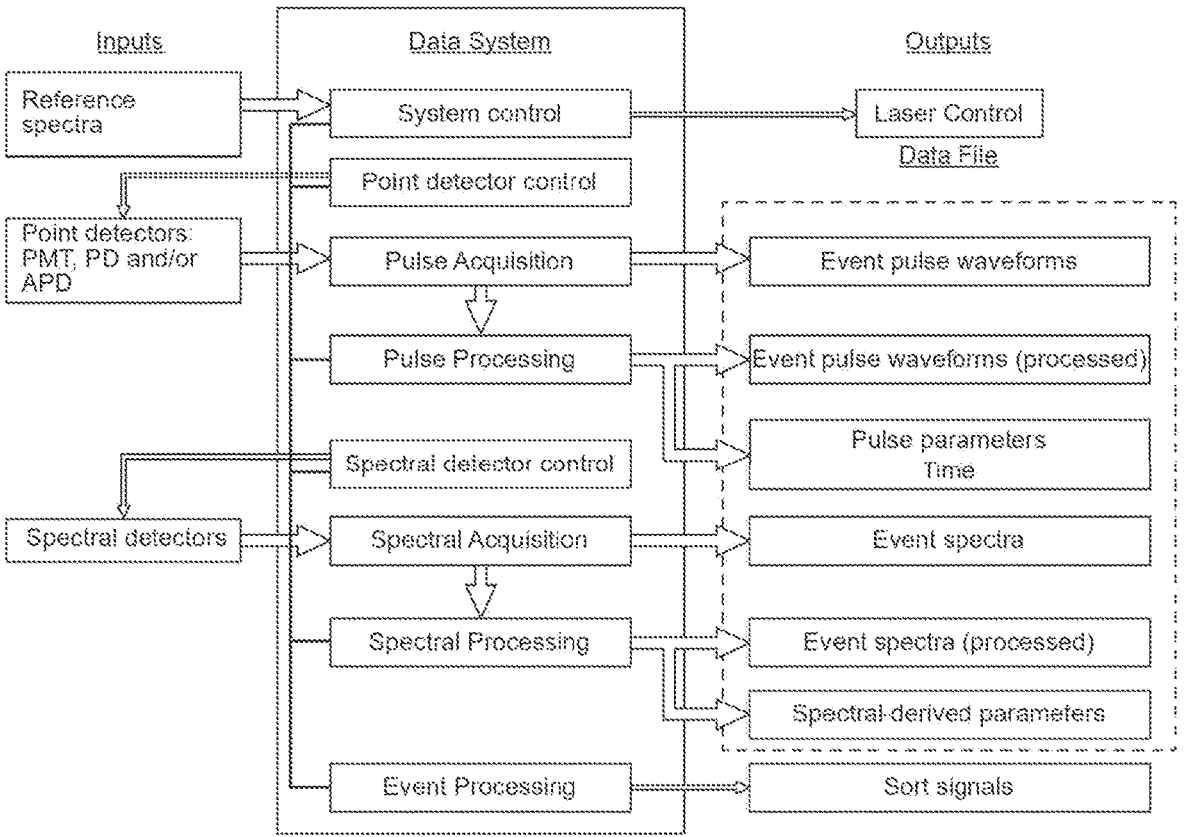
FIG. 5 shows a representative data analysis system.

A representative data analysis system (FIG. 5) is a custom system containing hardware and software that accepts data from point detectors (e.g., PDs, APDs, and PMTs) and spectral detectors (e.g., PMT, CCD, CMOS, or APD arrays). The data analysis system digitizes and analyzes the pulses to detect the occurrence of a particle and to extract one or more features of the signal pulses. The data analysis system communicates with the spectral detection module to trigger detection of the spectral signal and to receive, analyze and record the spectral data. The data analysis system controls the output of the light sources to synchronize with the passage of the particle through the illumination volumes within the measurement zone. The data analysis system operates in one of several measurement modes: conventional mode, where signals falling into discrete bandpass ranges are associated with specific fluorophores and/or fluorescent ligands; spectral mode, where the spectra of light coming from each illumination volume is analyzed to determine the signal from each of one or more known or unknown fluorophores; or hyperspectral mode, where the spectra of light from all of the illumination volumes is analyzed to determine the signal from each of one or more known or unknown fluorophores.

Below is a Table summarizing certain components of a representative EEM FC system.

TABLE

Certain components of an EEM FC system

| Component | Purpose | Types of Features | Representative Features |
|---|---|---|---|
| Flow channel | provide a measurement zone to interrogate a sample | A flow cell, capillary, microfabricated chamber, microfluidic chip | A rectangular (400 um × 180 um) flow cell |
| Fluidics module | presents the sample to the measurement zone | Reservoir, pumps or pressure-driven fluid delivery mechanisms, and valves to deliver sheath fluid and sample through the measurement zone | Computer controlled pumps and valves |
| Focused light sources | Illuminate the sample | Lasers, LEDs, lamps or other light sources with collimated output focused to illuminate discrete parts of the measurement zone | Lasers producing light at 405 nm, 492 nm and 640 nm (in certain embodiments, can be strobed to coincide with particle passage through each discrete part of the measurement zone that is illuminated - e.g., a measurement subzone) |
| Collection optics | collect the light produced by each focused light source in the measurement zone | A lens, microscope objective, mirror or other optic that collects light emanating from the measurement zone and directs it to the light path | two multi-element optics with each with an NA of 1.0 positioned on opposite sides of a rectangular flow cell and orthogonal to the path of the illumination light |
| Light path | deliver collected light produced by each focused light source to the dispersive optics | a medium through which collected light travels to the dispersive element, including air, optical fibers, waveguides | an optical fiber bundle consisting of two sets of 5-7 multimode optical fibers each with one terminus arranged in a linear array and a common terminus |
| Optics | spectrally separate the light from each focused light source | prism, grating, or other dispersive optic | a volume phase holographic grating |
| Detector | measures the spectrally-resolved light produced by each focused light source | photodiode array, CCD array, CCD camera, EMCCD camera, scientific CMOS camera | an EMCCD |
| Data system | produces multispectral and hyperspectral data sets for each particle and analyzes said data sets to determine the properties of individual particles | A system that employs analogue electronics and digital signal processing to analyze signal from the measurement zone and individual particles passing through the measurement zone. | A system that employs analogue electronics, digital signal processors, and field programmable gate arrays |

Example 7: Representative Illumination Module

Certain components described in Example 6 can be integrated as part of an illumination module. A representative illumination module includes a multi-wavelength laser system (VERSALASE, Vortran Laser Technologies) combining 492 nm (blue), 405 nm (violet), and 640 nm (red) diode laser modules that can be computer controlled and digitally modulated. The beams from the three lasers are steered via mirrors and optical glass and focused onto three spatially separated spots along the center of the flow cell in the direction of flow. The illumination module is connected to the flow cytometry data system (data analysis system) via a custom circuit designed to coordinate the illumination of the measurement probe volumes (measurement subzones) with particle passage through the flow cell. In the ready state, the first (bottom) blue laser is on and the 405 nm and 640 nm lasers are off. When a particle enters the first (blue 492 nm)

probe volume (measurement subzone), an optical signal (light scatter or fluorescence) is generated. The flow cytometer data system (data analysis system) detects this signal and sends an output signal via the custom circuit to a) turn off the blue laser at time x for duration x', when the particle has passed through its probe volume (measurement subzone); b) turn on the violet laser at time y for a duration y', when the particle passes through its probe volume (measurement subzone); and c) turn on the red laser at time z for a duration z' when the particle passes through its probe volume (measurement subzone); after which the system returns to the ready state. The times x, y, and z and durations x', y', and z' are chosen based on the linear velocity of particle flow through the flow cell that is determined by the sheath volumetric flow rate. The duration x' is also chosen based on the read-out speed of the detector.

As a particle in the flow cell passes through each measurement probe volume (measurement subzone) and is illuminated by the first, second, and third laser in sequence, the light collected from each of those probe volumes is spectrally dispersed and imaged into a corresponding detection zone on the surface of a detector. In one configuration, the light from each probe volume is focused into the end of an optical fiber that is part of an optical fiber array. The light from each fiber exits from the opposite end of the fiber array from which it is imaged through a volume phase holographic grating onto the face of a CCD sensor, such that images of the spectra from each probe volume is presented to a corresponding region of the CCD sensor surface. In this way, the entire hyperspectral data set including all of the emitted light from each of the laser-illuminated measurement probe volumes (illumination volumes) is captured on a single detector. This hyperspectral data stream is provided as input to the data analysis system where it can be processed, analyzed, and displayed.

The data analysis system includes electronic hardware with digital and analogue components to receive inputs from detectors, process those inputs so as to identify signals from particles, and allow control of detector gain. The data analysis system also includes software that controls the hardware, receives signal data from the hardware, and processes, analyzes, and saves data. The data analysis system receives data from point detectors such as photodiodes (PDs), avalanche photodiodes (APDs), and photomultiplier tubes (PMTs), and array detectors such as CCD arrays. The data analysis system receives the hyperspectral data stream from the CCD sensor and processes it to extract desired information. One form of processing includes supervised spectral unmixing, the determination of the abundance of components with known spectra. Another form of processing includes unsupervised spectral unmixing, where the number and abundance of components is not known. Another form of processing is classification, where particles are identified on the basis of a spectral signature. Another form of processing is the analysis of intensities within discrete bands of the spectrum.

The entirety of each patent, patent application, publication and document referenced herein is incorporated by reference. Citation of patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

The technology has been described with reference to specific implementations. The terms and expressions that have been utilized herein to describe the technology are descriptive and not necessarily limiting. Certain modifications made to the disclosed implementations can be considered within the scope of the technology. Certain aspects of the disclosed implementations suitably may be practiced in the presence or absence of certain elements not specifically disclosed herein.

Each of the terms "comprising," "consisting essentially of," and "consisting of" may be replaced with either of the other two terms. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%; e.g., a weight of "about 100 grams" can include a weight between 90 grams and 110 grams). Use of the term "about" at the beginning of a listing of values modifies each of the values (e.g., "about 1, 2 and 3" refers to "about 1, about 2 and about 3"). When a listing of values is described the listing includes all intermediate values and all fractional values thereof (e.g., the listing of values "80%, 85% or 90%" includes the intermediate value 86% and the fractional value 86.4%).

Certain implementations of the technology are set forth in the claim(s) that follow(s).

What is claimed is:

1. A flow cytometry system, comprising:
a flow channel comprising an inlet, an outlet, and two or more measurement subzones;
a fluidics module comprising a fluid delivery line to the flow channel inlet and fluid emission line from the flow channel outlet;
an illumination module comprising two or more light sources and a light source synchronizer comprising a controller and two or more switches, wherein:
   a) each of the light sources emits light of a different wavelength;
   b) each of the light sources is in communication with a measurement subzone located at a different location in the flow channel; and
   c) the controller in the light source synchronizer is configured to:
      (i) activate a first light source via a switch, wherein the switch illuminates a measurement subzone, while all other light sources are deactivated;
      (ii) deactivate the light source that illuminates the measurement subzone illuminated in (i) and activate a second light source that illuminates a measurement subzone different than the measurement subzone illuminated in (i) and located closer to the flow channel outlet, while all other light sources are deactivated, and
      (iii) repeat (i) and (ii) until a light source that illuminates a measurement subzone closest to the flow channel outlet is activated and then deactivated, or a light source that illuminates a measurement subzone selected as the terminal measurement subzone is activated and then deactivated, wherein the illumination module is in connection with a gate configured to: (a) detect the presence of a particle in a measurement subzone closest to the flow channel inlet, and (b) transmit a signal to the controller in the light source synchronizer to sequentially activate and deactivate light sources;
a light collector module comprising two collectors in communication with the measurement subzones of the flow channel;
a detector module comprising a selective optical element and a dispersive optical element; and
a light transmission module connected to the light collector module and the detector module, wherein the light transmission module is configured to combine the light from two collectors and deliver the combined light from the two collectors to the selective optical element and the dispersive optical element.

2. The flow cytometry system of claim 1, wherein the light source synchronizer comprises a controller and a plurality of switches.

3. The flow cytometry system of claim 2, wherein each of the switches is in separate communication with each of the light sources.

4. The flow cytometry system of claim 2, wherein the controller in the light source synchronizer is configured to sequentially activate and deactivate each of the light sources.

5. The flow cytometry system of claim 2, wherein the controller in the light source synchronizer is configured to (i)

activate and deactivate each of the switches, and (ii) activate each of the light sources one at a time while each of the other light sources is deactivated.

6. The flow cytometry system of claim 4, wherein the controller in the light source synchronizer is configured to sequentially activate one of the light sources after deactivating one of the other light sources.

7. The flow cytometry system of claim 1, wherein the measurement subzones are disposed at discrete positions in the flow channel and are disposed linearly in the direction of fluid flow in the flow channel.

8. The flow cytometry system of claim 7, wherein the controller in the light source synchronizer is configured to (i) activate a light source that illuminates a measurement subzone, while all other light sources are deactivated; (ii) deactivate the light source that illuminates the measurement subzone illuminated in (i) and activate a light source that illuminates a measurement subzone located next to the measurement subzone illuminated in (i) and closer to the flow channel outlet, while all other light sources are deactivated, and (iii) repeat (i) and (ii) until a light source that illuminates a measurement subzone closest to the flow channel outlet is activated and then deactivated.

9. The flow cytometry system of claim 1, wherein the illumination module is configured to sequentially generate a plurality of illumination volumes when each of the measurement subzones are sequentially illuminated.

10. The flow cytometry system of claim 1, wherein the illumination module comprises 2, 3, 4, 5, 6, 7, 8, 9, 10, 11, 12, 13, 14, 15, 16, 17, 18, 19 or 20 light sources.

11. The flow cytometry system of claim 1, comprising a data analysis system.

12. The flow cytometry system of claim 11, where the data analysis system is configured to analyze light detected by the detector.

13. The flow cytometry system of claim 11, wherein the detector comprises a selective optical element, and a selective subset of component signals obtained by the selective optical element is analyzed.

14. The flow cytometry system of claim 11, wherein the detector comprises a dispersive optical element, and (i) component spectral signals from a composite output signal of a single measurement subzone are analyzed, (ii) component spectral signals from a composite output signal of a plurality of measurement subzones are simultaneously analyzed, or (iii) a combination of (i) and (ii).

15. A combination, comprising:

(i) a kit, wherein the kit comprises:

a panel of optical standard particles, each capable of being conjugated to a distinct type/amount of optically detectable label or associated with a distinct molecular marker capable of being conjugated to a distinct type/amount of optically detectable label wherein:

the signals from the optically detectable labels of each member of the panel are calibrated according to size, type and/or amount of the particles, based on the measured optical intensities of each member of the panel of optical standard particles, and each member of the panel of optical standard particles has an excitation spectrum that is different than the excitation spectra of the other members of the panel, and/or each member of the panel of optical standard particles has an emission spectrum that is different than the emission spectra of the other members of the panel; and (ii) the flow cytometry system of claim 1.

* * * * *